United States Patent [19]
Casey et al.

[11] Patent Number: 5,854,001
[45] Date of Patent: Dec. 29, 1998

[54] HEPATITIS C VIRUS FUSION PROTEINS

[75] Inventors: James M. Casey; Suzanne L. Bode, both of Zion; Billy J. Zeck, Gurnee; Julie Yamaguchi, Chicago; Donald E. Frail; Suresh M. Desai, both of Libertyville; Sushil G. Devare, Northbrook, all of Ill.

[73] Assignee: Abbott Laboratories, Abbott Park, Ill.

[21] Appl. No.: 710,637

[22] Filed: Sep. 18, 1996

Related U.S. Application Data

[63] Continuation of Ser. No. 417,478, Apr. 5, 1995, abandoned, which is a continuation of Ser. No. 144,099, Oct. 28, 1993, abandoned, which is a continuation of Ser. No. 830,024, Jan. 31, 1992, abandoned.

[51] Int. Cl.$^6$ .......................... G01N 33/53; A61K 38/00; C07K 2/00
[52] U.S. Cl. .......................... 435/7.1; 435/69.7; 530/300; 530/350
[58] Field of Search .............................. 435/5, 69.3, 69.7, 435/7.1, 7.9, 7.8; 530/409, 826, 300, 350; 436/518

[56] References Cited

U.S. PATENT DOCUMENTS

| | | |
|---|---|---|
| 5,106,726 | 4/1992 | Wang . |
| 5,308,750 | 5/1994 | Mehta et al. . |

FOREIGN PATENT DOCUMENTS

| | | |
|---|---|---|
| 0318216 | 8/1989 | European Pat. Off. . |
| 0388232 | 9/1990 | European Pat. Off. . |
| 2212511 | 7/1989 | United Kingdom . |
| 9208734 | 5/1992 | WIPO . |

OTHER PUBLICATIONS

Uhlen, M. et al. (1990) Meth. Enzym. 185:129–143.
Yoshiharu Matsuura et al., Journal of Virology, vol. 66, No. 3, Mar. 1992, "Expression of processed envelope protein of Hepatitis C virus in mammalian and insect cells."
Hijikata et al., "Gene mapping of the putative structural . . . ," Proc. Natl. Acad. Sci. 88:5547–51 (1991).
Kato, N. et al (90) Proc. Natl. Acad. Sci USA 87: 9524–9528.
Okamoto, H. et al (91) J. Gen. Virol. 72: 2697–2704.
Weidemann, A. et al (89) Cell 57: 115–126.
Lowery, D.E. et al. (91) J. Biol. Chem. 266: 19842–19850.
Kit, M. et al (91) Vaccine 9 : 564–572.
Blam, S.B. et al (88) Oncogene 3: 129–136.
Li, J. et al (91) Gene 105:167–172.
Chiao, Q et al (91) Proc. Natl. Acad. Sci USA 2451–2455.
Krensdorf, O. et al (91) J. Gene. Virol. 72: 2557–2561.
Takamizawa, A. et al (91) J. Virol. 65:1105–1113.

Primary Examiner—Patricia Duffy
Attorney, Agent, or Firm—Cheryl L. Becker; Priscilla Porembski

[57] ABSTRACT

Mammalian expression systems for the production of HCV fusion proteins. Such expression systems provide high yields of HCV fusion proteins, and enable the development of diagnostic and therapeutic reagents which contain glycosylated structural antigens and also allow for the isolation of the HCV etiological agent.

3 Claims, 15 Drawing Sheets

HCV AA# 192-384
HGH SECRETION SIGNAL
CMV PROMOTER
HEK CELLS

SEQUENCE LISTING ( 1 ) GENERAL INFORMATION:

( i i i ) NUMBER OF SEQUENCES: 12

( 2 ) INFORMATION FOR SEQ ID NO:1:

(i) SEQUENCE CHARACTERISTICS:
   (A) LENGTH: 3011 amino acids
   (B) TYPE: amino acid
   (C) STRANDEDNESS: single
   (D) TOPOLOGY: linear (ii) MOLECULE TYPE: protein (xi) SEQUENCE DESCRIPTION: SEQ ID NO:1:

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
             100                 105                 110

Arg Arg Arg Ser Arg Asn Leu Gly Lys Val Ile Asp Thr Leu Thr Cys
             115                 120                 125

Gly Phe Ala Asp Leu Met Gly Tyr Ile Pro Leu Val Gly Ala Pro Leu
         130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                 165                 170                 175

Phe Leu Leu Ala Leu Leu Ser Cys Leu Thr Val Pro Ala Ser Ala Tyr
             180                 185                 190

Gln Val Arg Asn Ser Ser Gly Leu Tyr His Val Thr Asn Asp Cys Pro
         195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                 245                 250                 255

Gln Leu Arg Arg His Ile Asp Leu Leu Val Gly Ser Ala Thr Leu Cys
             260                 265                 270

Ser Ala Leu Tyr Val Gly Asp Leu Cys Gly Ser Val Phe Leu Val Gly
         275                 280                 285

Gln Leu Phe Thr Phe Ser Pro Arg Arg His Trp Thr Thr Gln Asp Cys
         290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                 325                 330                 335

Leu Leu Arg Ile Pro Gln Ala Ile Leu Asp Met Ile Ala Gly Ala His
             340                 345                 350

Trp Gly Val Leu Ala Gly Ile Ala Tyr Phe Ser Met Val Gly Asn Trp
         355                 360                 365

Ala Lys Val Leu Val Val Leu Leu Leu Phe Ala Gly Val Asp Ala Glu
```

|  |  |  | 370 |  |  |  |  |  | 375 |  |  |  |  |  | 380 |  |  |
|---|---|---|---|---|---|---|---|---|---|---|---|---|---|---|---|---|---|
| Thr 385 | His | Val | Thr | Gly | Gly 390 | Ser | Ala | Gly | His 395 | Thr | Ala | Gly | Leu | Val 400 |
| Arg | Leu | Leu | Ser | Pro 405 | Gly | Ala | Lys | Gln | Asn 410 | Ile | Gln | Leu | Ile | Asn 415 | Thr |
| Asn | Gly | Ser | Trp 420 | His | Ile | Asn | Ser | Thr 425 | Ala | Leu | Asn | Cys | Asn 430 | Glu | Ser |
| Leu | Asn | Thr 435 | Gly | Trp | Leu | Ala | Gly 440 | Leu | Phe | Tyr | His | His 445 | Lys | Phe | Asn |
| Ser | Ser 450 | Gly | Cys | Pro | Glu | Arg 455 | Leu | Ala | Ser | Cys | Arg 460 | Arg | Leu | Thr | Asp |
| Phe 465 | Ala | Gln | Gly | Gly | Gly 470 | Pro | Ile | Ser | Tyr | Ala 475 | Asn | Gly | Ser | Gly | Leu 480 |
| Asp | Glu | Arg | Pro | Tyr 485 | Cys | Trp | His | Tyr | Pro 490 | Arg | Pro | Cys | Gly 495 | Ile |
| Val | Pro | Ala | Lys 500 | Ser | Val | Cys | Gly | Pro 505 | Val | Tyr | Cys | Phe | Thr 510 | Pro | Ser |
| Pro | Val | Val 515 | Val | Gly | Thr | Thr | Asp 520 | Arg | Ser | Gly | Ala | Pro 525 | Thr | Tyr | Ser |
| Trp | Gly 530 | Ala | Asn | Asp | Thr | Asp 535 | Val | Phe | Val | Leu | Asn 540 | Asn | Thr | Arg | Pro |
| Pro 545 | Leu | Gly | Asn | Trp | Phe 550 | Gly | Cys | Thr | Trp | Met 555 | Asn | Ser | Thr | Gly | Phe 560 |
| Thr | Lys | Val | Cys | Gly 565 | Ala | Pro | Pro | Cys | Val 570 | Ile | Gly | Gly | Val | Gly 575 | Asn |
| Asn | Thr | Leu | Leu 580 | Cys | Pro | Thr | Asp | Cys 585 | Phe | Arg | Lys | His | Pro 590 | Glu | Ala |
| Thr | Tyr | Ser 595 | Arg | Cys | Gly | Ser | Gly 600 | Pro | Trp | Ile | Thr | Pro 605 | Arg | Cys | Met |
| Val | Asp 610 | Tyr | Pro | Tyr | Arg | Leu 615 | Trp | His | Tyr | Pro | Cys 620 | Thr | Ile | Asn | Tyr |
| Thr 625 | Ile | Phe | Lys | Val | Arg 630 | Met | Tyr | Val | Gly | Gly 635 | Val | Glu | His | Arg | Leu 640 |
| Glu | Ala | Ala | Cys | Asn 645 | Trp | Thr | Arg | Gly | Glu 650 | Arg | Cys | Asp | Leu | Glu 655 | Asp |
| Arg | Asp | Arg | Ser 660 | Glu | Leu | Ser | Pro | Leu 665 | Leu | Leu | Ser | Thr | Thr 670 | Gln | Trp |
| Gln | Val | Leu | Pro 675 | Cys | Ser | Phe | Thr 680 | Thr | Leu | Pro | Ala | Leu 685 | Ser | Thr | Gly |
| Leu | Ile 690 | His | Leu | His | Gln | Asn 695 | Ile | Val | Asp | Val | Gln 700 | Tyr | Leu | Tyr | Gly |
| Val 705 | Gly | Ser | Ser | Ile | Ala 710 | Ser | Trp | Ala | Ile | Lys 715 | Trp | Glu | Tyr | Val | Val 720 |
| Leu | Leu | Phe | Leu | Leu 725 | Leu | Ala | Asp | Ala | Arg 730 | Val | Cys | Ser | Cys | Leu 735 | Trp |
| Met | Met | Leu | Leu 740 | Ile | Ser | Gln | Ala | Glu 745 | Ala | Ala | Leu | Glu | Asn 750 | Leu | Val |
| Ile | Leu | Asn 755 | Ala | Ala | Ser | Leu | Ala 760 | Gly | Thr | His | Gly | Phe 765 | Val | Ser | Phe |
| Leu | Val 770 | Phe | Phe | Cys | Phe | Ala 775 | Trp | Tyr | Leu | Lys | Gly 780 | Arg | Trp | Val | Pro |
| Gly 785 | Ala | Ala | Tyr | Ala | Leu 790 | Tyr | Gly | Ile | Trp | Pro 795 | Leu | Leu | Leu | Leu | Leu 800 |

```
Leu Ala Leu Pro Gln Arg Ala Tyr Ala Leu Asp Thr Glu Val Ala Ala
            805                 810                 815
Ser Cys Gly Gly Val Val Leu Val Gly Leu Met Ala Leu Thr Leu Ser
            820                 825                 830
Pro Tyr Tyr Lys Arg Tyr Ile Ser Trp Cys Met Trp Trp Leu Gln Tyr
            835                 840                 845
Phe Leu Thr Arg Val Glu Ala Gln Leu His Val Trp Val Pro Pro Leu
            850                 855                 860
Asn Val Arg Gly Gly Arg Asp Ala Val Ile Leu Leu Met Cys Ala Val
865                 870                 875                 880
His Pro Thr Leu Val Phe Asp Ile Thr Lys Leu Leu Leu Ala Ile Phe
            885                 890                 895
Gly Pro Leu Trp Ile Leu Gln Ala Ser Leu Leu Lys Val Pro Tyr Phe
            900                 905                 910
Val Arg Val Gln Gly Leu Leu Arg Ile Cys Ala Leu Ala Arg Lys Ile
            915                 920                 925
Ala Gly Gly His Tyr Val Gln Met Ile Phe Ile Lys Leu Gly Ala Leu
            930                 935                 940
Thr Gly Thr Tyr Val Tyr Asn His Leu Thr Pro Leu Arg Asp Trp Ala
945                 950                 955                 960
His Asn Gly Leu Arg Asp Leu Ala Val Ala Val Glu Pro Val Val Phe
            965                 970                 975
Ser Arg Met Glu Thr Lys Leu Ile Thr Trp Gly Ala Asp Thr Ala Ala
            980                 985                 990
Cys Gly Asp Ile Ile Asn Gly Leu Pro Val Ser Ala Arg Arg Gly Gln
            995                 1000                1005
Glu Ile Leu Leu Gly Pro Ala Asp Gly Met Val Ser Lys Gly Trp Arg
            1010                1015                1020
Leu Leu Ala Pro Ile Thr Ala Tyr Ala Gln Gln Thr Arg Gly Leu Leu
1025                1030                1035                1040
Gly Cys Ile Ile Thr Ser Leu Thr Gly Arg Asp Lys Asn Gln Val Glu
            1045                1050                1055
Gly Glu Val Gln Ile Val Ser Thr Ala Thr Gln Thr Phe Leu Ala Thr
            1060                1065                1070
Cys Ile Asn Gly Val Cys Trp Thr Val Tyr His Gly Ala Gly Thr Arg
            1075                1080                1085
Thr Ile Ala Ser Pro Lys Gly Pro Val Ile Gln Met Tyr Thr Asn Val
            1090                1095                1100
Asp Gln Asp Leu Val Gly Trp Pro Ala Pro Gln Gly Ser Arg Ser Leu
1105                1110                1115                1120
Thr Pro Cys Thr Cys Gly Ser Ser Asp Leu Tyr Leu Val Thr Arg His
            1125                1130                1135
Ala Asp Val Ile Pro Val Arg Arg Gln Gly Asp Ser Arg Gly Ser Leu
            1140                1145                1150
Leu Ser Pro Arg Pro Ile Ser Tyr Leu Lys Gly Ser Ser Gly Gly Pro
            1155                1160                1165
Leu Leu Cys Pro Ala Gly His Ala Val Gly Leu Phe Arg Ala Ala Val
            1170                1175                1180
Cys Thr Arg Gly Val Ala Lys Ala Val Asp Phe Ile Pro Val Glu Asn
1185                1190                1195                1200
Leu Glu Thr Thr Met Arg Ser Pro Val Phe Thr Asp Asn Ser Ser Pro
            1205                1210                1215
Pro Ala Val Pro Gln Ser Phe Gln Val Ala His Leu His Ala Pro Thr
            1220                1225                1230
```

```
Gly  Ser  Gly  Lys  Ser  Thr  Lys  Val  Pro  Ala  Ala  Tyr  Ala  Ala  Gln  Gly
          1235                1240                1245

Tyr  Lys  Val  Leu  Val  Leu  Asn  Pro  Ser  Val  Ala  Ala  Thr  Leu  Gly  Phe
     1250                1255                1260

Gly  Ala  Tyr  Met  Ser  Lys  Ala  His  Gly  Val  Asp  Pro  Asn  Ile  Arg  Thr
1265                1270                1275                1280

Gly  Val  Arg  Thr  Ile  Thr  Thr  Gly  Ser  Pro  Ile  Thr  Tyr  Ser  Thr  Tyr
               1285                1290                1295

Gly  Lys  Phe  Leu  Ala  Asp  Gly  Gly  Cys  Ser  Gly  Gly  Ala  Tyr  Asp  Ile
          1300                1305                1310

Ile  Ile  Cys  Asp  Glu  Cys  His  Ser  Thr  Asp  Ala  Thr  Ser  Ile  Leu  Gly
          1315                1320                1325

Ile  Gly  Thr  Val  Leu  Asp  Gln  Ala  Glu  Thr  Ala  Gly  Ala  Arg  Leu  Val
          1330                1335                1340

Val  Leu  Ala  Thr  Ala  Thr  Pro  Pro  Gly  Ser  Val  Thr  Val  Pro  His  Pro
1345                1350                1355                1360

Asn  Ile  Glu  Glu  Val  Ala  Leu  Ser  Thr  Thr  Gly  Glu  Ile  Pro  Phe  Tyr
                    1365                1370                1375

Gly  Lys  Ala  Ile  Pro  Leu  Glu  Val  Ile  Lys  Gly  Gly  Arg  His  Leu  Ile
               1380                1385                1390

Phe  Cys  His  Ser  Lys  Lys  Lys  Cys  Asp  Glu  Leu  Ala  Ala  Lys  Leu  Val
          1395                1400                1405

Ala  Leu  Gly  Ile  Asn  Ala  Val  Ala  Tyr  Tyr  Arg  Gly  Leu  Asp  Val  Ser
          1410                1415                1420

Val  Ile  Pro  Ala  Ser  Gly  Asp  Val  Val  Val  Val  Ser  Thr  Asp  Ala  Leu
1425                1430                1435                1440

Met  Thr  Gly  Phe  Thr  Gly  Asp  Phe  Asp  Pro  Val  Ile  Asp  Cys  Asn  Thr
               1445                1450                1455

Cys  Val  Thr  Gln  Thr  Val  Asp  Phe  Ser  Leu  Asp  Pro  Thr  Phe  Thr  Ile
               1460                1465                1470

Glu  Thr  Thr  Thr  Leu  Pro  Gln  Asp  Ala  Val  Ser  Arg  Thr  Gln  Arg  Arg
          1475                1480                1485

Gly  Arg  Thr  Gly  Arg  Gly  Lys  Pro  Gly  Ile  Tyr  Arg  Phe  Val  Ala  Pro
1490                1495                1500

Gly  Glu  Arg  Pro  Ser  Gly  Met  Phe  Asp  Ser  Ser  Val  Leu  Cys  Glu  Cys
1505                1510                1515                1520

Tyr  Asp  Ala  Gly  Cys  Ala  Trp  Tyr  Glu  Leu  Thr  Pro  Ala  Glu  Thr  Thr
               1525                1530                1535

Val  Arg  Leu  Arg  Ala  Tyr  Met  Asn  Thr  Pro  Gly  Leu  Pro  Val  Cys  Gln
               1540                1545                1550

Asp  His  Leu  Glu  Phe  Trp  Glu  Gly  Val  Phe  Thr  Gly  Leu  Thr  His  Ile
               1555                1560                1565

Asp  Ala  His  Phe  Leu  Ser  Gln  Thr  Lys  Gln  Ser  Gly  Glu  Asn  Phe  Pro
               1570                1575                1580

Tyr  Leu  Val  Ala  Tyr  Gln  Ala  Thr  Val  Cys  Ala  Arg  Ala  Gln  Ala  Pro
1585                1590                1595                1600

Pro  Pro  Ser  Trp  Asp  Gln  Met  Trp  Lys  Cys  Leu  Ile  Arg  Leu  Lys  Pro
               1605                1610                1615

Thr  Leu  His  Gly  Pro  Thr  Pro  Leu  Leu  Tyr  Arg  Leu  Gly  Ala  Val  Gln
               1620                1625                1630

Asn  Glu  Ile  Thr  Leu  Thr  His  Pro  Val  Thr  Lys  Tyr  Ile  Met  Thr  Cys
               1635                1640                1645

Met  Ser  Ala  Asn  Pro  Glu  Val  Val  Thr  Ser  Thr  Trp  Val  Leu  Val  Gly
```

```
            1650                    1655                    1660
Gly  Val  Leu  Ala  Ala  Leu  Ala  Ala  Tyr  Cys  Leu  Ser  Thr  Gly  Cys  Val
1665                 1670                    1675                    1680

Val  Ile  Val  Gly  Arg  Ile  Val  Leu  Ser  Gly  Lys  Pro  Ala  Ile  Ile  Pro
                     1685                    1690                    1695

Asp  Arg  Glu  Val  Leu  Tyr  Gln  Glu  Phe  Asp  Glu  Met  Glu  Glu  Cys  Ser
                     1700                    1705                    1710

Gln  His  Leu  Pro  Tyr  Ile  Glu  Gln  Gly  Met  Met  Leu  Ala  Glu  Gln  Phe
                     1715                    1720                    1725

Lys  Gln  Glu  Ala  Leu  Gly  Leu  Leu  Gln  Thr  Ala  Ser  Arg  Gln  Ala  Glu
                     1730                    1735                    1740

Val  Ile  Thr  Pro  Ala  Val  Gln  Thr  Asn  Trp  Gln  Lys  Leu  Glu  Ala  Phe
1745                 1750                    1755                    1760

Trp  Ala  Lys  His  Met  Trp  Asn  Phe  Ile  Ser  Gly  Thr  Gln  Tyr  Leu  Ala
                     1765                    1770                    1775

Gly  Leu  Ser  Thr  Leu  Pro  Gly  Asn  Pro  Ala  Ile  Ala  Ser  Leu  Met  Ala
                     1780                    1785                    1790

Phe  Thr  Ala  Ala  Val  Thr  Ser  Pro  Leu  Thr  Thr  Ser  Gln  Thr  Leu  Leu
                     1795                    1800                    1805

Phe  Asn  Ile  Leu  Gly  Gly  Trp  Val  Ala  Ala  Gln  Leu  Ala  Ala  Pro  Gly
                     1810                    1815                    1820

Ala  Ala  Thr  Ala  Phe  Val  Gly  Ala  Gly  Leu  Ala  Gly  Ala  Ala  Ile  Gly
1825                 1830                    1835                    1840

Ser  Val  Gly  Leu  Gly  Lys  Val  Leu  Val  Asp  Ile  Leu  Ala  Gly  Tyr  Gly
                     1845                    1850                    1855

Ala  Gly  Val  Ala  Gly  Ala  Leu  Val  Ala  Phe  Lys  Ile  Met  Ser  Gly  Glu
                     1860                    1865                    1870

Val  Pro  Ser  Thr  Glu  Asp  Leu  Val  Asn  Leu  Leu  Pro  Ala  Ile  Leu  Ser
                     1875                    1880                    1885

Pro  Gly  Ala  Leu  Val  Val  Gly  Val  Val  Cys  Ala  Ala  Ile  Leu  Arg  Arg
                     1890                    1895                    1900

His  Val  Gly  Pro  Gly  Glu  Gly  Ala  Val  Gln  Trp  Met  Asn  Arg  Leu  Ile
1905                 1910                    1915                    1920

Ala  Phe  Ala  Ser  Arg  Gly  Asn  His  Val  Ser  Pro  Thr  His  Tyr  Val  Pro
                     1925                    1930                    1935

Glu  Ser  Asp  Ala  Ala  Ala  Arg  Val  Thr  Ala  Ile  Leu  Ser  Asn  Leu  Thr
                     1940                    1945                    1950

Val  Thr  Gln  Leu  Leu  Arg  Arg  Leu  His  Gln  Trp  Ile  Gly  Ser  Glu  Cys
                     1955                    1960                    1965

Thr  Thr  Pro  Cys  Ser  Gly  Ser  Trp  Leu  Arg  Asp  Ile  Trp  Asp  Trp  Ile
                     1970                    1975                    1980

Cys  Glu  Val  Leu  Ser  Asp  Phe  Lys  Thr  Trp  Leu  Lys  Ala  Lys  Leu  Met
1985                 1990                    1995                    2000

Pro  Gln  Leu  Pro  Gly  Ile  Pro  Phe  Val  Ser  Cys  Gln  Arg  Gly  Tyr  Arg
                     2005                    2010                    2015

Gly  Val  Trp  Arg  Gly  Asp  Gly  Ile  Met  His  Thr  Arg  Cys  His  Cys  Gly
                     2020                    2025                    2030

Ala  Glu  Ile  Thr  Gly  His  Val  Lys  Asn  Gly  Thr  Met  Arg  Ile  Val  Gly
                     2035                    2040                    2045

Pro  Arg  Thr  Cys  Arg  Asn  Met  Trp  Ser  Gly  Thr  Phe  Pro  Ile  Asn  Ala
                     2050                    2055                    2060

Tyr  Thr  Thr  Gly  Pro  Cys  Thr  Pro  Leu  Pro  Ala  Pro  Asn  Tyr  Lys  Phe
2065                 2070                    2075                    2080
```

```
Ala Leu Trp Arg Val Ser Ala Glu Glu Tyr Val Glu Ile Arg Arg Val
               2085                2090                2095
Gly Asp Phe His Tyr Val Ser Gly Met Thr Thr Asp Asn Leu Lys Cys
               2100                2105                2110
Pro Cys Gln Ile Pro Ser Pro Glu Phe Phe Thr Glu Leu Asp Gly Val
               2115                2120                2125
Arg Leu His Arg Phe Ala Pro Pro Cys Lys Pro Leu Leu Arg Glu Glu
               2130                2135                2140
Val Ser Phe Arg Val Gly Leu His Glu Tyr Pro Val Gly Ser Gln Leu
2145                2150                2155                2160
Pro Cys Glu Pro Glu Pro Asp Val Ala Val Leu Thr Ser Met Leu Thr
               2165                2170                2175
Asp Pro Ser His Ile Thr Ala Glu Ala Ala Gly Arg Arg Leu Ala Arg
               2180                2185                2190
Gly Ser Pro Pro Ser Met Ala Ser Ser Ser Ala Ser Gln Leu Ser Ala
               2195                2200                2205
Pro Ser Leu Lys Ala Thr Cys Thr Thr Asn His Asp Ser Pro Asp Ala
               2210                2215                2220
Glu Leu Ile Glu Ala Asn Leu Leu Trp Arg Gln Glu Met Gly Gly Asn
2225                2230                2235                2240
Ile Thr Arg Val Glu Ser Glu Asn Lys Val Val Ile Leu Asp Ser Phe
               2245                2250                2255
Asp Pro Leu Val Ala Glu Glu Asp Glu Arg Glu Val Ser Val Pro Ala
               2260                2265                2270
Glu Ile Leu Arg Lys Ser Gln Arg Phe Ala Arg Ala Leu Pro Val Trp
               2275                2280                2285
Ala Arg Pro Asp Tyr Asn Pro Pro Leu Ile Glu Thr Trp Lys Glu Pro
               2290                2295                2300
Asp Tyr Glu Pro Pro Val Val His Gly Cys Pro Leu Pro Pro Pro Arg
2305                2310                2315                2320
Ser Pro Pro Val Pro Pro Pro Arg Lys Lys Arg Thr Val Val Leu Thr
               2325                2330                2335
Glu Ser Thr Leu Ser Thr Ala Leu Ala Glu Leu Ala Thr Lys Ser Phe
               2340                2345                2350
Gly Ser Ser Ser Thr Ser Gly Ile Thr Gly Asp Asn Thr Thr Thr Ser
               2355                2360                2365
Ser Glu Pro Ala Pro Ser Gly Cys Pro Pro Asp Ser Asp Val Glu Ser
               2370                2375                2380
Tyr Ser Ser Met Pro Pro Leu Glu Gly Glu Pro Gly Asp Pro Asp Phe
2385                2390                2395                2400
Ser Asp Gly Ser Trp Ser Thr Val Ser Ser Gly Ala Asp Thr Glu Asp
               2405                2410                2415
Val Val Cys Cys Ser Met Ser Tyr Ser Trp Thr Gly Ala Leu Val Thr
               2420                2425                2430
Pro Cys Ala Ala Glu Glu Gln Lys Leu Pro Ile Asn Ala Leu Ser Asn
               2435                2440                2445
Ser Leu Leu Arg His His Asn Leu Val Tyr Ser Thr Thr Ser Arg Ser
               2450                2455                2460
Ala Cys Gln Arg Gln Lys Lys Val Thr Phe Asp Arg Leu Gln Val Leu
2465                2470                2475                2480
Asp Ser His Tyr Gln Asp Val Leu Lys Glu Val Lys Ala Ala Ala Ser
               2485                2490                2495
Arg Val Lys Ala Asn Leu Leu Ser Val Glu Glu Ala Cys Ser Leu Thr
               2500                2505                2510
```

Pro Pro His Ser Ala Lys Ser Lys Phe Gly Tyr Gly Ala Lys Asp Val
        2515                2520                2525
Arg Cys His Ala Arg Lys Ala Val Ala His Ile Asn Ser Val Trp Lys
    2530                2535                2540
Asp Leu Leu Glu Asp Ser Val Thr Pro Ile Asp Thr Thr Ile Met Ala
2545                2550                2555                2560
Lys Asn Glu Val Phe Cys Val Gln Pro Glu Lys Gly Gly Arg Lys Pro
                2565                2570                2575
Ala Arg Leu Ile Val Phe Pro Asp Leu Gly Val Arg Val Cys Glu Lys
            2580                2585                2590
Met Ala Leu Tyr Asp Val Val Ser Lys Leu Pro Leu Ala Val Met Gly
        2595                2600                2605
Ser Ser Tyr Gly Phe Gln Tyr Ser Pro Gly Gln Arg Val Glu Phe Leu
    2610                2615                2620
Val Gln Ala Trp Lys Ser Lys Lys Thr Pro Met Gly Phe Ser Tyr Asp
2625                2630                2635                2640
Thr Arg Cys Phe Asp Ser Thr Val Thr Glu Ser Asp Ile Arg Thr Glu
                2645                2650                2655
Glu Ala Ile Tyr Gln Cys Cys Asp Leu Asp Pro Gln Ala Arg Val Ala
            2660                2665                2670
Ile Lys Ser Leu Thr Glu Arg Leu Tyr Val Gly Gly Pro Leu Thr Asn
        2675                2680                2685
Ser Arg Gly Glu Asn Cys Gly Tyr Arg Arg Cys Arg Ala Ser Gly Val
    2690                2695                2700
Leu Thr Thr Ser Cys Gly Asn Thr Leu Thr Cys Tyr Ile Lys Ala Arg
2705                2710                2715                2720
Ala Ala Cys Arg Ala Ala Gly Leu Gln Asp Arg Thr Met Leu Val Cys
                2725                2730                2735
Gly Asp Asp Leu Val Val Ile Cys Glu Ser Ala Gly Val Gln Glu Asp
            2740                2745                2750
Ala Ala Ser Leu Arg Ala Phe Thr Glu Ala Met Thr Arg Tyr Ser Ala
        2755                2760                2765
Pro Pro Gly Asp Pro Pro Gln Pro Glu Tyr Asp Leu Glu Leu Ile Thr
    2770                2775                2780
Ser Cys Ser Ser Asn Val Ser Val Ala His Asp Gly Ala Gly Lys Arg
2785                2790                2795                2800
Val Tyr Tyr Leu Thr Arg Asp Pro Thr Thr Pro Leu Ala Arg Ala Ala
                2805                2810                2815
Trp Glu Thr Ala Arg His Thr Pro Val Asn Ser Trp Leu Gly Asn Ile
            2820                2825                2830
Ile Met Phe Ala Pro Thr Leu Trp Ala Arg Met Ile Leu Met Thr His
        2835                2840                2845
Phe Phe Ser Val Leu Ile Ala Arg Asp Gln Phe Glu Gln Ala Leu Asn
    2850                2855                2860
Cys Glu Ile Tyr Gly Ala Cys Tyr Ser Ile Glu Pro Leu Asp Leu Pro
2865                2870                2875                2880
Pro Ile Ile Gln Arg Leu His Gly Leu Ser Ala Phe Ser Leu His Ser
                2885                2890                2895
Tyr Ser Pro Gly Glu Ile Asn Arg Val Ala Ala Cys Leu Arg Lys Leu
            2900                2905                2910
Gly Val Pro Pro Leu Arg Ala Trp Lys His Arg Ala Arg Ser Val Arg
        2915                2920                2925
Ala Arg Leu Leu Ser Arg Gly Gly Arg Ala Ala Ile Cys Gly Lys Tyr

```
                      2930                    2935                         2940

Leu  Phe  Asn  Trp  Ala  Val  Arg  Thr  Lys  Pro  Lys  Leu  Thr  Pro  Ile  Ala
        2945                     2950                    2955                         2960

Ala  Ala  Gly  Arg  Leu  Asp  Leu  Ser  Gly  Trp  Phe  Thr  Ala  Gly  Tyr  Ser
                            2965                    2970                         2975

Gly  Gly  Asp  Ile  Tyr  His  Ser  Val  Ser  His  Ala  Arg  Pro  Arg  Trp  Ser
                            2980                    2985                         2990

Trp  Phe  Cys  Leu  Leu  Leu  Leu  Ala  Ala  Gly  Val  Gly  Ile  Tyr  Leu  Leu
                            2995                    3000                         3005

Pro  Asn  Arg
                  3010
```

( 2 ) INFORMATION FOR SEQ ID NO:2:

( i ) SEQUENCE CHARACTERISTICS:
        ( A ) LENGTH: 3011 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
        Met  Ser  Thr  Asn  Pro  Lys  Pro  Gln  Arg  Lys  Thr  Lys  Arg  Asn  Thr  Asn
        1                   5                        10                       15

Arg  Arg  Pro  Gln  Asp  Val  Lys  Phe  Pro  Gly  Gly  Gly  Gln  Ile  Val  Gly
                            20                       25                       30

Gly  Val  Tyr  Leu  Leu  Pro  Arg  Arg  Gly  Pro  Arg  Leu  Gly  Val  Arg  Ala
                       35                       40                       45

Thr  Arg  Lys  Thr  Ser  Glu  Arg  Ser  Gln  Pro  Arg  Gly  Arg  Arg  Gln  Pro
                  50                       55                       60

Ile  Pro  Lys  Ala  Arg  Arg  Pro  Glu  Gly  Arg  Thr  Trp  Ala  Gln  Pro  Gly
        65                       70                       75                       80

Tyr  Pro  Trp  Pro  Leu  Tyr  Gly  Asn  Glu  Gly  Cys  Gly  Trp  Ala  Gly  Trp
                            85                       90                       95

Leu  Leu  Ser  Pro  Arg  Gly  Ser  Arg  Pro  Ser  Trp  Gly  Pro  Thr  Asp  Pro
                            100                      105                      110

Arg  Arg  Arg  Ser  Arg  Asn  Leu  Gly  Lys  Val  Ile  Asp  Thr  Leu  Thr  Cys
                       115                      120                      125

Gly  Phe  Ala  Asp  Leu  Met  Gly  Tyr  Ile  Pro  Leu  Val  Gly  Ala  Pro  Leu
                  130                      135                      140

Gly  Gly  Ala  Ala  Arg  Ala  Leu  Ala  His  Gly  Val  Arg  Val  Leu  Glu  Asp
        145                      150                      155                      160

Gly  Val  Asn  Tyr  Ala  Thr  Gly  Asn  Leu  Pro  Gly  Cys  Ser  Phe  Ser  Ile
                            165                      170                      175

Phe  Leu  Leu  Ala  Leu  Leu  Ser  Cys  Leu  Thr  Val  Pro  Ala  Ser  Ala  Tyr
                            180                      185                      190

Gln  Val  Arg  Asn  Ser  Ser  Gly  Leu  Tyr  His  Val  Thr  Asn  Asp  Cys  Pro
                       195                      200                      205

Asn  Ser  Ser  Ile  Val  Tyr  Glu  Thr  Ala  Asp  Thr  Ile  Leu  His  Ser  Pro
                  210                      215                      220

Gly  Cys  Val  Pro  Cys  Val  Arg  Glu  Gly  Asn  Thr  Ser  Lys  Cys  Trp  Val
        225                      230                      235                      240

Ala  Val  Ala  Pro  Thr  Val  Thr  Thr  Arg  Asp  Gly  Lys  Leu  Pro  Ser  Thr
                            245                      250                      255

Gln  Leu  Arg  Arg  His  Ile  Asp  Leu  Leu  Val  Gly  Ser  Ala  Thr  Leu  Cys
                            260                      265                      270
```

```
Ser  Ala  Leu  Tyr  Val  Gly  Asp  Leu  Cys  Gly  Ser  Val  Phe  Leu  Val  Ser
          275                 280                      285

Gln  Leu  Phe  Thr  Phe  Ser  Pro  Arg  Arg  His  Trp  Thr  Thr  Gln  Asp  Cys
     290                      295                 300

Asn  Cys  Ser  Ile  Tyr  Pro  Gly  His  Ile  Thr  Gly  His  Arg  Met  Ala  Trp
305                      310                 315                           320

Asp  Met  Met  Met  Asn  Trp  Ser  Pro  Thr  Thr  Ala  Leu  Val  Val  Ala  Gln
                    325                      330                           335

Leu  Leu  Arg  Ile  Pro  Gln  Ala  Ile  Leu  Asp  Met  Ile  Ala  Gly  Ala  His
               340                 345                      350

Trp  Gly  Val  Leu  Ala  Gly  Ile  Ala  Tyr  Phe  Ser  Met  Val  Gly  Asn  Trp
          355                 360                      365

Ala  Lys  Val  Leu  Val  Val  Leu  Leu  Phe  Ser  Gly  Val  Asp  Ala  Ala
     370                 375                      380

Thr  Tyr  Thr  Thr  Gly  Gly  Ser  Val  Ala  Arg  Thr  Thr  His  Gly  Leu  Ser
385                      390                 395                           400

Ser  Leu  Phe  Ser  Gln  Gly  Ala  Lys  Gln  Asn  Ile  Gln  Leu  Ile  Asn  Thr
               405                 410                      415

Asn  Gly  Ser  Trp  His  Ile  Asn  Arg  Thr  Ala  Leu  Asn  Cys  Asn  Ala  Ser
               420                 425                      430

Leu  Asp  Thr  Gly  Trp  Val  Ala  Gly  Leu  Phe  Tyr  Tyr  His  Lys  Phe  Asn
          435                 440                      445

Ser  Ser  Gly  Cys  Pro  Glu  Arg  Met  Ala  Ser  Cys  Arg  Pro  Leu  Ala  Asp
     450                      455                 460

Phe  Asp  Gln  Gly  Trp  Gly  Pro  Ile  Ser  Tyr  Thr  Asn  Gly  Ser  Gly  Pro
465                      470                 475                           480

Glu  His  Arg  Pro  Tyr  Cys  Trp  His  Tyr  Pro  Pro  Lys  Pro  Cys  Gly  Ile
               485                 490                      495

Val  Pro  Ala  Gln  Ser  Val  Cys  Gly  Pro  Val  Tyr  Cys  Phe  Thr  Pro  Ser
               500                 505                      510

Pro  Val  Val  Val  Gly  Thr  Thr  Asp  Lys  Ser  Gly  Ala  Pro  Thr  Tyr  Thr
          515                 520                      525

Trp  Gly  Ser  Asn  Asp  Thr  Asp  Val  Phe  Val  Leu  Asn  Asn  Thr  Arg  Pro
     530                      535                 540

Pro  Pro  Gly  Asn  Trp  Phe  Gly  Cys  Thr  Trp  Met  Asn  Ser  Ser  Gly  Phe
545                      550                 555                           560

Thr  Lys  Val  Cys  Gly  Ala  Pro  Pro  Cys  Val  Ile  Gly  Gly  Ala  Gly  Asn
               565                 570                      575

Asn  Thr  Leu  His  Cys  Pro  Thr  Asp  Cys  Phe  Arg  Lys  His  Pro  Glu  Ala
               580                 585                      590

Thr  Tyr  Ser  Arg  Cys  Gly  Ser  Gly  Pro  Trp  Ile  Thr  Pro  Arg  Cys  Leu
          595                 600                      605

Val  His  Tyr  Pro  Tyr  Arg  Leu  Trp  His  Tyr  Pro  Cys  Thr  Ile  Asn  Tyr
     610                      615                 620

Thr  Leu  Phe  Lys  Val  Arg  Met  Tyr  Val  Gly  Gly  Val  Glu  His  Arg  Leu
625                      630                 635                           640

Glu  Val  Ala  Cys  Asn  Trp  Thr  Arg  Gly  Glu  Arg  Cys  Asp  Leu  Asp  Asp
               645                 650                      655

Arg  Asp  Arg  Ser  Glu  Leu  Ser  Pro  Leu  Leu  Leu  Ser  Thr  Thr  Gln  Trp
               660                 665                      670

Gln  Val  Leu  Pro  Cys  Ser  Phe  Thr  Thr  Leu  Pro  Ala  Leu  Thr  Thr  Gly
          675                 680                      685

Leu  Ile  His  Leu  His  Gln  Asn  Ile  Val  Asp  Val  Gln  Tyr  Leu  Tyr  Gly
```

```
                    690                          695                          700
Val  Gly  Ser  Ser  Ile  Val  Ser  Trp  Ala  Ile  Lys  Trp  Glu  Tyr  Val  Ile
705                      710                      715                      720

Leu  Leu  Phe  Leu  Leu  Leu  Ala  Asp  Ala  Arg  Ile  Cys  Ser  Cys  Leu  Trp
                    725                      730                          735

Met  Met  Leu  Leu  Ile  Ser  Gln  Ala  Glu  Ala  Ala  Leu  Glu  Asn  Leu  Val
                    740                      745                      750

Leu  Leu  Asn  Ala  Ala  Ser  Leu  Ala  Gly  Thr  His  Gly  Leu  Val  Ser  Phe
                755                      760                      765

Leu  Val  Phe  Phe  Cys  Phe  Ala  Trp  Tyr  Leu  Lys  Gly  Lys  Trp  Val  Pro
770                          775                      780

Gly  Val  Ala  Tyr  Ala  Phe  Tyr  Gly  Met  Trp  Pro  Phe  Leu  Leu  Leu  Leu
785                      790                      795                      800

Leu  Ala  Leu  Pro  Gln  Arg  Ala  Tyr  Ala  Leu  Asp  Thr  Glu  Met  Ala  Ala
                    805                      810                      815

Ser  Cys  Gly  Gly  Val  Val  Leu  Val  Gly  Leu  Met  Ala  Leu  Thr  Leu  Ser
                820                      825                      830

Pro  His  Tyr  Lys  Arg  Tyr  Ile  Cys  Trp  Cys  Val  Trp  Trp  Leu  Gln  Tyr
                835                      840                      845

Phe  Leu  Thr  Arg  Ala  Glu  Ala  Leu  Leu  His  Gly  Trp  Val  Pro  Pro  Leu
850                      855                      860

Asn  Val  Arg  Gly  Gly  Arg  Asp  Ala  Val  Ile  Leu  Leu  Met  Cys  Val  Val
865                      870                      875                      880

His  Pro  Ala  Leu  Val  Phe  Asp  Ile  Thr  Lys  Leu  Leu  Leu  Ala  Val  Leu
                    885                      890                      895

Gly  Pro  Leu  Trp  Ile  Leu  Gln  Thr  Ser  Leu  Leu  Lys  Val  Pro  Tyr  Phe
                900                      905                      910

Val  Arg  Val  Gln  Gly  Leu  Leu  Arg  Ile  Cys  Ala  Leu  Ala  Arg  Lys  Met
                915                      920                      925

Ala  Gly  Gly  His  Tyr  Val  Gln  Met  Val  Thr  Ile  Lys  Met  Gly  Ala  Leu
                930                      935                      940

Ala  Gly  Thr  Tyr  Val  Tyr  Asn  His  Leu  Thr  Pro  Leu  Arg  Asp  Trp  Ala
945                      950                      955                      960

His  Asn  Gly  Leu  Arg  Asp  Leu  Ala  Val  Ala  Val  Glu  Pro  Val  Val  Phe
                    965                      970                      975

Ser  Gln  Met  Glu  Thr  Lys  Leu  Ile  Thr  Trp  Gly  Ala  Asp  Thr  Ala  Ala
                980                      985                      990

Cys  Gly  Asp  Ile  Ile  Asn  Gly  Leu  Pro  Val  Ser  Ala  Arg  Arg  Gly  Arg
                    995                      1000                     1005

Glu  Ile  Leu  Leu  Gly  Pro  Ala  Asp  Gly  Met  Val  Ser  Lys  Gly  Trp  Arg
     1010                     1015                     1020

Leu  Leu  Ala  Pro  Ile  Thr  Ala  Tyr  Ala  Gln  Gln  Thr  Arg  Gly  Leu  Leu
1025                     1030                     1035                     1040

Gly  Cys  Ile  Ile  Thr  Ser  Leu  Thr  Gly  Arg  Asp  Lys  Asn  Gln  Val  Glu
                    1045                     1050                     1055

Gly  Glu  Val  Gln  Ile  Val  Ser  Thr  Ala  Ala  Gln  Thr  Phe  Leu  Ala  Thr
                1060                     1065                     1070

Cys  Ile  Asn  Gly  Val  Cys  Trp  Thr  Val  Tyr  His  Gly  Ala  Gly  Thr  Arg
                1075                     1080                     1085

Thr  Ile  Ala  Ser  Pro  Lys  Gly  Pro  Val  Ile  Gln  Met  Tyr  Thr  Asn  Val
     1090                     1095                     1100

Asp  Arg  Asp  Leu  Val  Gly  Trp  Pro  Ala  Pro  Gln  Gly  Ala  Arg  Ser  Leu
1105                     1110                     1115                     1120
```

```
Thr  Pro  Cys  Thr  Cys  Gly  Ser  Ser  Asp  Leu  Tyr  Leu  Val  Thr  Arg  His
               1125                1130                          1135

Ala  Asp  Val  Ile  Pro  Val  Arg  Arg  Arg  Gly  Asp  Ser  Arg  Gly  Ser  Leu
          1140                     1145                          1150

Leu  Ser  Pro  Arg  Pro  Ile  Ser  Tyr  Leu  Lys  Gly  Ser  Ser  Gly  Gly  Pro
     1155                          1160                          1165

Leu  Leu  Cys  Pro  Ala  Gly  His  Ala  Val  Gly  Ile  Phe  Arg  Ala  Ala  Val
     1170                     1175                          1180

Cys  Thr  Arg  Gly  Val  Ala  Lys  Ala  Val  Asp  Phe  Ile  Pro  Val  Glu  Ser
1185                1190                     1195                          1200

Leu  Glu  Thr  Thr  Met  Arg  Ser  Pro  Val  Phe  Thr  Asp  Asn  Ser  Ser  Pro
                    1205                     1210                     1215

Pro  Ala  Val  Pro  Gln  Ser  Phe  Gln  Val  Ala  His  Leu  His  Ala  Pro  Thr
               1220                     1225                     1230

Gly  Ser  Gly  Lys  Ser  Thr  Lys  Val  Pro  Ala  Ala  Tyr  Ala  Ala  Gln  Gly
          1235                     1240                     1245

Tyr  Lys  Val  Leu  Val  Leu  Asn  Pro  Ser  Val  Ala  Ala  Thr  Leu  Gly  Phe
     1250                     1255                     1260

Gly  Ala  Tyr  Met  Ser  Lys  Ala  His  Gly  Ile  Asp  Pro  Asn  Ile  Arg  Thr
1265                1270                     1275                          1280

Gly  Val  Arg  Thr  Ile  Thr  Thr  Gly  Ser  Pro  Ile  Thr  Tyr  Ser  Thr  Tyr
               1285                     1290                     1295

Gly  Lys  Phe  Leu  Ala  Asp  Gly  Gly  Cys  Ser  Gly  Gly  Ala  Tyr  Asp  Ile
               1300                     1305                     1310

Ile  Ile  Cys  Asp  Glu  Cys  His  Ser  Thr  Asp  Ala  Thr  Ser  Ile  Leu  Gly
               1315                     1320                     1325

Ile  Gly  Thr  Val  Leu  Asp  Gln  Ala  Glu  Thr  Ala  Gly  Ala  Arg  Leu  Val
     1330                     1335                     1340

Val  Leu  Ala  Thr  Ala  Thr  Pro  Pro  Gly  Ser  Val  Thr  Val  Pro  His  Pro
1345                     1350                     1355                     1360

Asn  Ile  Glu  Glu  Val  Ala  Leu  Ser  Thr  Thr  Gly  Glu  Ile  Pro  Phe  Tyr
                    1365                     1370                     1375

Gly  Lys  Ala  Ile  Pro  Leu  Glu  Ala  Ile  Lys  Gly  Gly  Arg  His  Leu  Ile
               1380                     1385                     1390

Phe  Cys  His  Ser  Lys  Lys  Lys  Cys  Asp  Glu  Leu  Ala  Ala  Lys  Leu  Val
          1395                     1400                     1405

Thr  Leu  Gly  Ile  Asn  Ala  Val  Ala  Tyr  Tyr  Arg  Gly  Leu  Asp  Val  Ser
               1410                     1415                     1420

Val  Ile  Pro  Thr  Ser  Gly  Asp  Val  Val  Val  Ala  Thr  Asp  Ala  Leu
1425                     1430                     1435                     1440

Met  Thr  Gly  Phe  Thr  Gly  Asp  Phe  Asp  Ser  Val  Ile  Asp  Cys  Asn  Thr
                    1445                     1450                     1455

Cys  Val  Thr  Gln  Ala  Val  Asp  Phe  Ser  Leu  Asp  Pro  Thr  Phe  Thr  Ile
                    1460                     1465                     1470

Glu  Thr  Thr  Thr  Leu  Pro  Gln  Asp  Ala  Val  Ser  Arg  Thr  Gln  Arg  Arg
                    1475                     1480                     1485

Gly  Arg  Thr  Gly  Arg  Gly  Lys  Pro  Gly  Ile  Tyr  Arg  Phe  Val  Ala  Pro
     1490                     1495                     1500

Gly  Glu  Arg  Pro  Ser  Gly  Met  Phe  Asp  Ser  Ser  Val  Leu  Cys  Glu  Cys
1505                     1510                     1515                     1520

Tyr  Asp  Ala  Gly  Cys  Ala  Trp  Tyr  Glu  Leu  Thr  Pro  Ala  Glu  Thr  Thr
                    1525                     1530                     1535

Val  Arg  Leu  Arg  Ala  Tyr  Met  Asn  Thr  Pro  Gly  Leu  Pro  Val  Cys  Gln
               1540                     1545                     1550
```

```
Asp His Leu Glu Phe Trp Glu Gly Val Phe Thr Gly Leu Thr His Ile
        1555                1560                1565

Asp Ala His Phe Leu Ser Gln Thr Lys Gln Ser Gly Glu Asn Leu Pro
        1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
                1605                1610                1615

Thr Leu His Gly Pro Thr Pro Leu Leu Tyr Arg Leu Gly Ala Val Gln
                1620                1625                1630

Asn Glu Val Thr Leu Thr His Pro Ile Thr Lys Tyr Ile Met Thr Cys
                1635                1640                1645

Met Ser Ala Asp Leu Glu Val Val Thr Ser Thr Trp Val Leu Val Gly
        1650                1655                1660

Gly Val Leu Ala Ala Leu Ala Ala Tyr Cys Leu Ser Thr Gly Cys Val
1665                1670                1675                1680

Val Ile Val Gly Arg Ile Val Leu Ser Gly Lys Pro Ala Ile Ile Pro
                1685                1690                1695

Asp Arg Glu Val Leu Tyr Arg Glu Phe Asp Glu Met Glu Glu Cys Ser
                1700                1705                1710

Gln His Leu Pro Tyr Ile Glu Gln Gly Met Met Leu Ala Glu Gln Phe
        1715                1720                1725

Lys Gln Lys Ala Leu Gly Leu Leu Gln Thr Ala Ser His Gln Ala Glu
        1730                1735                1740

Val Ile Ala Pro Ala Val Gln Thr Asn Trp Gln Arg Leu Glu Thr Phe
1745                1750                1755                1760

Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
        1780                1785                1790

Phe Thr Ala Ala Val Thr Ser Pro Leu Thr Thr Ser Gln Thr Leu Leu
        1795                1800                1805

Phe Asn Ile Leu Gly Gly Trp Val Ala Ala Gln Leu Ala Ala Pro Ser
        1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Val Asp Ile Leu Ala Gly Tyr Gly
                1845                1850                1855

Ala Gly Val Ala Gly Ala Leu Val Ala Phe Lys Ile Met Ser Gly Glu
                1860                1865                1870

Val Pro Ser Thr Glu Asp Leu Val Asn Leu Leu Pro Ala Ile Leu Ser
                1875                1880                1885

Pro Gly Ala Leu Val Val Gly Val Val Cys Ala Ala Ile Leu Arg Arg
        1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Gly Ser Asp Ala Ala Ala Arg Val Thr Ala Ile Leu Ser Ser Leu Thr
                1940                1945                1950

Val Thr Gln Leu Leu Arg Arg Leu His Gln Trp Val Ser Ser Glu Cys
                1955                1960                1965

Thr Thr Pro Cys Ser Gly Ser Trp Leu Arg Asp Ile Trp Asp Trp Ile
```

```
                1970                    1975                     1980
      Cys  Glu  Val  Leu  Ser  Asp  Phe  Lys  Thr  Trp  Leu  Lys  Ala  Lys  Leu  Met
      1985                    1990                    1995                     2000
      Pro  Gln  Leu  Pro  Gly  Ile  Pro  Phe  Val  Ser  Cys  Gln  Arg  Gly  Tyr  Lys
                              2005                    2010                     2015
      Gly  Val  Trp  Arg  Gly  Asp  Gly  Ile  Met  His  Thr  Arg  Cys  His  Cys  Gly
                              2020                    2025                     2030
      Ala  Glu  Ile  Ala  Gly  His  Val  Lys  Asn  Gly  Thr  Met  Arg  Ile  Val  Gly
                              2035                    2040                     2045
      Pro  Lys  Thr  Cys  Arg  Asn  Met  Trp  Ser  Gly  Thr  Phe  Pro  Ile  Asn  Ala
                              2050                    2055                     2060
      Tyr  Thr  Thr  Gly  Pro  Cys  Thr  Pro  Leu  Pro  Ala  Pro  Asn  Tyr  Lys  Phe
      2065                    2070                    2075                     2080
      Ala  Leu  Trp  Arg  Val  Ser  Ala  Glu  Glu  Tyr  Val  Glu  Ile  Arg  Gln  Val
                              2085                    2090                     2095
      Gly  Asp  Phe  His  Tyr  Val  Thr  Gly  Met  Thr  Ala  Asp  Asn  Leu  Lys  Cys
                              2100                    2105                     2110
      Pro  Cys  Gln  Val  Pro  Ser  Pro  Glu  Phe  Phe  Thr  Glu  Leu  Asp  Gly  Val
                              2115                    2120                     2125
      Arg  Leu  His  Arg  Phe  Ala  Pro  Pro  Cys  Lys  Pro  Leu  Leu  Arg  Asp  Glu
                              2130                    2135                     2140
      Val  Ser  Phe  Arg  Val  Gly  Leu  His  Asp  Tyr  Pro  Val  Gly  Ser  Gln  Leu
      2145                    2150                    2155                     2160
      Pro  Cys  Glu  Pro  Glu  Pro  Asp  Val  Ala  Val  Leu  Thr  Ser  Met  Leu  Thr
                              2165                    2170                     2175
      Asp  Pro  Ser  His  Ile  Thr  Ala  Glu  Thr  Ala  Gly  Arg  Arg  Leu  Ala  Arg
                              2180                    2185                     2190
      Gly  Ser  Pro  Pro  Ser  Met  Ala  Ser  Ser  Ser  Ala  Ser  Gln  Leu  Ser  Ala
                              2195                    2200                     2205
      Pro  Ser  Leu  Lys  Ala  Thr  Cys  Thr  Thr  Asn  His  Asp  Ser  Pro  Asp  Ala
                              2210                    2215                     2220
      Glu  Leu  Leu  Glu  Ala  Asn  Leu  Leu  Trp  Arg  Gln  Glu  Met  Gly  Gly  Asn
      2225                    2230                    2235                     2240
      Ile  Thr  Arg  Val  Glu  Ser  Glu  Asn  Lys  Val  Val  Val  Leu  Asp  Ser  Phe
                              2245                    2250                     2255
      Asp  Pro  Leu  Val  Ala  Glu  Glu  Asp  Glu  Arg  Glu  Val  Ser  Val  Pro  Ala
                              2260                    2265                     2270
      Glu  Ile  Leu  Arg  Lys  Ser  Arg  Arg  Phe  Ala  Gln  Ala  Leu  Pro  Ser  Trp
                              2275                    2280                     2285
      Ala  Arg  Pro  Asp  Tyr  Asn  Pro  Pro  Leu  Leu  Glu  Thr  Trp  Lys  Lys  Pro
                              2290                    2295                     2300
      Asp  Tyr  Glu  Pro  Pro  Val  Val  His  Gly  Cys  Pro  Leu  Pro  Pro  Pro  Gln
      2305                    2310                    2315                     2320
      Ser  Pro  Pro  Val  Pro  Pro  Pro  Arg  Lys  Lys  Arg  Thr  Val  Val  Leu  Thr
                              2325                    2330                     2335
      Glu  Ser  Thr  Val  Ser  Ser  Ala  Leu  Ala  Glu  Leu  Ala  Thr  Lys  Ser  Phe
                              2340                    2345                     2350
      Gly  Ser  Ser  Ser  Thr  Ser  Gly  Ile  Thr  Gly  Asp  Asn  Thr  Thr  Thr  Ser
                              2355                    2360                     2365
      Ser  Glu  Pro  Ala  Pro  Ser  Val  Cys  Pro  Pro  Asp  Ser  Asp  Ala  Glu  Ser
                              2370                    2375                     2380
      Tyr  Ser  Ser  Met  Pro  Pro  Leu  Glu  Gly  Glu  Pro  Gly  Asp  Pro  Asp  Leu
      2385                    2390                    2395                     2400
```

```
Ser  Asp  Gly  Ser  Trp  Ser  Thr  Val  Ser  Ser  Gly  Ala  Asp  Thr  Glu  Asp
               2405                2410                    2415

Val  Val  Cys  Cys  Ser  Met  Ser  Tyr  Ser  Trp  Thr  Gly  Ala  Leu  Ile  Thr
               2420                2425                    2430

Pro  Cys  Ala  Ala  Glu  Glu  Gln  Leu  Pro  Ile  Asn  Ala  Leu  Ser  Asn
          2435                2440                    2445

Ser  Leu  Leu  Arg  His  His  Asn  Leu  Val  Tyr  Ser  Thr  Thr  Ser  Arg  Asn
2450                    2455                    2460

Ala  Cys  Leu  Arg  Gln  Lys  Lys  Val  Thr  Phe  Asp  Arg  Leu  Gln  Val  Leu
2465                    2470                    2475                    2480

Asp  Asn  His  Tyr  Gln  Asp  Val  Leu  Lys  Glu  Val  Lys  Ala  Ala  Ala  Ser
               2485                2490                    2495

Lys  Val  Lys  Ala  Asn  Leu  Leu  Ser  Val  Glu  Glu  Ala  Cys  Ser  Leu  Thr
               2500                2505                    2510

Pro  Pro  His  Ser  Ala  Arg  Ser  Lys  Phe  Gly  Tyr  Gly  Ala  Lys  Asp  Val
               2515                2520                    2525

Arg  Cys  His  Ala  Arg  Lys  Ala  Val  Ser  His  Ile  Asn  Ser  Val  Trp  Lys
          2530                2535                    2540

Asp  Leu  Leu  Glu  Asp  Ser  Val  Thr  Pro  Ile  Asp  Thr  Thr  Ile  Met  Ala
2545                    2550                    2555                    2560

Lys  Asn  Glu  Val  Phe  Cys  Val  Gln  Pro  Glu  Lys  Gly  Gly  Arg  Lys  Pro
                    2565                2570                    2575

Ala  Arg  Leu  Ile  Val  Phe  Pro  Asp  Leu  Gly  Val  Arg  Val  Cys  Glu  Lys
               2580                2585                    2590

Met  Ala  Leu  Tyr  Asp  Val  Val  Ser  Lys  Leu  Pro  Leu  Ala  Val  Met  Gly
          2595                2600                    2605

Ser  Ser  Tyr  Gly  Phe  Gln  Tyr  Ser  Pro  Gly  Gln  Arg  Val  Glu  Phe  Leu
          2610                2615                    2620

Val  Gln  Ala  Trp  Lys  Ser  Lys  Lys  Thr  Pro  Met  Gly  Phe  Ser  Tyr  Asp
2625                    2630                    2635                    2640

Thr  Arg  Cys  Phe  Asp  Ser  Thr  Val  Thr  Glu  Ser  Asp  Ile  Arg  Thr  Glu
               2645                2650                    2655

Glu  Ala  Ile  Tyr  Gln  Cys  Cys  Asp  Leu  Asp  Pro  Gln  Ala  Arg  Val  Ala
               2660                2665                    2670

Ile  Lys  Ser  Leu  Thr  Glu  Arg  Leu  Tyr  Val  Gly  Gly  Pro  Leu  Thr  Asn
          2675                2680                    2685

Ser  Arg  Gly  Glu  Asn  Cys  Gly  Tyr  Arg  Arg  Cys  Arg  Ala  Ser  Gly  Val
          2690                2695                    2700

Leu  Thr  Thr  Ser  Cys  Gly  Asn  Thr  Leu  Thr  Cys  Tyr  Ile  Lys  Ala  Arg
2705                    2710                    2715                    2720

Ala  Ala  Cys  Arg  Ala  Ala  Gly  Leu  Gln  Asp  Cys  Thr  Met  Leu  Val  Cys
               2725                2730                    2735

Gly  Asp  Asp  Leu  Val  Val  Ile  Cys  Glu  Ser  Gln  Gly  Val  Gln  Glu  Asp
               2740                2745                    2750

Ala  Ala  Ser  Leu  Arg  Ala  Phe  Thr  Glu  Ala  Met  Thr  Arg  Tyr  Ser  Ala
               2755                2760                    2765

Pro  Pro  Gly  Asp  Pro  Pro  Gln  Pro  Glu  Tyr  Asp  Leu  Glu  Leu  Ile  Thr
               2770                2775                    2780

Pro  Cys  Ser  Ser  Asn  Val  Ser  Val  Ala  His  Asp  Gly  Ala  Gly  Lys  Arg
2785                    2790                    2795                    2800

Val  Tyr  Tyr  Leu  Thr  Arg  Asp  Pro  Thr  Thr  Pro  Leu  Ala  Arg  Ala  Ala
               2805                2810                    2815

Trp  Glu  Thr  Ala  Arg  His  Thr  Pro  Val  Asn  Ser  Trp  Leu  Gly  Asn  Ile
               2820                2825                    2830
```

| | | | | | | | | | | | | | | |
|---|---|---|---|---|---|---|---|---|---|---|---|---|---|---|
|Ile|Met|Phe|Ala|Pro|Thr|Leu|Trp|Ala|Arg|Met|Ile|Leu|Met|Thr|His|
| |2835| | | | |2840| | | | |2845| | | |

| | | | | | | | | | | | | | | |
|---|---|---|---|---|---|---|---|---|---|---|---|---|---|---|
|Phe|Phe|Ser|Val|Leu|Ile|Ala|Arg|Asp|Gln|Leu|Glu|Gln|Ala|Leu|Asp|
| |2850| | | | |2855| | | | |2860| | | |

| | | | | | | | | | | | | | | |
|---|---|---|---|---|---|---|---|---|---|---|---|---|---|---|
|Cys|Glu|Ile|Tyr|Gly|Ala|Cys|Tyr|Ser|Ile|Glu|Pro|Leu|Asp|Leu|Pro|
|2865| | | |2870| | | |2875| | | |2880| | | |

| | | | | | | | | | | | | | | |
|---|---|---|---|---|---|---|---|---|---|---|---|---|---|---|
|Pro|Ile|Ile|Gln|Arg|Leu|His|Gly|Leu|Ser|Ala|Phe|Ser|Leu|His|Ser|
| | | |2885| | | |2890| | | | |2895| | |

| | | | | | | | | | | | | | | |
|---|---|---|---|---|---|---|---|---|---|---|---|---|---|---|
|Tyr|Ser|Pro|Gly|Glu|Ile|Asn|Arg|Val|Ala|Ala|Cys|Leu|Arg|Lys|Leu|
| | |2900| | | | |2905| | | | |2910| | |

| | | | | | | | | | | | | | | |
|---|---|---|---|---|---|---|---|---|---|---|---|---|---|---|
|Gly|Val|Pro|Pro|Leu|Arg|Ala|Trp|Arg|His|Arg|Ala|Arg|Ser|Val|Arg|
| |2915| | | | |2920| | | | |2925| | | |

| | | | | | | | | | | | | | | |
|---|---|---|---|---|---|---|---|---|---|---|---|---|---|---|
|Ala|Arg|Leu|Leu|Ser|Arg|Gly|Gly|Arg|Ala|Ala|Ile|Cys|Gly|Lys|Tyr|
|2930| | | | |2935| | | | |2940| | | | |

| | | | | | | | | | | | | | | |
|---|---|---|---|---|---|---|---|---|---|---|---|---|---|---|
|Leu|Phe|Asn|Trp|Ala|Val|Arg|Thr|Lys|Leu|Lys|Leu|Thr|Pro|Ile|Ala|
|2945| | | | |2950| | | | |2955| | | |2960|

| | | | | | | | | | | | | | | |
|---|---|---|---|---|---|---|---|---|---|---|---|---|---|---|
|Ala|Ala|Gly|Gln|Leu|Asp|Leu|Ser|Gly|Trp|Phe|Thr|Ala|Gly|Tyr|Gly|
| | | |2965| | | |2970| | | | |2975| | |

| | | | | | | | | | | | | | | |
|---|---|---|---|---|---|---|---|---|---|---|---|---|---|---|
|Gly|Gly|Asp|Ile|Tyr|His|Ser|Val|Ser|Arg|Ala|Arg|Pro|Arg|Trp|Phe|
| | |2980| | | | |2985| | | | |2990| | |

| | | | | | | | | | | | | | | |
|---|---|---|---|---|---|---|---|---|---|---|---|---|---|---|
|Trp|Phe|Cys|Leu|Leu|Leu|Leu|Ala|Ala|Gly|Val|Gly|Ile|Tyr|Leu|Leu|
| |2995| | | | |3000| | | | |3005| | | |

| | |
|---|---|
|Pro|Asn|Arg|
|3010|

(2) INFORMATION FOR SEQ ID NO:3:

(i) SEQUENCE CHARACTERISTICS:
    (A) LENGTH: 7298 base pairs
    (B) TYPE: nucleic acid
    (C) STRANDEDNESS: single
    (D) TOPOLOGY: circular (ii) MOLECULE TYPE: DNA (genomic)

(ix) FEATURE:
    (A) NAME/KEY: CDS
    (B) LOCATION: 922..2532

(xi) SEQUENCE DESCRIPTION: SEQ ID NO:3:

```
GACGGATCGG GAGATCTCCC GATCCCCTAT GGTCGACTCT CAGTACAATC TGCTCTGATG        60
CCGCATAGTT AAGCCAGTAT CTGCTCCCTG CTTGTGTGTT GGAGGTCGCT GAGTAGTGCG       120
CGAGCAAAAT TTAAGCTACA ACAAGGCAAG GCTTGACCGA CAATTGCATG AAGAATCTGC       180
TTAGGGTTAG GCGTTTTGCG CTGCTTCGCG ATGTACGGGC CAGATATACG CGTTGACATT       240
GATTATTGAC TAGTTATTAA TAGTAATCAA TTACGGGGTC ATTAGTTCAT AGCCCATATA       300
TGGAGTTCCG CGTTACATAA CTTACGGTAA ATGGCCCGCC TGGCTGACCG CCCAACGACC       360
CCCGCCCATT GACGTCAATA ATGACGTATG TTCCATAGT AACGCCAATA GGGACTTTCC       420
ATTGACGTCA ATGGGTGGAC TATTTACGGT AAACTGCCCA CTTGGCAGTA CATCAAGTGT       480
ATCATATGCC AAGTACGCCC CCTATTGACG TCAATGACGG TAAATGGCCC GCCTGGCATT       540
ATGCCCAGTA CATGACCTTA TGGGACTTTC CTACTTGGCA GTACATCTAC GTATTAGTCA       600
TCGCTATTAC CATGGTGATG CGGTTTTGGC AGTACATCAA TGGGCGTGGA TAGCGGTTTG       660
ACTCACGGGG ATTTCCAAGT CTCCACCCCA TTGACGTCAA TGGGAGTTTG TTTTGGCACC       720
AAAATCAACG GGACTTTCCA AAATGTCGTA ACAACTCCGC CCCATTGACG CAAATGGGCG       780
```

-continued

```
GTAGGCGTGT ACGGTGGGAG GTCTATATAA GCAGAGCTCT CTGGCTAACT AGAGAACCCA      840

CTGCTTAACT GGCTTATCGA AATTAATACG ACTCACTATA GGGAGACCGG AAGCTTTGCT      900

CTAGACTGGA ATTCGGGCGC G ATG CTG CCC GGT TTG GCA CTG CTC CTG CTG       951
             Met Leu Pro Gly Leu Ala Leu Leu Leu Leu
              1           5                    10

GCC GCC TGG ACG GCT CGG GCG CTG GAG GTA CCC ACT GAT GGT AAT GCT       999
Ala Ala Trp Thr Ala Arg Ala Leu Glu Val Pro Thr Asp Gly Asn Ala
             15                20                    25

GGC CTG CTG GCT GAA CCC CAG ATT GCC ATG TTC TGT GGC AGA CTG AAC      1047
Gly Leu Leu Ala Glu Pro Gln Ile Ala Met Phe Cys Gly Arg Leu Asn
         30                    35                    40

ATG CAC ATG AAT GTC CAG AAT GGG AAG TGG GAT TCA GAT CCA TCA GGG      1095
Met His Met Asn Val Gln Asn Gly Lys Trp Asp Ser Asp Pro Ser Gly
             45                50                    55

ACC AAA ACC TGC ATT GAT ACC AAG GAA ACC CAC GTC ACC GGG GGA AGT      1143
Thr Lys Thr Cys Ile Asp Thr Lys Glu Thr His Val Thr Gly Gly Ser
         60                    65                    70

GCC GGC CAC ACC ACG GCT GGG CTT GTT CGT CTC CTT TCA CCA GGC GCC      1191
Ala Gly His Thr Thr Ala Gly Leu Val Arg Leu Leu Ser Pro Gly Ala
 75              80                    85                    90

AAG CAG AAC ATC CAA CTG ATC AAC ACC AAC GGC AGT TGG CAC ATC AAT      1239
Lys Gln Asn Ile Gln Leu Ile Asn Thr Asn Gly Ser Trp His Ile Asn
                 95                   100                   105

AGC ACG GCC TTG AAC TGC AAT GAA AGC CTT AAC ACC GGC TGG TTA GCA      1287
Ser Thr Ala Leu Asn Cys Asn Glu Ser Leu Asn Thr Gly Trp Leu Ala
             110                   115                   120

GGG CTC TTC TAT CAC CAC AAA TTC AAC TCT TCA GGT TGT CCT GAG AGG      1335
Gly Leu Phe Tyr His His Lys Phe Asn Ser Ser Gly Cys Pro Glu Arg
             125                   130                   135

TTG GCC AGC TGC CGA CGC CTT ACC GAT TTT GCC CAG GGC GGG GGT CCT      1383
Leu Ala Ser Cys Arg Arg Leu Thr Asp Phe Ala Gln Gly Gly Gly Pro
         140                   145                   150

ATC AGT TAC GCC AAC GGA AGC GGC CTC GAT GAA CGC CCC TAC TGC TGG      1431
Ile Ser Tyr Ala Asn Gly Ser Gly Leu Asp Glu Arg Pro Tyr Cys Trp
155              160                   165                   170

CAC TAC CCT CCA AGA CCT TGT GGC ATT GTG CCC GCA AAG AGC GTG TGT      1479
His Tyr Pro Pro Arg Pro Cys Gly Ile Val Pro Ala Lys Ser Val Cys
                 175                   180                   185

GGC CCG GTA TAT TGC TTC ACT CCC AGC CCC GTG GTG GTG GGA ACG ACC      1527
Gly Pro Val Tyr Cys Phe Thr Pro Ser Pro Val Val Val Gly Thr Thr
             190                   195                   200

GAC AGG TCG GGC GCG CCT ACC TAC AGC TGG GGT GCA AAT GAT ACG GAT      1575
Asp Arg Ser Gly Ala Pro Thr Tyr Ser Trp Gly Ala Asn Asp Thr Asp
         205                   210                   215

GTC TTT GTC CTT AAC AAC ACC AGG CCA CCG CTG GGC AAT TGG TTC GGT      1623
Val Phe Val Leu Asn Asn Thr Arg Pro Pro Leu Gly Asn Trp Phe Gly
         220                   225                   230

TGC ACC TGG ATG AAC TCA ACT GGA TTC ACC AAA GTG TGC GGA GCG CCC      1671
Cys Thr Trp Met Asn Ser Thr Gly Phe Thr Lys Val Cys Gly Ala Pro
235                   240                   245                   250

CCT TGT GTC ATC GGA GGG GTG GGC AAC AAC ACC TTG CTC TGC CCC ACT      1719
Pro Cys Val Ile Gly Gly Val Gly Asn Asn Thr Leu Leu Cys Pro Thr
             255                   260                   265

GAT TGC TTC CGC AAG CAT CCG GAA GCC ACA TAC TCT CGG TGC GGC TCC      1767
Asp Cys Phe Arg Lys His Pro Glu Ala Thr Tyr Ser Arg Cys Gly Ser
             270                   275                   280

GGT CCC TGG ATT ACA CCC AGG TGC ATG GTC GAC TAC CCG TAT AGG CTT      1815
Gly Pro Trp Ile Thr Pro Arg Cys Met Val Asp Tyr Pro Tyr Arg Leu
         285                   290                   295
```

| | | | | | | | | | | | | | | | | |
|---|---|---|---|---|---|---|---|---|---|---|---|---|---|---|---|---|
| TGG | CAC | TAT | CCT | TGT | ACC | ATC | AAT | TAC | ACC | ATA | TTC | AAA | GTC | AGG | ATG | 1863 |
| Trp | His | Tyr | Pro | Cys | Thr | Ile | Asn | Tyr | Thr | Ile | Phe | Lys | Val | Arg | Met | |
| | 300 | | | | 305 | | | | | 310 | | | | | | |
| TAC | GTG | GGA | GGG | GTC | GAG | CAC | AGG | CTG | GAA | GCG | GCC | TGC | AAC | TGG | ACG | 1911 |
| Tyr | Val | Gly | Gly | Val | Glu | His | Arg | Leu | Glu | Ala | Ala | Cys | Asn | Trp | Thr | |
| 315 | | | | | 320 | | | | | 325 | | | | | 330 | |
| CGG | GGC | GAA | CGC | TGT | GAT | CTG | GAA | GAC | AGG | GAC | AGG | TCC | GAG | CTC | AGC | 1959 |
| Arg | Gly | Glu | Arg | Cys | Asp | Leu | Glu | Asp | Arg | Asp | Arg | Ser | Glu | Leu | Ser | |
| | | | | 335 | | | | | 340 | | | | | 345 | | |
| CCG | TTA | CTG | CTG | TCC | ACC | ACG | CAG | TGG | CAG | GTC | CTT | CCG | TGT | TCT | TTC | 2007 |
| Pro | Leu | Leu | Leu | Ser | Thr | Thr | Gln | Trp | Gln | Val | Leu | Pro | Cys | Ser | Phe | |
| | | | 350 | | | | | 355 | | | | | 360 | | | |
| ACG | ACC | CTG | CCA | GCC | TTG | TCC | ACC | GGC | CTC | ATC | CAC | CTC | CAC | CAG | AAC | 2055 |
| Thr | Thr | Leu | Pro | Ala | Leu | Ser | Thr | Gly | Leu | Ile | His | Leu | His | Gln | Asn | |
| | | 365 | | | | | 370 | | | | | 375 | | | | |
| ATT | GTG | GAC | GTG | CAG | TAC | TTG | TAC | GGG | GTA | GGG | TCA | AGC | ATC | GCG | TCC | 2103 |
| Ile | Val | Asp | Val | Gln | Tyr | Leu | Tyr | Gly | Val | Gly | Ser | Ser | Ile | Ala | Ser | |
| | 380 | | | | | 385 | | | | | 390 | | | | | |
| TGG | GCT | ATT | AAG | TGG | GAG | TAC | GAC | GTT | CTC | CTG | TTC | CTT | CTG | CTT | GCA | 2151 |
| Trp | Ala | Ile | Lys | Trp | Glu | Tyr | Asp | Val | Leu | Leu | Phe | Leu | Leu | Leu | Ala | |
| 395 | | | | | 400 | | | | | 405 | | | | | 410 | |
| GAC | GCG | CGC | GTT | TGC | TCC | TGC | TTG | TGG | ATG | ATG | TTA | CTC | ATA | TCC | CAA | 2199 |
| Asp | Ala | Arg | Val | Cys | Ser | Cys | Leu | Trp | Met | Met | Leu | Leu | Ile | Ser | Gln | |
| | | | | 415 | | | | | 420 | | | | | 425 | | |
| GCG | GAG | GCG | GCT | TTG | GAG | ATC | TCT | GAA | GTG | AAG | ATG | GAT | GCA | GAA | TTC | 2247 |
| Ala | Glu | Ala | Ala | Leu | Glu | Ile | Ser | Glu | Val | Lys | Met | Asp | Ala | Glu | Phe | |
| | | | 430 | | | | | 435 | | | | | 440 | | | |
| CGA | CAT | GAC | TCA | GGA | TAT | GAA | GTT | CAT | CAT | CAA | AAA | TTG | GTG | TTC | TTT | 2295 |
| Arg | His | Asp | Ser | Gly | Tyr | Glu | Val | His | His | Gln | Lys | Leu | Val | Phe | Phe | |
| | | 445 | | | | | 450 | | | | | 455 | | | | |
| GCA | GAA | GAT | GTG | GGT | TCA | AAC | AAA | GGT | GCA | ATT | ATT | GGA | CTC | ATG | GTG | 2343 |
| Ala | Glu | Asp | Val | Gly | Ser | Asn | Lys | Gly | Ala | Ile | Ile | Gly | Leu | Met | Val | |
| | 460 | | | | | 465 | | | | | 470 | | | | | |
| GGC | GGT | GTT | GTC | ATA | GCG | ACA | GTG | ATC | GTC | ATC | ACC | TTG | GTG | ATG | CTG | 2391 |
| Gly | Gly | Val | Val | Ile | Ala | Thr | Val | Ile | Val | Ile | Thr | Leu | Val | Met | Leu | |
| 475 | | | | | 480 | | | | | 485 | | | | | 490 | |
| AAG | AAG | AAA | CAG | TAC | ACA | TCC | ATT | CAT | CAT | GGT | GTG | GTG | GAG | GTT | GAC | 2439 |
| Lys | Lys | Lys | Gln | Tyr | Thr | Ser | Ile | His | His | Gly | Val | Val | Glu | Val | Asp | |
| | | | | 495 | | | | | 500 | | | | | 505 | | |
| GCC | GCT | GTC | ACC | CCA | GAG | GAG | CGC | CAC | CTG | TCC | AAG | ATG | CAG | CAG | AAC | 2487 |
| Ala | Ala | Val | Thr | Pro | Glu | Glu | Arg | His | Leu | Ser | Lys | Met | Gln | Gln | Asn | |
| | | | 510 | | | | | 515 | | | | | 520 | | | |
| GGC | TAC | GAA | AAT | CCA | ACC | TAC | AAG | TTC | TTT | GAG | CAG | ATG | CAG | AAC | | 2532 |
| Gly | Tyr | Glu | Asn | Pro | Thr | Tyr | Lys | Phe | Phe | Glu | Gln | Met | Gln | Asn | | |
| | | 525 | | | | | 530 | | | | | 535 | | | | |

| | | | | | |
|---|---|---|---|---|---|
| TAGACCCCCG | CCACAGCAGC | CTCTGAAGTT | GGACAGCAAA | ACCATTGCTT | CACTACCCAT | 2592 |
| CGGTGTCCAT | TTATAGAATA | ATGTGGGAAG | AAACAAACCC | GTTTTATGAT | TTACTCATTA | 2652 |
| TCGCCTTTTG | ACAGCTGTGC | TGTAACACAA | GTAGATGCCT | GAACTTGAAT | TAATCCACAC | 2712 |
| ATCAGTATTG | TATTCTATCT | CTCTTTACAT | TTTGGTCTCT | ATACTACATT | ATTAATGGGT | 2772 |
| TTTGTGTACT | GTAAAGAATT | TAGCTGTATC | AAACTAGTGC | ATGAATAGGC | CGCTCGAGCA | 2832 |
| TGCATCTAGA | GGGCCCTATT | CTATAGTGTC | ACCTAAATGC | TCGCTGATCA | GCCTCGACTG | 2892 |
| TGCCTTCTAG | TTGCCAGCCA | TCTGTTGTTT | GCCCCTCCCC | CGTGCCTTCC | TTGACCCTGG | 2952 |
| AAGGTGCCAC | TCCCACTGTC | CTTTCCTAAT | AAAATGAGGA | AATTGCATCG | CATTGTCTGA | 3012 |
| GTAGGTGTCA | TTCTATTCTG | GGGGGTGGGG | TGGGGCAGGA | CAGCAAGGGG | GAGGATTGGG | 3072 |
| AAGACAATAG | CAGGCATGCT | GGGGATGCGG | TGGGCTCTAT | GGAACCAGCT | GGGGCTCGAG | 3132 |

| | | | | | | |
|---|---|---|---|---|---|---|
| GGGGGATCCC | CACGCGCCCT | GTAGCGGCGC | ATTAAGCGCG | GCGGGTGTGG | TGGTTACGCG | 3192 |
| CAGCGTGACC | GCTACACTTG | CCAGCGCCCT | AGCGCCCGCT | CCTTTCGCTT | TCTTCCCTTC | 3252 |
| CTTTCTCGCC | ACGTTCGCCG | GCTTTCCCCG | TCAAGCTCTA | AATCGGGGCA | TCCCTTTAGG | 3312 |
| GTTCCGATTT | AGTGCTTTAC | GGCACCTCGA | CCCCAAAAAA | CTTGATTAGG | GTGATGGTTC | 3372 |
| ACGTAGTGGG | CCATCGCCCT | GATAGACGGT | TTTTCGCCTT | TACTGAGCAC | TCTTTAATAG | 3432 |
| TGGACTCTTG | TTCCAAACTG | GAACAACACT | CAACCCTATC | TCGGTCTATT | CTTTTGATTT | 3492 |
| ATAAGATTTC | CATCGCCATG | TAAAAGTGTT | ACAATTAGCA | TTAAATTACT | TCTTTATATG | 3552 |
| CTACTATTCT | TTTGGCTTCG | TTCACGGGGT | GGGTACCGAG | CTCGAATTCT | GTGGAATGTG | 3612 |
| TGTCAGTTAG | GGTGTGGAAA | GTCCCCAGGC | TCCCCAGGCA | GGCAGAAGTA | TGCAAAGCAT | 3672 |
| GCATCTCAAT | TAGTCAGCAA | CCAGGTGTGG | AAAGTCCCCA | GGCTCCCCAG | CAGGCAGAAG | 3732 |
| TATGCAAAGC | ATGCATCTCA | ATTAGTCAGC | AACCATAGTC | CCGCCCCTAA | CTCCGCCCAT | 3792 |
| CCCGCCCCTA | ACTCCGCCCA | GTTCCGCCCA | TTCTCCGCCC | CATGGCTGAC | TAATTTTTTT | 3852 |
| TATTTATGCA | GAGGCCGAGG | CCGCCTCGGC | CTCTGAGCTA | TTCCAGAAGT | AGTGAGGAGG | 3912 |
| CTTTTTTGGA | GGCCTAGGCT | TTTGCAAAAA | GCTCCGGGA | GCTTGGATAT | CCATTTTCGG | 3972 |
| ATCTGATCAA | GAGACAGGAT | GAGGATCGTT | TCGCATGATT | GAACAAGATG | GATTGCACGC | 4032 |
| AGGTTCTCCG | GCCGCTTGGG | TGGAGAGGCT | ATTCGGCTAT | GACTGGGCAC | AACAGACAAT | 4092 |
| CGGCTGCTCT | GATGCCGCCG | TGTTCCGGCT | GTCAGCGCAG | GGGCGCCCGG | TTCTTTTTGT | 4152 |
| CAAGACCGAC | CTGTCCGGTG | CCCTGAATGA | ACTGCAGGAC | GAGGCAGCGC | GGCTATCGTG | 4212 |
| GCTGGCCACG | ACGGGCGTTC | CTTGCGCAGC | TGTGCTCGAC | GTTGTCACTG | AAGCGGGAAG | 4272 |
| GGACTGGCTG | CTATTGGGCG | AAGTGCCGGG | GCAGGATCTC | CTGTCATCTC | ACCTTGCTCC | 4332 |
| TGCCGAGAAA | GTATCCATCA | TGGCTGATGC | AATGCGGCGG | CTGCATACGC | TTGATCCGGC | 4392 |
| TACCTGCCCA | TTCGACCACC | AAGCGAAACA | TCGCATCGAG | CGAGCACGTA | CTCGGATGGA | 4452 |
| AGCCGGTCTT | GTCGATCAGG | ATGATCTGGA | CGAAGAGCAT | CAGGGGCTCG | CGCCAGCCGA | 4512 |
| ACTGTTCGCC | AGGCTCAAGG | CGCGCATGCC | CGACGGCGAG | GATCTCGTCG | TGACCCATGG | 4572 |
| CGATGCCTGC | TTGCCGAATA | TCATGGTGGA | AAATGGCCGC | TTTTCTGGAT | TCATCGACTG | 4632 |
| TGGCCGGCTG | GGTGTGGCGG | ACCGCTATCA | GGACATAGCG | TTGGCTACCC | GTGATATTGC | 4692 |
| TGAAGAGCTT | GGCGGCGAAT | GGGCTGACCG | CTTCCTCGTG | CTTTACGGTA | TCGCCGCTCC | 4752 |
| CGATTCGCAG | CGCATCGCCT | TCTATCGCCT | TCTTGACGAG | TTCTTCTGAG | CGGGACTCTG | 4812 |
| GGGTTCGAAA | TGACCGACCA | AGCGACGCCC | AACCTGCCAT | CACGAGATTT | CGATTCCACC | 4872 |
| GCCGCCTTCT | ATGAAAGGTT | GGGCTTCGGA | ATCGTTTTCC | GGGACGCCGG | CTGGATGATC | 4932 |
| CTCCAGCGCG | GGGATCTCAT | GCTGGAGTTC | TTCGCCCACC | CCAACTTGTT | TATTGCAGCT | 4992 |
| TATAATGGTT | ACAAATAAAG | CAATAGCATC | ACAAATTTCA | CAAATAAAGC | ATTTTTTCA | 5052 |
| CTGCATTCTA | GTTGTGGTTT | GTCCAAACTC | ATCAATGTAT | CTTATCATGT | CTGGATCCCG | 5112 |
| TCGACCTCGA | GAGCTTGGCG | TAATCATGGT | CATAGCTGTT | TCCTGTGTGA | AATTGTTATC | 5172 |
| CGCTCACAAT | TCCACACAAC | ATACGAGCCG | GAAGCATAAA | GTGTAAAGCC | TGGGGTGCCT | 5232 |
| AATGAGTGAG | CTAACTCACA | TTAATTGCGT | TGCGCTCACT | GCCCGCTTTC | CAGTCGGGAA | 5292 |
| ACCTGTCGTG | CCAGCTGCAT | TAATGAATCG | GCCAACGCGC | GGGGAGAGGC | GGTTTGCGTA | 5352 |
| TTGGGCGCTC | TTCCGCTTCC | TCGCTCACTG | ACTCGCTGCG | CTCGGTCGTT | CGGCTGCGGC | 5412 |
| GAGCGGTATC | AGCTCACTCA | AAGGCGGTAA | TACGGTTATC | CACAGAATCA | GGGGATAACG | 5472 |
| CAGGAAAGAA | CATGTGAGCA | AAAGGCCAGC | AAAAGGCCAG | GAACCGTAAA | AAGGCCGCGT | 5532 |

| | | | | | |
|---|---|---|---|---|---|
| TGCTGGCGTT | TTTCCATAGG | CTCCGCCCCC | CTGACGAGCA | TCACAAAAAT | CGACGCTCAA | 5592
| GTCAGAGGTG | GCGAAACCCG | ACAGGACTAT | AAAGATACCA | GGCGTTTCCC | CCTGGAAGCT | 5652
| CCCTCGTGCG | CTCTCCTGTT | CCGACCCTGC | CGCTTACCGG | ATACCTGTCC | GCCTTTCTCC | 5712
| CTTCGGGAAG | CGTGGCGCTT | TCTCAATGCT | CACGCTGTAG | GTATCTCAGT | TCGGTGTAGG | 5772
| TCGTTCGCTC | CAAGCTGGGC | TGTGTGCACG | AACCCCCGT | TCAGCCCGAC | CGCTGCGCCT | 5832
| TATCCGGTAA | CTATCGTCTT | GAGTCCAACC | CGGTAAGACA | CGACTTATCG | CCACTGGCAG | 5892
| CAGCCACTGG | TAACAGGATT | AGCAGAGCGA | GGTATGTAGG | CGGTGCTACA | GAGTTCTTGA | 5952
| AGTGGTGGCC | TAACTACGGC | TACACTAGAA | GGACAGTATT | TGGTATCTGC | GCTCTGCTGA | 6012
| AGCCAGTTAC | CTTCGGAAAA | AGAGTTGGTA | GCTCTTGATC | CGGCAAACAA | ACCACCGCTG | 6072
| GTAGCGGTGG | TTTTTTTGTT | TGCAAGCAGC | AGATTACGCG | CAGAAAAAAA | GGATCTCAAG | 6132
| AAGATCCTTT | GATCTTTTCT | ACGGGGTCTG | ACGCTCAGTG | GAACGAAAAC | TCACGTTAAG | 6192
| GGATTTTGGT | CATGAGATTA | TCAAAAAGGA | TCTTCACCTA | GATCCTTTTA | AATTAAAAAT | 6252
| GAAGTTTTAA | ATCAATCTAA | AGTATATATG | AGTAAACTTG | GTCTGACAGT | TACCAATGCT | 6312
| TAATCAGTGA | GGCACCTATC | TCAGCGATCT | GTCTATTTCG | TTCATCCATA | GTTGCCTGAC | 6372
| TCCCCGTCGT | GTAGATAACT | ACGATACGGG | AGGGCTTACC | ATCTGGCCCC | AGTGCTGCAA | 6432
| TGATACCGCG | AGACCCACGC | TCACCGGCTC | CAGATTTATC | AGCAATAAAC | CAGCCAGCCG | 6492
| GAAGGGCCGA | GCGCAGAAGT | GGTCCTGCAA | CTTTATCCGC | CTCCATCCAG | TCTATTAATT | 6552
| GTTGCCGGGA | AGCTAGAGTA | AGTAGTTCGC | CAGTTAATAG | TTTGCGCAAC | GTTGTTGCCA | 6612
| TTGCTACAGG | CATCGTGGTG | TCACGCTCGT | CGTTTGGTAT | GGCTTCATTC | AGCTCCGGTT | 6672
| CCCAACGATC | AAGGCGAGTT | ACATGATCCC | CCATGTTGTG | CAAAAAAGCG | GTTAGCTCCT | 6732
| TCGGTCCTCC | GATCGTTGTC | AGAAGTAAGT | TGGCCGCAGT | GTTATCACTC | ATGGTTATGG | 6792
| CAGCACTGCA | TAATTCTCTT | ACTGTCATGC | CATCCGTAAG | ATGCTTTTCT | GTGACTGGTG | 6852
| AGTACTCAAC | CAAGTCATTC | TGAGAATAGT | GTATGCGGCG | ACCGAGTTGC | TCTTGCCCGG | 6912
| CGTCAATACG | GGATAATACC | GCGCCACATA | GCAGAACTTT | AAAAGTGCTC | ATCATTGGAA | 6972
| AACGTTCTTC | GGGGCGAAAA | CTCTCAAGGA | TCTTACCGCT | GTTGAGATCC | AGTTCGATGT | 7032
| AACCCACTCG | TGCACCCAAC | TGATCTTCAG | CATCTTTTAC | TTTCACCAGC | GTTTCTGGGT | 7092
| GAGCAAAAAC | AGGAAGGCAA | AATGCCGCAA | AAAAGGGAAT | AAGGGCGACA | CGGAAATGTT | 7152
| GAATACTCAT | ACTCTTCCTT | TTTCAATATT | ATTGAAGCAT | TTATCAGGGT | TATTGTCTCA | 7212
| TGAGCGGATA | CATATTTGAA | TGTATTTAGA | AAAATAAACA | AATAGGGGTT | CCGCGCACAT | 7272
| TTCCCCGAAA | AGTGCCACCT | GACGTC | | | | 7298

( 2 ) INFORMATION FOR SEQ ID NO:4:

( i ) SEQUENCE CHARACTERISTICS:
        ( A ) LENGTH: 537 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45
```

```
Asn  Gly  Lys  Trp  Asp  Ser  Asp  Pro  Ser  Gly  Thr  Lys  Thr  Cys  Ile  Asp
          50                       55                       60
Thr  Lys  Glu  Thr  His  Val  Thr  Gly  Gly  Ser  Ala  Gly  His  Thr  Thr  Ala
 65                       70                       75                       80
Gly  Leu  Val  Arg  Leu  Leu  Ser  Pro  Gly  Ala  Lys  Gln  Asn  Ile  Gln  Leu
                    85                       90                       95
Ile  Asn  Thr  Asn  Gly  Ser  Trp  His  Ile  Asn  Ser  Thr  Ala  Leu  Asn  Cys
               100                      105                      110
Asn  Glu  Ser  Leu  Asn  Thr  Gly  Trp  Leu  Ala  Gly  Leu  Phe  Tyr  His  His
          115                      120                      125
Lys  Phe  Asn  Ser  Ser  Gly  Cys  Pro  Glu  Arg  Leu  Ala  Ser  Cys  Arg  Arg
     130                      135                      140
Leu  Thr  Asp  Phe  Ala  Gln  Gly  Gly  Gly  Pro  Ile  Ser  Tyr  Ala  Asn  Gly
145                      150                      155                      160
Ser  Gly  Leu  Asp  Glu  Arg  Pro  Tyr  Cys  Trp  His  Tyr  Pro  Pro  Arg  Pro
                    165                      170                      175
Cys  Gly  Ile  Val  Pro  Ala  Lys  Ser  Val  Cys  Gly  Pro  Val  Tyr  Cys  Phe
               180                      185                      190
Thr  Pro  Ser  Pro  Val  Val  Val  Gly  Thr  Thr  Asp  Arg  Ser  Gly  Ala  Pro
          195                      200                      205
Thr  Tyr  Ser  Trp  Gly  Ala  Asn  Asp  Thr  Asp  Val  Phe  Val  Leu  Asn  Asn
     210                      215                      220
Thr  Arg  Pro  Pro  Leu  Gly  Asn  Trp  Phe  Gly  Cys  Thr  Trp  Met  Asn  Ser
225                      230                      235                      240
Thr  Gly  Phe  Thr  Lys  Val  Cys  Gly  Ala  Pro  Pro  Cys  Val  Ile  Gly  Gly
                    245                      250                      255
Val  Gly  Asn  Asn  Thr  Leu  Leu  Cys  Pro  Thr  Asp  Cys  Phe  Arg  Lys  His
               260                      265                      270
Pro  Glu  Ala  Thr  Tyr  Ser  Arg  Cys  Gly  Ser  Gly  Pro  Trp  Ile  Thr  Pro
          275                      280                      285
Arg  Cys  Met  Val  Asp  Tyr  Pro  Tyr  Arg  Leu  Trp  His  Tyr  Pro  Cys  Thr
     290                      295                      300
Ile  Asn  Tyr  Thr  Ile  Phe  Lys  Val  Arg  Met  Tyr  Val  Gly  Gly  Val  Glu
305                      310                      315                      320
His  Arg  Leu  Glu  Ala  Ala  Cys  Asn  Trp  Thr  Arg  Gly  Glu  Arg  Cys  Asp
                    325                      330                      335
Leu  Glu  Asp  Arg  Asp  Arg  Ser  Glu  Leu  Ser  Pro  Leu  Leu  Leu  Ser  Thr
               340                      345                      350
Thr  Gln  Trp  Gln  Val  Leu  Pro  Cys  Ser  Phe  Thr  Thr  Leu  Pro  Ala  Leu
          355                      360                      365
Ser  Thr  Gly  Leu  Ile  His  Leu  His  Gln  Asn  Ile  Val  Asp  Val  Gln  Tyr
     370                      375                      380
Leu  Tyr  Gly  Val  Gly  Ser  Ser  Ile  Ala  Ser  Trp  Ala  Ile  Lys  Trp  Glu
385                      390                      395                      400
Tyr  Asp  Val  Leu  Leu  Phe  Leu  Leu  Leu  Ala  Asp  Ala  Arg  Val  Cys  Ser
                    405                      410                      415
Cys  Leu  Trp  Met  Met  Leu  Leu  Ile  Ser  Gln  Ala  Glu  Ala  Leu  Glu
               420                      425                      430
Ile  Ser  Glu  Val  Lys  Met  Asp  Ala  Glu  Phe  Arg  His  Asp  Ser  Gly  Tyr
          435                      440                      445
Glu  Val  His  His  Gln  Lys  Leu  Val  Phe  Phe  Ala  Glu  Asp  Val  Gly  Ser
     450                      455                      460
Asn  Lys  Gly  Ala  Ile  Ile  Gly  Leu  Met  Val  Gly  Gly  Val  Val  Ile  Ala
```

| | | | | | | | | | | | | | | | |
|---|---|---|---|---|---|---|---|---|---|---|---|---|---|---|---|
|465| | | |470| | | |475| | | |480| | | |
|Thr|Val|Ile|Val|Ile|Thr|Leu|Val|Met|Leu|Lys|Lys|Lys|Gln|Tyr|Thr|
| | | | |485| | | |490| | | |495| | | |
|Ser|Ile|His|His|Gly|Val|Val|Glu|Val|Asp|Ala|Ala|Val|Thr|Pro|Glu|
| | | |500| | | |505| | | | |510| | | |
|Glu|Arg|His|Leu|Ser|Lys|Met|Gln|Gln|Asn|Gly|Tyr|Glu|Asn|Pro|Thr|
| | |515| | | |520| | | | |525| | | | |
|Tyr|Lys|Phe|Phe|Glu|Gln|Met|Gln|Asn| | | | | | | |
| |530| | | | |535| | | | | | | | | |

( 2 ) INFORMATION FOR SEQ ID NO:5:

( i ) SEQUENCE CHARACTERISTICS:
        ( A ) LENGTH: 7106 base pairs
        ( B ) TYPE: nucleic acid
        ( C ) STRANDEDNESS: single
        ( D ) TOPOLOGY: circular ( i i ) MOLECULE TYPE: DNA (genomic)

( i x ) FEATURE:
        ( A ) NAME/KEY: CDS
        ( B ) LOCATION: 922..2022

( x i ) SEQUENCE DESCRIPTION: SEQ ID NO:5:

```
GACGGATCGG  GAGATCTCCC  GATCCCCTAT  GGTCGACTCT  CAGTACAATC  TGCTCTGATG     60

CCGCATAGTT  AAGCCAGTAT  CTGCTCCCTG  CTTGTGTGTT  GGAGGTCGCT  GAGTAGTGCG    120

CGAGCAAAAT  TTAAGCTACA  ACAAGGCAAG  GCTTGACCGA  CAATTGCATG  AAGAATCTGC    180

TTAGGGTTAG  GCGTTTTGCG  CTGCTTCGCG  ATGTACGGGC  CAGATATACG  CGTTGACATT    240

GATTATTGAC  TAGTTATTAA  TAGTAATCAA  TTACGGGGTC  ATTAGTTCAT  AGCCCATATA    300

TGGAGTTCCG  CGTTACATAA  CTTACGGTAA  ATGGCCCGCC  TGGCTGACCG  CCCAACGACC    360

CCCGCCCATT  GACGTCAATA  ATGACGTATG  TTCCCATAGT  AACGCCAATA  GGGACTTTCC    420

ATTGACGTCA  ATGGGTGGAC  TATTTACGGT  AAACTGCCCA  CTTGGCAGTA  CATCAAGTGT    480

ATCATATGCC  AAGTACGCCC  CCTATTGACG  TCAATGACGG  TAAATGGCCC  GCCTGGCATT    540

ATGCCCAGTA  CATGACCTTA  TGGGACTTTC  CTACTTGGCA  GTACATCTAC  GTATTAGTCA    600

TCGCTATTAC  CATGGTGATG  CGGTTTTGGC  AGTACATCAA  TGGGCGTGGA  TAGCGGTTTG    660

ACTCACGGGG  ATTTCCAAGT  CTCCACCCCA  TTGACGTCAA  TGGGAGTTTG  TTTTGGCACC    720

AAAATCAACG  GGACTTTCCA  AAATGTCGTA  ACAACTCCGC  CCCATTGACG  CAAATGGGCG    780

GTAGGCGTGT  ACGGTGGGAG  GTCTATATAA  GCAGAGCTCT  CTGGCTAACT  AGAGAACCCA    840

CTGCTTAACT  GGCTTATCGA  AATTAATACG  ACTCACTATA  GGGAGACCGG  AAGCTTGCT    900
```

| | | | | | | | | | | | | | | | | |
|---|---|---|---|---|---|---|---|---|---|---|---|---|---|---|---|---|
|CTAGACTGGA|ATTCGGGCGC|G|ATG|CTG|CCC|GGT|TTG|GCA|CTG|CTC|CTG|CTG| | | |951|
| | | |Met|Leu|Pro|Gly|Leu|Ala|Leu|Leu|Leu|Leu| | | | |
| | | |1| | | |5| | | | |10| | | | |
|GCC|GCC|TGG|ACG|GCT|CGG|GCG|CTG|GAG|GTA|CCC|ACT|GAT|GGT|AAT|GCT|999|
|Ala|Ala|Trp|Thr|Ala|Arg|Ala|Leu|Glu|Val|Pro|Thr|Asp|Gly|Asn|Ala| |
| | | | |15| | | |20| | | | |25| | | |
|GGC|CTG|CTG|GCT|GAA|CCC|CAG|ATT|GCC|ATG|TTC|TGT|GGC|AGA|CTG|AAC|1047|
|Gly|Leu|Leu|Ala|Glu|Pro|Gln|Ile|Ala|Met|Phe|Cys|Gly|Arg|Leu|Asn| |
| | | |30| | | |35| | | | |40| | | | |
|ATG|CAC|ATG|AAT|GTC|CAG|AAT|GGG|AAG|TGG|GAT|TCA|GAT|CCA|TCA|GGG|1095|
|Met|His|Met|Asn|Val|Gln|Asn|Gly|Lys|Trp|Asp|Ser|Asp|Pro|Ser|Gly| |
| | | |45| | | |50| | | | |55| | | | |
|ACC|AAA|ACC|TGC|ATT|GAT|ACC|AAG|GAA|ACC|CAC|GTC|ACC|GGG|GGA|AGT|1143|
|Thr|Lys|Thr|Cys|Ile|Asp|Thr|Lys|Glu|Thr|His|Val|Thr|Gly|Gly|Ser| |
| | | |60| | | |65| | | | |70| | | | |

| | | | | | | | | | | | | | | | | |
|---|---|---|---|---|---|---|---|---|---|---|---|---|---|---|---|---|
| GCC | GGC | CAC | ACC | ACG | GCT | GGG | CTT | GTT | CGT | CTC | CTT | TCA | CCA | GGC | GCC | 1191 |
| Ala | Gly | His | Thr | Thr | Ala | Gly | Leu | Val | Arg | Leu | Leu | Ser | Pro | Gly | Ala | |
| 75 | | | | | 80 | | | | | 85 | | | | | 90 | |
| AAG | CAG | AAC | ATC | CAA | CTG | ATC | AAC | ACC | AAC | GGC | AGT | TGG | CAC | ATC | AAT | 1239 |
| Lys | Gln | Asn | Ile | Gln | Leu | Ile | Asn | Thr | Asn | Gly | Ser | Trp | His | Ile | Asn | |
| | | | | 95 | | | | | 100 | | | | | 105 | | |
| AGC | ACG | GCC | TTG | AAC | TGC | AAT | GAA | AGC | CTT | AAC | ACC | GGC | TGG | TTA | GCA | 1287 |
| Ser | Thr | Ala | Leu | Asn | Cys | Asn | Glu | Ser | Leu | Asn | Thr | Gly | Trp | Leu | Ala | |
| | | | 110 | | | | | 115 | | | | | 120 | | | |
| GGG | CTC | TTC | TAT | CAC | CAC | AAA | TTC | AAC | TCT | TCA | GGT | TGT | CCT | GAG | AGG | 1335 |
| Gly | Leu | Phe | Tyr | His | His | Lys | Phe | Asn | Ser | Ser | Gly | Cys | Pro | Glu | Arg | |
| | | 125 | | | | | 130 | | | | | 135 | | | | |
| TTG | GCC | AGC | TGC | CGA | CGC | CTT | ACC | GAT | TTT | GCC | CAG | GGC | GGG | GGT | CCT | 1383 |
| Leu | Ala | Ser | Cys | Arg | Arg | Leu | Thr | Asp | Phe | Ala | Gln | Gly | Gly | Gly | Pro | |
| | 140 | | | | | 145 | | | | | 150 | | | | | |
| ATC | AGT | TAC | GCC | AAC | GGA | AGC | GGC | CTC | GAT | GAA | CGC | CCC | TAC | TGC | TGG | 1431 |
| Ile | Ser | Tyr | Ala | Asn | Gly | Ser | Gly | Leu | Asp | Glu | Arg | Pro | Tyr | Cys | Trp | |
| 155 | | | | | 160 | | | | | 165 | | | | | 170 | |
| CAC | TAC | CCT | CCA | AGA | CCT | TGT | GGC | ATT | GTG | CCC | GCA | AAG | AGC | GTG | TGT | 1479 |
| His | Tyr | Pro | Pro | Arg | Pro | Cys | Gly | Ile | Val | Pro | Ala | Lys | Ser | Val | Cys | |
| | | | | 175 | | | | | 180 | | | | | 185 | | |
| GGC | CCG | GTA | TAT | TGC | TTC | ACT | CCC | AGC | CCC | GTG | GTG | GTG | GGA | ACG | ACC | 1527 |
| Gly | Pro | Val | Tyr | Cys | Phe | Thr | Pro | Ser | Pro | Val | Val | Val | Gly | Thr | Thr | |
| | | | 190 | | | | | 195 | | | | | 200 | | | |
| GAC | AGG | TCG | GGC | GCG | CCT | ACC | TAC | AGC | TGG | GGT | GCA | AAT | GAT | ACG | GAT | 1575 |
| Asp | Arg | Ser | Gly | Ala | Pro | Thr | Tyr | Ser | Trp | Gly | Ala | Asn | Asp | Thr | Asp | |
| | | 205 | | | | | 210 | | | | | 215 | | | | |
| GTC | TTT | GTC | CTT | AAC | AAC | ACC | AGG | CCA | CCG | CTG | GGC | AAT | TGG | TTC | GGT | 1623 |
| Val | Phe | Val | Leu | Asn | Asn | Thr | Arg | Pro | Pro | Leu | Gly | Asn | Trp | Phe | Gly | |
| | 220 | | | | | 225 | | | | | 230 | | | | | |
| TGC | ACC | TGG | ATG | AAC | TCA | ACT | GGA | TTC | ACC | AAA | GTG | TGC | GGA | GCG | CCC | 1671 |
| Cys | Thr | Trp | Met | Asn | Ser | Thr | Gly | Phe | Thr | Lys | Val | Cys | Gly | Ala | Pro | |
| 235 | | | | | 240 | | | | | 245 | | | | | 250 | |
| CCT | TGT | GTC | ATC | GGA | GGG | GTG | GGC | AAC | AAC | ACC | TTG | CTC | TGC | CCC | ACT | 1719 |
| Pro | Cys | Val | Ile | Gly | Gly | Val | Gly | Asn | Asn | Thr | Leu | Leu | Cys | Pro | Thr | |
| | | | | 255 | | | | | 260 | | | | | 265 | | |
| GAT | TGC | TTC | CGC | AAG | CAT | CCG | GAA | GCC | ACA | TAC | TCT | CGG | TGC | GGC | TCC | 1767 |
| Asp | Cys | Phe | Arg | Lys | His | Pro | Glu | Ala | Thr | Tyr | Ser | Arg | Cys | Gly | Ser | |
| | | | 270 | | | | | 275 | | | | | 280 | | | |
| GGT | CCC | TGG | ATT | ACA | CCC | AGG | TGC | ATG | GTC | GAC | TAC | CCG | TAT | AGG | CTT | 1815 |
| Gly | Pro | Trp | Ile | Thr | Pro | Arg | Cys | Met | Val | Asp | Tyr | Pro | Tyr | Arg | Leu | |
| | | 285 | | | | | 290 | | | | | 295 | | | | |
| TGG | CAC | TAT | CCT | TGT | ACC | ATC | AAT | TAC | ACC | ATA | TTC | AAA | GTC | AGG | ATG | 1863 |
| Trp | His | Tyr | Pro | Cys | Thr | Ile | Asn | Tyr | Thr | Ile | Phe | Lys | Val | Arg | Met | |
| | 300 | | | | | 305 | | | | | 310 | | | | | |
| TAC | GTG | GGA | GGG | GTC | GAG | CAC | AGG | CTG | GAA | GCG | GCC | TGC | AAC | TGG | ACG | 1911 |
| Tyr | Val | Gly | Gly | Val | Glu | His | Arg | Leu | Glu | Ala | Ala | Cys | Asn | Trp | Thr | |
| 315 | | | | | 320 | | | | | 325 | | | | | 330 | |
| CGG | GGC | GAA | CGC | TGT | GAT | CTG | GAA | GAC | AGG | GAC | AGG | TCC | GAG | CTC | AGC | 1959 |
| Arg | Gly | Glu | Arg | Cys | Asp | Leu | Glu | Asp | Arg | Asp | Arg | Ser | Glu | Leu | Ser | |
| | | | | 335 | | | | | 340 | | | | | 345 | | |
| CCG | TTA | CTG | CTG | TCC | ACC | ACG | CAG | TGG | CAG | GTC | CTT | CCG | TGT | TCT | TTC | 2007 |
| Pro | Leu | Leu | Leu | Ser | Thr | Thr | Gln | Trp | Gln | Val | Leu | Pro | Cys | Ser | Phe | |
| | | | 350 | | | | | 355 | | | | | 360 | | | |
| ACG | ACC | CTG | CCA | GCC | TAGATCTCTG | AAGTGAAGAT | GGATGCAGAA | TTCCGACATG | | | | | | | | 2062 |
| Thr | Thr | Leu | Pro | Ala | | | | | | | | | | | | |
| | | | 365 | | | | | | | | | | | | | |
| ACTCAGGATA | TGAAGTTCAT | CATCAAAAAT | TGGTGTTCTT | TGCAGAAGAT | GTGGGTTCAA | | | | | | | | | | | 2122 |
| ACAAAGGTGC | AATCATTGGA | CTCATGGTGG | GCGGTGTTGT | CATAGCGACA | GTGATCGTCA | | | | | | | | | | | 2182 |

```
TCACCTTGGT  GATGCTGAAG  AAGAAACAGT  ACACATCCAT  TCATCATGGT  GTGGTGGAGG  2242
TTGACGCCGC  TGTCACCCCA  GAGGAGCGCC  ACCTGTCCAA  GATGCAGCAG  AACGGCTACG  2302
AAAATCCAAC  CTACAAGTTC  TTTGAGCAGA  TGCAGAACTA  GACCCCGCC   ACAGCAGCCT  2362
CTGAAGTTGG  ACAGCAAAAC  CATTGCTTCA  CTACCCATCG  GTGTCCATTT  ATAGAATAAT  2422
GTGGGAAGAA  ACAAACCCGT  TTTATGATTT  ACTCATTATC  GCCTTTTGAC  AGCTGTGCTG  2482
TAACACAAGT  AGATGCCTGA  ACTTGAATTA  ATCCACACAT  CAGTAATGTA  TTCTATCTCT  2542
CTTTACATTT  TGGTCTCTAT  ACTACATTAT  TAATGGGTTT  TGTGTACTGT  AAAGAATTTA  2602
GCTGTATCAA  ACTAGTGCAT  GAATAGGCCG  CTCGAGCATG  CATCTAGAGG  GCCCTATTCT  2662
ATAGTGTCAC  CTAAATGCTC  GCTGATCAGC  CTCGACTGTG  CCTTCTAGTT  GCCAGCCATC  2722
TGTTGTTTGC  CCCTCCCCCG  TGCCTTCCTT  GACCCTGGAA  GGTGCCACTC  CCACTGTCCT  2782
TTCCTAATAA  AATGAGGAAA  TTGCATCGCA  TTGTCTGAGT  AGGTGTCATT  CTATTCTGGG  2842
GGGTGGGGTG  GGGCAGGACA  GCAAGGGGGA  GGATTGGGAA  GACAATAGCA  GGCATGCTGG  2902
GGATGCGGTG  GGCTCTATGG  AACCAGCTGG  GGCTCGAGGG  GGGATCCCCA  CGCGCCCTGT  2962
AGCGGCGCAT  TAAGCGCGGC  GGGTGTGGTG  GTTACGCGCA  GCGTGACCGC  TACACTTGCC  3022
AGCGCCCTAG  CGCCCGCTCC  TTTCGCTTTC  TTCCCTTCCT  TTCTCGCCAC  GTTCGCCGGC  3082
TTTCCCCGTC  AAGCTCTAAA  TCGGGGCATC  CCTTTAGGGT  TCCGATTTAG  TGCTTTACGG  3142
CACCTCGACC  CCAAAAAACT  TGATTAGGGT  GATGGTTCAC  GTAGTGGGCC  ATCGCCCTGA  3202
TAGACGGTTT  TTCGCCTTTA  CTGAGCACTC  TTTAATAGTG  GACTCTTGTT  CCAAACTGGA  3262
ACAACACTCA  ACCCTATCTC  GGTCTATTCT  TTTGATTTAT  AAGATTTCCA  TCGCCATGTA  3322
AAAGTGTTAC  AATTAGCATT  AAATTACTTC  TTTATATGCT  ACTATTCTTT  TGGCTTCGTT  3382
CACGGGGTGG  GTACCGAGCT  CGAATTCTGT  GGAATGTGTG  TCAGTTAGGG  TGTGGAAAGT  3442
CCCCAGGCTC  CCCAGGCAGG  CAGAAGTATG  CAAAGCATGC  ATCTCAATTA  GTCAGCAACC  3502
AGGTGTGGAA  AGTCCCCAGG  CTCCCCAGCA  GGCAGAAGTA  TGCAAAGCAT  GCATCTCAAT  3562
TAGTCAGCAA  CCATAGTCCC  GCCCCTAACT  CCGCCCATCC  CGCCCCTAAC  TCCGCCCAGT  3622
TCCGCCCATT  CTCCGCCCCA  TGGCTGACTA  ATTTTTTTA   TTTATGCAGA  GGCCGAGGCC  3682
GCCTCGGCCT  CTGAGCTATT  CCAGAAGTAG  TGAGGAGGCT  TTTTTGGAGG  CCTAGGCTTT  3742
TGCAAAAAGC  TCCCGGGAGC  TTGGATATCC  ATTTTCGGAT  CTGATCAAGA  GACAGGATGA  3802
GGATCGTTTC  GCATGATTGA  ACAAGATGGA  TTGCACGCAG  GTTCTCCGGC  CGCTTGGGTG  3862
GAGAGGCTAT  TCGGCTATGA  CTGGGCACAA  CAGACAATCG  GCTGCTCTGA  TGCCGCCGTG  3922
TTCCGGCTGT  CAGCGCAGGG  GCGCCCGGTT  CTTTTTGTCA  AGACCGACCT  GTCCGGTGCC  3982
CTGAATGAAC  TGCAGGACGA  GGCAGCGCGG  CTATCGTGGC  TGGCCACGAC  GGGCGTTCCT  4042
TGCGCAGCTG  TGCTCGACGT  TGTCACTGAA  GCGGGAAGGG  ACTGGCTGCT  ATTGGGCGAA  4102
GTGCCGGGGC  AGGATCTCCT  GTCATCTCAC  CTTGCTCCTG  CCGAGAAAGT  ATCCATCATG  4162
GCTGATGCAA  TGCGGCGGCT  GCATACGCTT  GATCCGGCTA  CCTGCCCATT  CGACCACCAA  4222
GCGAAACATC  GCATCGAGCG  AGCACGTACT  CGGATGGAAG  CCGGTCTTGT  CGATCAGGAT  4282
GATCTGGACG  AAGAGCATCA  GGGGCTCGCG  CCAGCCGAAC  TGTTCGCCAG  GCTCAAGGCG  4342
CGCATGCCCG  ACGGCGAGGA  TCTCGTCGTG  ACCCATGGCG  ATGCCTGCTT  GCCGAATATC  4402
ATGGTGGAAA  ATGGCCGCTT  TTCTGGATTC  ATCGACTGTG  GCCGGCTGGG  TGTGGCGGAC  4462
CGCTATCAGG  ACATAGCGTT  GGCTACCCGT  GATATTGCTG  AAGAGCTTGG  CGGCGAATGG  4522
GCTGACCGCT  TCCTCGTGCT  TTACGGTATC  GCCGCTCCCG  ATTCGCAGCG  CATCGCCTTC  4582
```

```
TATCGCCTTC TTGACGAGTT CTTCTGAGCG GGACTCTGGG GTTCGAAATG ACCGACCAAG    4642
CGACGCCCAA CCTGCCATCA CGAGATTTCG ATTCCACCGC CGCCTTCTAT GAAAGGTTGG    4702
GCTTCGGAAT CGTTTTCCGG GACGCCGGCT GGATGATCCT CCAGCGCGGG GATCTCATGC    4762
TGGAGTTCTT CGCCCACCCC AACTTGTTTA TTGCAGCTTA TAATGGTTAC AAATAAAGCA    4822
ATAGCATCAC AAATTTCACA AATAAAGCAT TTTTTCACT GCATTCTAGT TGTGGTTTGT     4882
CCAAACTCAT CAATGTATCT TATCATGTCT GGATCCCGTC GACCTCGAGA GCTTGGCGTA    4942
ATCATGGTCA TAGCTGTTTC CTGTGTGAAA TTGTTATCCG CTCACAATTC CACACAACAT    5002
ACGAGCCGGA AGCATAAAGT GTAAAGCCTG GGGTGCCTAA TGAGTGAGCT AACTCACATT    5062
AATTGCGTTG CGCTCACTGC CCGCTTTCCA GTCGGGAAAC CTGTCGTGCC AGCTGCATTA    5122
ATGAATCGGC CAACGCGCGG GGAGAGGCGG TTTGCGTATT GGGCGCTCTT CCGCTTCCTC    5182
GCTCACTGAC TCGCTGCGCT CGGTCGTTCG GCTGCGGCGA GCGGTATCAG CTCACTCAAA    5242
GGCGGTAATA CGGTTATCCA CAGAATCAGG GGATAACGCA GGAAAGAACA TGTGAGCAAA    5302
AGGCCAGCAA AAGGCCAGGA ACCGTAAAAA GGCCGCGTTG CTGGCGTTTT TCCATAGGCT    5362
CCGCCCCCCT GACGAGCATC ACAAAAATCG ACGCTCAAGT CAGAGGTGGC GAAACCCGAC    5422
AGGACTATAA AGATACCAGG CGTTTCCCCC TGGAAGCTCC CTCGTGCGCT CTCCTGTTCC    5482
GACCCTGCCG CTTACCGGAT ACCTGTCCGC CTTTCTCCCT TCGGGAAGCG TGGCGCTTTC    5542
TCAATGCTCA CGCTGTAGGT ATCTCAGTTC GGTGTAGGTC GTTCGCTCCA AGCTGGGCTG    5602
TGTGCACGAA CCCCCCGTTC AGCCCGACCG CTGCGCCTTA TCCGGTAACT ATCGTCTTGA    5662
GTCCAACCCG GTAAGACACG ACTTATCGCC ACTGGCAGCA GCCACTGGTA ACAGGATTAG    5722
CAGAGCGAGG TATGTAGGCG GTGCTACAGA GTTCTTGAAG TGGTGGCCTA ACTACGGCTA    5782
CACTAGAAGG ACAGTATTTG GTATCTGCGC TCTGCTGAAG CCAGTTACCT TCGGAAAAAG    5842
AGTTGGTAGC TCTTGATCCG GCAAACAAAC CACCGCTGGT AGCGGTGGTT TTTTGTTTG    5902
CAAGCAGCAG ATTACGCGCA GAAAAAAAGG ATCTCAAGAA GATCCTTTGA TCTTTTCTAC    5962
GGGGTCTGAC GCTCAGTGGA ACGAAAACTC ACGTTAAGGG ATTTTGGTCA TGAGATTATC    6022
AAAAGGATC TTCACCTAGA TCCTTTTAAA TTAAAAATGA AGTTTTAAAT CAATCTAAAG     6082
TATATATGAG TAAACTTGGT CTGACAGTTA CCAATGCTTA ATCAGTGAGG CACCTATCTC    6142
AGCGATCTGT CTATTTCGTT CATCCATAGT TGCCTGACTC CCCGTCGTGT AGATAACTAC    6202
GATACGGGAG GGCTTACCAT CTGGCCCCAG TGCTGCAATG ATACCGCGAG ACCCACGCTC    6262
ACCGGCTCCA GATTTATCAG CAATAAACCA GCCAGCCGGA AGGGCCGAGC GCAGAAGTGG    6322
TCCTGCAACT TTATCCGCCT CCATCCAGTC TATTAATTGT TGCCGGGAAG CTAGAGTAAG    6382
TAGTTCGCCA GTTAATAGTT TGCGCAACGT TGTTGCCATT GCTACAGGCA TCGTGGTGTC    6442
ACGCTCGTCG TTTGGTATGG CTTCATTCAG CTCCGGTTCC CAACGATCAA GGCGAGTTAC    6502
ATGATCCCCC ATGTTGTGCA AAAAGCGGT TAGCTCCTTC GGTCCTCCGA TCGTTGTCAG     6562
AAGTAAGTTG GCCGCAGTGT TATCACTCAT GGTTATGGCA GCACTGCATA ATTCTCTTAC    6622
TGTCATGCCA TCCGTAAGAT GCTTTTCTGT GACTGGTGAG TACTCAACCA AGTCATTCTG    6682
AGAATAGTGT ATGCGGCGAC CGAGTTGCTC TTGCCCGGCG TCAATACGGG ATAATACCGC    6742
GCCACATAGC AGAACTTTAA AAGTGCTCAT CATTGGAAAA CGTTCTTCGG GGCGAAAACT    6802
CTCAAGGATC TTACCGCTGT TGAGATCCAG TTCGATGTAA CCCACTCGTG CACCCAACTG    6862
ATCTTCAGCA TCTTTTACTT TCACCAGCGT TTCTGGGTGA GCAAAAACAG GAAGGCAAAA    6922
TGCCGCAAAA AAGGGAATAA GGGCGACACG GAAATGTTGA ATACTCATAC TCTTCCTTTT    6982
```

```
TCAATATTAT TGAAGCATTT ATCAGGGTTA TTGTCTCATG AGCGGATACA TATTTGAATG        7042

TATTTAGAAA AATAAACAAA TAGGGGTTCC GCGCACATTT CCCCGAAAAG TGCCACCTGA        7102

CGTC                                                                    7106
```

( 2 ) INFORMATION FOR SEQ ID NO:6:

( i ) SEQUENCE CHARACTERISTICS:
        ( A ) LENGTH: 367 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Leu Pro Gly Leu Ala Leu Leu Leu Ala Ala Trp Thr Ala Arg
  1               5                  10                  15

Ala Leu Glu Val Pro Thr Asp Gly Asn Ala Gly Leu Leu Ala Glu Pro
                 20                  25                  30

Gln Ile Ala Met Phe Cys Gly Arg Leu Asn Met His Met Asn Val Gln
             35                  40                  45

Asn Gly Lys Trp Asp Ser Asp Pro Ser Gly Thr Lys Thr Cys Ile Asp
         50                  55                  60

Thr Lys Glu Thr His Val Thr Gly Gly Ser Ala Gly His Thr Thr Ala
 65                  70                  75                  80

Gly Leu Val Arg Leu Leu Ser Pro Gly Ala Lys Gln Asn Ile Gln Leu
                 85                  90                  95

Ile Asn Thr Asn Gly Ser Trp His Ile Asn Ser Thr Ala Leu Asn Cys
            100                 105                 110

Asn Glu Ser Leu Asn Thr Gly Trp Leu Ala Gly Leu Phe Tyr His His
            115                 120                 125

Lys Phe Asn Ser Ser Gly Cys Pro Glu Arg Leu Ala Ser Cys Arg Arg
    130                 135                 140

Leu Thr Asp Phe Ala Gln Gly Gly Gly Pro Ile Ser Tyr Ala Asn Gly
145                 150                 155                 160

Ser Gly Leu Asp Glu Arg Pro Tyr Cys Trp His Tyr Pro Pro Arg Pro
                165                 170                 175

Cys Gly Ile Val Pro Ala Lys Ser Val Cys Gly Pro Val Tyr Cys Phe
            180                 185                 190

Thr Pro Ser Pro Val Val Val Gly Thr Thr Asp Arg Ser Gly Ala Pro
            195                 200                 205

Thr Tyr Ser Trp Gly Ala Asn Asp Thr Asp Val Phe Val Leu Asn Asn
    210                 215                 220

Thr Arg Pro Pro Leu Gly Asn Trp Phe Gly Cys Thr Trp Met Asn Ser
225                 230                 235                 240

Thr Gly Phe Thr Lys Val Cys Gly Ala Pro Pro Cys Val Ile Gly Gly
                245                 250                 255

Val Gly Asn Asn Thr Leu Leu Cys Pro Thr Asp Cys Phe Arg Lys His
            260                 265                 270

Pro Glu Ala Thr Tyr Ser Arg Cys Gly Ser Gly Pro Trp Ile Thr Pro
            275                 280                 285

Arg Cys Met Val Asp Tyr Pro Tyr Arg Leu Trp His Tyr Pro Cys Thr
    290                 295                 300

Ile Asn Tyr Thr Ile Phe Lys Val Arg Met Tyr Val Gly Gly Val Glu
305                 310                 315                 320

His Arg Leu Glu Ala Ala Cys Asn Trp Thr Arg Gly Glu Arg Cys Asp
```

|   |   |   | 325 |   |   |   | 330 |   |   |   | 335 |   |
|---|---|---|---|---|---|---|---|---|---|---|---|---|
| Leu | Glu | Asp | Arg | Asp | Arg | Ser | Glu | Leu | Ser | Pro | Leu | Leu | Leu | Ser | Thr |
|   |   |   | 340 |   |   |   | 345 |   |   |   | 350 |   |

| Thr | Gln | Trp | Gln | Val | Leu | Pro | Cys | Ser | Phe | Thr | Thr | Leu | Pro | Ala |
|---|---|---|---|---|---|---|---|---|---|---|---|---|---|---|
|   |   |   | 355 |   |   |   | 360 |   |   |   | 365 |   |

( 2 ) INFORMATION FOR SEQ ID NO:7:

( i ) SEQUENCE CHARACTERISTICS:
( A ) LENGTH: 4810 base pairs
( B ) TYPE: nucleic acid
( C ) STRANDEDNESS: single
( D ) TOPOLOGY: circular ( i i ) MOLECULE TYPE: DNA (genomic)

( i x ) FEATURE:
( A ) NAME/KEY: CDS
( B ) LOCATION: 2227..2910

( x i ) SEQUENCE DESCRIPTION: SEQ ID NO:7:

```
GCGTAATCTG CTGCTTGCAA ACAAAAAAAC CACCGCTACC AGCGGTGGTT TGTTTGCCGG       60
ATCAAGAGCT ACCAACTCTT TTTCCGAAGG TAACTGGCTT CAGCAGAGCG CAGATACCAA      120
ATACTGTCCT TCTAGTGTAG CCGTAGTTAG GCCACCACTT CAAGAACTCT GTAGCACCGC      180
CTACATACCT CGCTCTGCTA ATCCTGTTAC CAGTGGCTGC TGCCAGTGGC GATAAGTCGT      240
GTCTTACCGG GTTGGACTCA AGACGATAGT TACCGGATAA GGCGCAGCGG TCGGGCTGAA      300
CGGGGGGTTC GTGCACACAG CCCAGCTTGG AGCGAACGAC CTACACCGAA CTGAGATACC      360
TACAGCGTGA GCATTGAGAA AGCGCCACGC TTCCCGAAGG GAGAAAGGCG ACAGGTATC       420
CGGTAAGCGG CAGGGTCGGA ACAGGAGAGC GCACGAGGGA GCTTCCAGGG GGAAACGCCT      480
GGTATCTTTA TAGTCCTGTC GGGTTTCGCC ACCTCTGACT TGAGCGTCGA TTTTTGTGAT      540
GCTCGTCAGG GGGGCGGAGC CTATGGAAAA ACGCCAGCAA CGCAAGCTAG CTTCTAGCTA      600
GAAATTGTAA ACGTTAATAT TTGTTAAAA TTCGCGTTAA ATTTTTGTTA AATCAGCTCA       660
TTTTTTAACC AATAGGCCGA AATCGGCAAA ATCCCTTATA AATCAAAGA ATAGCCCGAG       720
ATAGGGTTGA GTGTTGTTCC AGTTTGGAAC AAGAGTCCAC TATTAAAGAA CGTGGACTCC      780
AACGTCAAAG GGCGAAAAAC CGTCTATCAG GGCGATGGCC GCCCACTACG TGAACCATCA      840
CCCAAATCAA GTTTTTTGGG GTCGAGGTGC CGTAAAGCAC TAAATCGGAA CCCTAAAGGG      900
AGCCCCGAT TTAGAGCTTG ACGGGAAAG CCGGCGAACG TGGCGAGAAA GGAAGGGAAG       960
AAAGCGAAAG GAGCGGGCGC TAGGGCGCTG GCAAGTGTAG CGGTCACGCT GCGCGTAACC     1020
ACCACACCCG CCGCGCTTAA TGCGCCGCTA CAGGGCGCGT ACTATGGTTG CTTTGACGAG     1080
ACCGTATAAC GTGCTTTCCT CGTTGGAATC AGAGCGGGAG CTAAACAGGA GGCCGATTAA     1140
AGGGATTTTA GACAGGAACG GTACGCCAGC TGGATCACCG CGGTCTTTCT CAACGTAACA     1200
CTTTACAGCG GCGCGTCATT TGATATGATG CGCCCCGCTT CCCGATAAGG GAGCAGGCCA     1260
GTAAAAGCAT TACCCGTGGT GGGGTTCCCG AGCGGCCAAA GGGAGCAGAC TCTAAATCTG     1320
CCGTCATCGA CTTCGAAGGT TCGAATCCTT CCCCCACCAC CATCACTTTC AAAAGTCCGA     1380
AAGAATCTGC TCCCTGCTTG TGTGTTGGAG GTCGCTGAGT AGTGCGCGAG TAAAATTTAA     1440
GCTACAACAA GGCAAGGCTT GACCGACAAT TGCATGAAGA ATCTGCTTAG GGTTAGGCGT     1500
TTTGCGCTGC TTCGCGATGT ACGGGCCAGA TATACGCGTT GACATTGATT ATTGACTAGT     1560
TATTAATAGT AATCAATTAC GGGGTCATTA GTTCATAGCC CATATATGGA GTTCCGCGTT     1620
ACATAACTTA CGGTAAATGG CCCGCCTGGC TGACCGCCCA ACGACCCCCG CCCATTGACG     1680
```

```
TCAATAATGA CGTATGTTCC CATAGTAACG CCAATAGGGA CTTTCCATTG ACGTCAATGG       1740

GTGGACTATT TACGGTAAAC TGCCCACTTG GCAGTACATC AAGTGTATCA TATGCCAAGT       1800

ACGCCCCCTA TTGACGTCAA TGACGGTAAA TGGCCCGCCT GGCATTATGC CCAGTACATG       1860

ACCTTATGGG ACTTTCCTAC TTGGCAGTAC ATCTACGTAT TAGTCATCGC TATTACCATG       1920

GTGATGCGGT TTTGGCAGTA CATCAATGGG CGTGGATAGC GGTTTGACTC ACGGGGATTT       1980

CCAAGTCTCC ACCCCATTGA CGTCAATGGG AGTTTGTTTT GGCACCAAAA TCAACGGGAC       2040

TTTCCAAAAT GTCGTAACAA CTCCGCCCCA TTGACGCAAA TGGGCGGTAG GCGTGTACGG       2100

TGGGAGGTCT ATATAAGCAG AGCTCTCTGG CTAACTAGAG AACCCACTGC TTAACTGGCT       2160

TATCGAAATT AATACGACTC ACTATAGGGA GACCGGAAGC TTGGTACCGA GCTCGGATCT       2220
```

```
GCCACC ATG GCA ACA GGA TCA AGA ACA TCA CTG CTG CTG GCA TTT GGA          2268
       Met Ala Thr Gly Ser Arg Thr Ser Leu Leu Leu Ala Phe Gly
         1               5                  10

CTG CTG TGT CTG CCA TGG CTG CAA GAA GGA TCA GCA GCA GCA GCA GCG          2316
Leu Leu Cys Leu Pro Trp Leu Gln Glu Gly Ser Ala Ala Ala Ala Ala
 15              20                  25                      30

AAT TCG GAT CCC TAC CAA GTG CGC AAT TCC TCG GGG CTT TAC CAT GTC          2364
Asn Ser Asp Pro Tyr Gln Val Arg Asn Ser Ser Gly Leu Tyr His Val
             35                  40                      45

ACC AAT GAT TGC CCT AAT TCG AGT ATT GTG TAC GAG GCG GCC GAT GCC          2412
Thr Asn Asp Cys Pro Asn Ser Ser Ile Val Tyr Glu Ala Ala Asp Ala
             50                  55                      60

ATC CTA CAC ACT CCG GGG TGT GTC CCT TGC GTT CGA GAG GGT AAC GCC          2460
Ile Leu His Thr Pro Gly Cys Val Pro Cys Val Arg Glu Gly Asn Ala
             65                  70                      75

TCG AGG TGT TGG GTG GCG GTG ACC CCC ACG GTG GCC ACC AGG GAC GGC          2508
Ser Arg Cys Trp Val Ala Val Thr Pro Thr Val Ala Thr Arg Asp Gly
         80                  85                      90

AAA CTC CCC ACA ACG CAG CTT CGA CGT CAT ATC GAT CTG CTC GTC GGG          2556
Lys Leu Pro Thr Thr Gln Leu Arg Arg His Ile Asp Leu Leu Val Gly
 95                 100                 105                    110

AGC GCC ACC CTC TGC TCG GCC CTC TAC GTG GGG GAC CTG TGC GGG TCT          2604
Ser Ala Thr Leu Cys Ser Ala Leu Tyr Val Gly Asp Leu Cys Gly Ser
                115                 120                    125

GTC TTT CTT GTT GGT CAA CTG TTT ACC TTC TCT CCC AGG CGC CAC TGG          2652
Val Phe Leu Val Gly Gln Leu Phe Thr Phe Ser Pro Arg Arg His Trp
            130                 135                    140

ACG ACG CAA GAC TGC AAT TGT TCT ATC TAT CCC GGC CAT ATA ACG GGT          2700
Thr Thr Gln Asp Cys Asn Cys Ser Ile Tyr Pro Gly His Ile Thr Gly
            145                 150                    155

CAT CGT ATG GCA TGG GAT ATG ATG ATG AAC TGG TCC CCT ACG GCA GCG          2748
His Arg Met Ala Trp Asp Met Met Met Asn Trp Ser Pro Thr Ala Ala
        160                 165                    170

TTG GTG GTA GCT CAG CTG CTC CGG ATC CCA CAA GCC ATC TTG GAC ATG          2796
Leu Val Val Ala Gln Leu Leu Arg Ile Pro Gln Ala Ile Leu Asp Met
175             180                 185                        190

ATC GCT GGT GCC CAC TGG GGA GTC CTG GCG GGC ATA GCG TAT TTC TCC          2844
Ile Ala Gly Ala His Trp Gly Val Leu Ala Gly Ile Ala Tyr Phe Ser
                195                 200                    205

ATG GTG GGG AAC TGG GCG AAG GTC CTG GTA GTG CTG CTG CTA TTT GCC          2892
Met Val Gly Asn Trp Ala Lys Val Leu Val Val Leu Leu Leu Phe Ala
            210                 215                    220

GGC GTT GAC GCG GAG ATC TAATCTAGAG GGCCCTATTC TATAGTGTCA                 2940
Gly Val Asp Ala Glu Ile
                225

CCTAAATGCT AGAGGATCTT TGTGAAGGAA CCTTACTTCT GTGGTGTGAC ATAATTGGAC        3000
```

| | | | | | |
|---|---|---|---|---|---|
| AAACTACCTA | CAGAGATTTA | AAGCTCTAAG | GTAAATATAA | AATTTTTAAG | TGTATAATGT | 3060
| GTTAAACTAC | TGATTCTAAT | TGTTTGTGTA | TTTTAGATTC | CAACCTATGG | AACTGATGAA | 3120
| TGGGAGCAGT | GGTGGAATGC | CTTTAATGAG | GAAAACCTGT | TTTGCTCAGA | AGAAATGCCA | 3180
| TCTAGTGATG | ATGAGGCTAC | TGCTGACTCT | CAACATTCTA | CTCCTCCAAA | AAAGAAGAGA | 3240
| AAGGTAGAAG | ACCCCAAGGA | CTTTCCTTCA | GAATTGCTAA | GTTTTTGAG | TCATGCTGTG | 3300
| TTTAGTAATA | GAACTCTTGC | TTGCTTTGCT | ATTTACACCA | CAAAGGAAAA | AGCTGCACTG | 3360
| CTATACAAGA | AAATTATGGA | AAAATATTCT | GTAACCTTTA | TAAGTAGGCA | TAACAGTTAT | 3420
| AATCATAACA | TACTGTTTTT | TCTTACTCCA | CACAGGCATA | GAGTGTCTGC | TATTAATAAC | 3480
| TATGCTCAAA | AATTGTGTAC | CTTTAGCTTT | TTAATTTGTA | AAGGGGTTAA | TAAGGAATAT | 3540
| TTGATGTATA | GTGCCTTGAC | TAGAGATCAT | AATCAGCCAT | ACCACATTTG | TAGAGGTTTT | 3600
| ACTTGCTTTA | AAAAACCTCC | CACACCTCCC | CCTGAACCTG | AAACATAAAA | TGAATGCAAT | 3660
| TGTTGTTGTT | AACTTGTTTA | TTGCAGCTTA | TAATGGTTAC | AAATAAAGCA | ATAGCATCAC | 3720
| AAATTTCACA | AATAAAGCAT | TTTTTCACT | GCATTCTAGT | TGTGGTTTGT | CCAAACTCAT | 3780
| CAATGTATCT | TATCATGTCT | GGATCGATCC | CGCCATGGTA | TCAACGCCAT | ATTTCTATTT | 3840
| ACAGTAGGGA | CCTCTTCGTT | GTGTAGGTAC | CGCTGTATTC | CTAGGGAAAT | AGTAGAGGCA | 3900
| CCTTGAACTG | TCTGCATCAG | CCATATAGCC | CCCGCTGTTC | GACTTACAAA | CACAGGCACA | 3960
| GTACTGACAA | ACCCATACAC | CTCCTCTGAA | ATACCCATAG | TTGCTAGGGC | TGTCTCCGAA | 4020
| CTCATTACAC | CCTCCAAAGT | CAGAGCTGTA | ATTTCGCCAT | CAAGGGCAGC | GAGGGCTTCT | 4080
| CCAGATAAAA | TAGCTTCTGC | CGAGAGTCCC | GTAAGGGTAG | ACACTTCAGC | TAATCCCTCG | 4140
| ATGAGGTCTA | CTAGAATAGT | CAGTGCGGCT | CCCATTTGA | AAATTCACTT | ACTTGATCAG | 4200
| CTTCAGAAGA | TGGCGGAGGG | CCTCCAACAC | AGTAATTTTC | CTCCCGACTC | TTAAAATAGA | 4260
| AAATGTCAAG | TCAGTTAAGC | AGGAAGTGGA | CTAACTGACG | CAGCTGGCCG | TGCGACATCC | 4320
| TCTTTTAATT | AGTTGCTAGG | CAACGCCCTC | CAGAGGGCGT | GTGGTTTTGC | AAGAGGAAGC | 4380
| AAAAGCCTCT | CCACCCAGGC | CTAGAATGTT | TCCACCCAAT | CATTACTATG | ACAACAGCTG | 4440
| TTTTTTTTAG | TATTAAGCAG | AGGCCGGGGA | CCCCTGGCCC | GCTTACTCTG | GAGAAAAAGA | 4500
| AGAGAGGCAT | TGTAGAGGCT | TCCAGAGGCA | ACTTGTCAAA | ACAGGACTGC | TTCTATTTCT | 4560
| GTCACACTGT | CTGGCCCTGT | CACAAGGTCC | AGCACCTCCA | TACCCCTTT | AATAAGCAGT | 4620
| TTGGGAACGG | GTGCGGGTCT | TACTCCGCCC | ATCCCGCCCC | TAACTCCGCC | CAGTTCCGCC | 4680
| CATTCTCCGC | CCCATGGCTG | ACTAATTTTT | TTTATTTATG | CAGAGGCCGA | GGCCGCCTCG | 4740
| GCCTCTGAGC | TATTCCAGAA | GTAGTGAGGA | GGCTTTTTTG | GAGGCCTAGG | CTTTTGCAAA | 4800
| AAGCTAATTC | | | | | | 4810

( 2 ) INFORMATION FOR SEQ ID NO:8:

( i ) SEQUENCE CHARACTERISTICS:
        ( A ) LENGTH: 228 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Met | Ala | Thr | Gly | Ser | Arg | Thr | Ser | Leu | Leu | Leu | Ala | Phe | Gly | Leu | Leu |
|---|---|---|---|---|---|---|---|---|---|---|---|---|---|---|---|
| 1 | | | | 5 | | | | | 10 | | | | | 15 | |

| Cys | Leu | Pro | Trp | Leu | Gln | Glu | Gly | Ser | Ala | Ala | Ala | Ala | Ala | Asn | Ser |
|---|---|---|---|---|---|---|---|---|---|---|---|---|---|---|---|
| | | | 20 | | | | | 25 | | | | | 30 | | |

| Asp | Pro | Tyr<br>35 | Gln | Val | Arg | Asn | Ser<br>40 | Ser | Gly | Leu | Tyr | His<br>45 | Val | Thr | Asn |
|---|---|---|---|---|---|---|---|---|---|---|---|---|---|---|---|
| Asp | Cys<br>50 | Pro | Asn | Ser | Ser<br>55 | Ile | Val | Tyr | Glu | Ala<br>60 | Ala | Asp | Ala | Ile | Leu |
| His<br>65 | Thr | Pro | Gly | Cys<br>70 | Val | Pro | Cys | Val | Arg<br>75 | Glu | Gly | Asn | Ala | Ser | Arg<br>80 |
| Cys | Trp | Val | Ala | Val<br>85 | Thr | Pro | Thr | Val | Ala<br>90 | Thr | Arg | Asp | Gly | Lys<br>95 | Leu |
| Pro | Thr | Thr | Gln<br>100 | Leu | Arg | Arg | His | Ile<br>105 | Asp | Leu | Leu | Val | Gly<br>110 | Ser | Ala |
| Thr | Leu | Cys<br>115 | Ser | Ala | Leu | Tyr | Val<br>120 | Gly | Asp | Leu | Cys | Gly<br>125 | Ser | Val | Phe |
| Leu | Val<br>130 | Gly | Gln | Leu | Phe | Thr<br>135 | Phe | Ser | Pro | Arg | Arg<br>140 | His | Trp | Thr | Thr |
| Gln<br>145 | Asp | Cys | Asn | Cys | Ser<br>150 | Ile | Tyr | Pro | Gly | His<br>155 | Ile | Thr | Gly | His | Arg<br>160 |
| Met | Ala | Trp | Asp | Met<br>165 | Met | Met | Asn | Trp | Ser<br>170 | Pro | Thr | Ala | Ala | Leu<br>175 | Val |
| Val | Ala | Gln | Leu<br>180 | Leu | Arg | Ile | Pro | Gln<br>185 | Ala | Ile | Leu | Asp | Met<br>190 | Ile | Ala |
| Gly | Ala | His<br>195 | Trp | Gly | Val | Leu | Ala<br>200 | Gly | Ile | Ala | Tyr | Phe<br>205 | Ser | Met | Val |
| Gly | Asn<br>210 | Trp | Ala | Lys | Val | Leu<br>215 | Val | Val | Leu | Leu | Leu<br>220 | Phe | Ala | Gly | Val |
| Asp<br>225 | Ala | Glu | Ile | | | | | | | | | | | | |

( 2 ) INFORMATION FOR SEQ ID NO:9:

( i ) SEQUENCE CHARACTERISTICS:
        ( A ) LENGTH: 5323 base pairs
        ( B ) TYPE: nucleic acid
        ( C ) STRANDEDNESS: single
        ( D ) TOPOLOGY: circular ( i i ) MOLECULE TYPE: DNA (genomic)

( i x ) FEATURE:
        ( A ) NAME/KEY: CDS
        ( B ) LOCATION: 2227..3423

( x i ) SEQUENCE DESCRIPTION: SEQ ID NO:9:

```
GCGTAATCTG CTGCTTGCAA ACAAAAAAAC CACCGCTACC AGCGGTGGTT TGTTTGCCGG      60
ATCAAGAGCT ACCAACTCTT TTTCCGAAGG TAACTGGCTT CAGCAGAGCG CAGATACCAA     120
ATACTGTCCT TCTAGTGTAG CCGTAGTTAG GCCACCACTT CAAGAACTCT GTAGCACCGC     180
CTACATACCT CGCTCTGCTA ATCCTGTTAC CAGTGGCTGC TGCCAGTGGC GATAAGTCGT     240
GTCTTACCGG GTTGGACTCA AGACGATAGT TACCGGATAA GGCGCAGCGG TCGGGCTGAA     300
CGGGGGGTTC GTGCACACAG CCCAGCTTGG AGCGAACGAC CTACACCGAA CTGAGATACC     360
TACAGCGTGA GCATTGAGAA AGCGCCACGC TTCCCGAAGG GAGAAAGGCG GACAGGTATC     420
CGGTAAGCGG CAGGGTCGGA ACAGGAGAGC GCACGAGGGA GCTTCCAGGG GGAAACGCCT     480
GGTATCTTTA TAGTCCTGTC GGGTTTCGCC ACCTCTGACT TGAGCGTCGA TTTTTGTGAT     540
GCTCGTCAGG GGGGCGGAGC CTATGGAAAA ACGCCAGCAA CGCAAGCTAG CTTCTAGCTA     600
GAAATTGTAA ACGTTAATAT TTTGTTAAAA TTCGCGTTAA ATTTTTGTTA AATCAGCTCA     660
TTTTTTAACC AATAGGCCGA AATCGGCAAA ATCCCTTATA AATCAAAAGA ATAGCCCGAG     720
```

```
ATAGGGTTGA  GTGTTGTTCC  AGTTTGGAAC  AAGAGTCCAC  TATTAAAGAA  CGTGGACTCC    780

AACGTCAAAG  GGCGAAAAAC  CGTCTATCAG  GGCGATGGCC  GCCCACTACG  TGAACCATCA    840

CCCAAATCAA  GTTTTTGGG   GTCGAGGTGC  CGTAAAGCAC  TAAATCGGAA  CCCTAAAGGG    900

AGCCCCCGAT  TTAGAGCTTG  ACGGGGAAAG  CCGGCGAACG  TGGCGAGAAA  GGAAGGGAAG    960

AAAGCGAAAG  GAGCGGGCGC  TAGGGCGCTG  GCAAGTGTAG  CGGTCACGCT  GCGCGTAACC   1020

ACCACACCCG  CCGCGCTTAA  TGCGCCGCTA  CAGGGCGCGT  ACTATGGTTG  CTTTGACGAG   1080

ACCGTATAAC  GTGCTTTCCT  CGTTGGAATC  AGAGCGGGAG  CTAAACAGGA  GGCCGATTAA   1140

AGGGATTTTA  GACAGGAACG  GTACGCCAGC  TGGATCACCG  CGGTCTTTCT  CAACGTAACA   1200

CTTTACAGCG  GCGCGTCATT  TGATATGATG  CGCCCGCTT   CCCGATAAGG  GAGCAGGCCA   1260

GTAAAAGCAT  TACCCGTGGT  GGGGTTCCCG  AGCGGCCAAA  GGGAGCAGAC  TCTAAATCTG   1320

CCGTCATCGA  CTTCGAAGGT  TCGAATCCTT  CCCCCACCAC  CATCACTTTC  AAAAGTCCGA   1380

AAGAATCTGC  TCCCTGCTTG  TGTGTTGGAG  GTCGCTGAGT  AGTGCGCGAG  TAAAATTTAA   1440

GCTACAACAA  GGCAAGGCTT  GACCGACAAT  TGCATGAAGA  ATCTGCTTAG  GGTTAGGCGT   1500

TTTGCGCTGC  TTCGCGATGT  ACGGGCCAGA  TATACGCGTT  GACATTGATT  ATTGACTAGT   1560

TATTAATAGT  AATCAATTAC  GGGGTCATTA  GTTCATAGCC  CATATATGGA  GTTCCGCGTT   1620

ACATAACTTA  CGGTAAATGG  CCCGCCTGGC  TGACCGCCCA  ACGACCCCCG  CCCATTGACG   1680

TCAATAATGA  CGTATGTTCC  CATAGTAACG  CCAATAGGGA  CTTTCCATTG  ACGTCAATGG   1740

GTGGACTATT  TACGGTAAAC  TGCCCACTTG  GCAGTACATC  AAGTGTATCA  TATGCCAAGT   1800

ACGCCCCTA   TTGACGTCAA  TGACGGTAAA  TGGCCCGCCT  GGCATTATGC  CCAGTACATG   1860

ACCTTATGGG  ACTTTCCTAC  TTGGCAGTAC  ATCTACGTAT  TAGTCATCGC  TATTACCATG   1920

GTGATGCGGT  TTTGGCAGTA  CATCAATGGG  CGTGGATAGC  GGTTTGACTC  ACGGGGATTT   1980

CCAAGTCTCC  ACCCCATTGA  CGTCAATGGG  AGTTTGTTTT  GGCACCAAAA  TCAACGGGAC   2040

TTTCCAAAAT  GTCGTAACAA  CTCCGCCCCA  TTGACGCAAA  TGGGCGGTAG  GCGTGTACGG   2100

TGGGAGGTCT  ATATAAGCAG  AGCTCTCTGG  CTAACTAGAG  AACCCACTGC  TTAACTGGCT   2160

TATCGAAATT  AATACGACTC  ACTATAGGGA  GACCGGAAGC  TTGGTACCGA  GCTCGGATCT   2220

GCCACC ATG GCA ACA GGA TCA AGA ACA TCA CTG CTG CTG GCA TTT GGA           2268
       Met Ala Thr Gly Ser Arg Thr Ser Leu Leu Leu Ala Phe Gly
       1               5                   10

CTG CTG TGT CTG CCA TGG CTG CAA GAA GGA TCA GCA GCA GCA GCA GCG           2316
Leu Leu Cys Leu Pro Trp Leu Gln Glu Gly Ser Ala Ala Ala Ala Ala
15                  20                  25                  30

AAT TCA GAA ACC CAC GTC ACC GGG GGA AGT GCC GGC CAC ACC ACG GCT           2364
Asn Ser Glu Thr His Val Thr Gly Gly Ser Ala Gly His Thr Thr Ala
                35                  40                  45

GGG CTT GTT CGT CTC CTT TCA CCA GGC GCC AAG CAG AAC ATC CAA CTG           2412
Gly Leu Val Arg Leu Leu Ser Pro Gly Ala Lys Gln Asn Ile Gln Leu
            50                  55                  60

ATC AAC ACC AAC GGC AGT TGG CAC ATC AAT AGC ACG GCC TTG AAC TGC           2460
Ile Asn Thr Asn Gly Ser Trp His Ile Asn Ser Thr Ala Leu Asn Cys
        65                  70                  75

AAT GAA AGC CTT AAC ACC GGC TGG TTA GCA GGG CTC TTC TAT CAC CAC           2508
Asn Glu Ser Leu Asn Thr Gly Trp Leu Ala Gly Leu Phe Tyr His His
    80                  85                  90

AAA TTC AAC TCT TCA GGT TGT CCT GAG AGG TTG GCC AGC TGC CGA CGC           2556
Lys Phe Asn Ser Ser Gly Cys Pro Glu Arg Leu Ala Ser Cys Arg Arg
95                  100                 105                 110

CTT ACC GAT TTT GCC CAG GGC GGG GGT CCT ATC AGT TAC GCC AAC GGA           2604
```

| | | | | | | | | | | | | | | | |
|---|---|---|---|---|---|---|---|---|---|---|---|---|---|---|---|
| Leu | Thr | Asp | Phe | Ala | Gln | Gly | Gly | Gly | Pro | Ile | Ser | Tyr | Ala | Asn | Gly |
| | | | | 115 | | | | 120 | | | | | | 125 | |

| | | | | | | | | | | | | | | | | |
|---|---|---|---|---|---|---|---|---|---|---|---|---|---|---|---|---|
| AGC | GGC | CTC | GAT | GAA | CGC | CCC | TAC | TGC | TGG | CAC | TAC | CCT | CCA | AGA | CCT | 2652 |
| Ser | Gly | Leu | Asp | Glu | Arg | Pro | Tyr | Cys | Trp | His | Tyr | Pro | Pro | Arg | Pro | |
| | | | 130 | | | | | 135 | | | | | 140 | | | |
| TGT | GGC | ATT | GTG | CCC | GCA | AAG | AGC | GTG | TGT | GGC | CCG | GTA | TAT | TGC | TTC | 2700 |
| Cys | Gly | Ile | Val | Pro | Ala | Lys | Ser | Val | Cys | Gly | Pro | Val | Tyr | Cys | Phe | |
| | | 145 | | | | | 150 | | | | | 155 | | | | |
| ACT | CCC | AGC | CCC | GTG | GTG | GTG | GGA | ACG | ACC | GAC | AGG | TCG | GGC | GCG | CCT | 2748 |
| Thr | Pro | Ser | Pro | Val | Val | Val | Gly | Thr | Thr | Asp | Arg | Ser | Gly | Ala | Pro | |
| | 160 | | | | | 165 | | | | | 170 | | | | | |
| ACC | TAC | AGC | TGG | GGT | GCA | AAT | GAT | ACG | GAT | GTC | TTT | GTC | CTT | AAC | AAC | 2796 |
| Thr | Tyr | Ser | Trp | Gly | Ala | Asn | Asp | Thr | Asp | Val | Phe | Val | Leu | Asn | Asn | |
| 175 | | | | | 180 | | | | | 185 | | | | | 190 | |
| ACC | AGG | CCA | CCG | CTG | GGC | AAT | TGG | TTC | GGT | TGC | ACC | TGG | ATG | AAC | TCA | 2844 |
| Thr | Arg | Pro | Pro | Leu | Gly | Asn | Trp | Phe | Gly | Cys | Thr | Trp | Met | Asn | Ser | |
| | | | | 195 | | | | | 200 | | | | | 205 | | |
| ACT | GGA | TTC | ACC | AAA | GTG | TGC | GGA | GCG | CCC | CCT | TGT | GTC | ATC | GGA | GGG | 2892 |
| Thr | Gly | Phe | Thr | Lys | Val | Cys | Gly | Ala | Pro | Pro | Cys | Val | Ile | Gly | Gly | |
| | | | 210 | | | | | 215 | | | | | 220 | | | |
| GTG | GGC | AAC | AAC | ACC | TTG | CTC | TGC | CCC | ACT | GAT | TGC | TTC | CGC | AAG | CAT | 2940 |
| Val | Gly | Asn | Asn | Thr | Leu | Leu | Cys | Pro | Thr | Asp | Cys | Phe | Arg | Lys | His | |
| | | 225 | | | | | 230 | | | | | 235 | | | | |
| CCG | GAA | GCC | ACA | TAC | TCT | CGG | TGC | GGC | TCC | GGT | CCC | TGG | ATT | ACA | CCC | 2988 |
| Pro | Glu | Ala | Thr | Tyr | Ser | Arg | Cys | Gly | Ser | Gly | Pro | Trp | Ile | Thr | Pro | |
| | 240 | | | | | 245 | | | | | 250 | | | | | |
| AGG | TGC | ATG | GTC | GAC | TAC | CCG | TAT | AGG | CTT | TGG | CAC | TAT | CCT | TGT | ACC | 3036 |
| Arg | Cys | Met | Val | Asp | Tyr | Pro | Tyr | Arg | Leu | Trp | His | Tyr | Pro | Cys | Thr | |
| 255 | | | | | 260 | | | | | 265 | | | | | 270 | |
| ATC | AAT | TAC | ACC | ATA | TTC | AAA | GTC | AGG | ATG | TAC | GTG | GGA | GGG | GTC | GAG | 3084 |
| Ile | Asn | Tyr | Thr | Ile | Phe | Lys | Val | Arg | Met | Tyr | Val | Gly | Gly | Val | Glu | |
| | | | | 275 | | | | | 280 | | | | | 285 | | |
| CAC | AGG | CTG | GAA | GCG | GCC | TGC | AAC | TGG | ACG | CGG | GGC | GAA | CGC | TGT | GAT | 3132 |
| His | Arg | Leu | Glu | Ala | Ala | Cys | Asn | Trp | Thr | Arg | Gly | Glu | Arg | Cys | Asp | |
| | | | 290 | | | | | 295 | | | | | 300 | | | |
| CTG | GAA | GAC | AGG | GAC | AGG | TCC | GAG | CTC | AGC | CCG | TTA | CTG | CTG | TCC | ACC | 3180 |
| Leu | Glu | Asp | Arg | Asp | Arg | Ser | Glu | Leu | Ser | Pro | Leu | Leu | Leu | Ser | Thr | |
| | | | 305 | | | | | 310 | | | | | 315 | | | |
| ACG | CAG | TGG | CAG | GTC | CTT | CCG | TGT | TCT | TTC | ACG | ACC | CTG | CCA | GCC | TTG | 3228 |
| Thr | Gln | Trp | Gln | Val | Leu | Pro | Cys | Ser | Phe | Thr | Thr | Leu | Pro | Ala | Leu | |
| | 320 | | | | | 325 | | | | | 330 | | | | | |
| TCC | ACC | GGC | CTC | ATC | CAC | CTC | CAC | CAG | AAC | ATT | GTG | GAC | GTG | CAG | TAC | 3276 |
| Ser | Thr | Gly | Leu | Ile | His | Leu | His | Gln | Asn | Ile | Val | Asp | Val | Gln | Tyr | |
| 335 | | | | | 340 | | | | | 345 | | | | | 350 | |
| TTG | TAC | GGG | GTA | GGG | TCA | AGC | ATC | GCG | TCC | TGG | GCT | ATT | AAG | TGG | GAG | 3324 |
| Leu | Tyr | Gly | Val | Gly | Ser | Ser | Ile | Ala | Ser | Trp | Ala | Ile | Lys | Trp | Glu | |
| | | | | 355 | | | | | 360 | | | | | 365 | | |
| TAC | GAC | GTT | CTC | CTG | TTC | CTT | CTG | CTT | GCA | GAC | GCG | CGC | GTT | TGC | TCC | 3372 |
| Tyr | Asp | Val | Leu | Leu | Phe | Leu | Leu | Leu | Ala | Asp | Ala | Arg | Val | Cys | Ser | |
| | | | 370 | | | | | 375 | | | | | 380 | | | |
| TGC | TTG | TGG | ATG | ATG | TTA | CTC | ATA | TCC | CAA | GCG | GAG | GCG | GCT | TTG | GAG | 3420 |
| Cys | Leu | Trp | Met | Met | Leu | Leu | Ile | Ser | Gln | Ala | Glu | Ala | Ala | Leu | Glu | |
| | | 385 | | | | | 390 | | | | | 395 | | | | |

```
AAC        TAATCTAGAG  GGCCCTATTC  TATAGTGTCA  CCTAAATGCT  AGAGGATCTT             3473
Asn

TGTGAAGGAA  CCTTACTTCT  GTGGTGTGAC  ATAATTGGAC  AAACTACCTA  CAGAGATTTA             3533

AAGCTCTAAG  GTAAATATAA  AATTTTTAAG  TGTATAATGT  GTTAAACTAC  TGATTCTAAT             3593

TGTTTGTGTA  TTTTAGATTC  CAACCTATGG  AACTGATGAA  TGGGAGCAGT  GGTGGAATGC             3653
```

| | | | | | |
|---|---|---|---|---|---|
| CTTTAATGAG | GAAAACCTGT | TTTGCTCAGA | AGAAATGCCA | TCTAGTGATG | ATGAGGCTAC | 3713 |
| TGCTGACTCT | CAACATTCTA | CTCCTCCAAA | AAAGAAGAGA | AAGGTAGAAG | ACCCCAAGGA | 3773 |
| CTTTCCTTCA | GAATTGCTAA | GTTTTTTGAG | TCATGCTGTG | TTTAGTAATA | GAACTCTTGC | 3833 |
| TTGCTTTGCT | ATTTACACCA | CAAAGGAAAA | AGCTGCACTG | CTATACAAGA | AAATTATGGA | 3893 |
| AAAATATTCT | GTAACCTTTA | TAAGTAGGCA | TAACAGTTAT | AATCATAACA | TACTGTTTTT | 3953 |
| TCTTACTCCA | CACAGGCATA | GAGTGTCTGC | TATTAATAAC | TATGCTCAAA | AATTGTGTAC | 4013 |
| CTTTAGCTTT | TTAATTTGTA | AAGGGGTTAA | TAAGGAATAT | TTGATGTATA | GTGCCTTGAC | 4073 |
| TAGAGATCAT | AATCAGCCAT | ACCACATTTG | TAGAGGTTTT | ACTTGCTTTA | AAAAACCTCC | 4133 |
| CACACCTCCC | CCTGAACCTG | AAACATAAAA | TGAATGCAAT | TGTTGTTGTT | AACTTGTTTA | 4193 |
| TTGCAGCTTA | TAATGGTTAC | AAATAAAGCA | ATAGCATCAC | AAATTTCACA | AATAAAGCAT | 4253 |
| TTTTTTCACT | GCATTCTAGT | TGTGGTTTGT | CCAAACTCAT | CAATGTATCT | TATCATGTCT | 4313 |
| GGATCGATCC | CGCCATGGTA | TCAACGCCAT | ATTTCTATTT | ACAGTAGGGA | CCTCTTCGTT | 4373 |
| GTGTAGGTAC | CGCTGTATTC | CTAGGGAAAT | AGTAGAGGCA | CCTTGAACTG | TCTGCATCAG | 4433 |
| CCATATAGCC | CCCGCTGTTC | GACTTACAAA | CACAGGCACA | GTACTGACAA | ACCCATACAC | 4493 |
| CTCCTCTGAA | ATACCCATAG | TTGCTAGGGC | TGTCTCCGAA | CTCATTACAC | CCTCCAAAGT | 4553 |
| CAGAGCTGTA | ATTTCGCCAT | CAAGGGCAGC | GAGGGCTTCT | CCAGATAAAA | TAGCTTCTGC | 4613 |
| CGAGAGTCCC | GTAAGGGTAG | ACACTTCAGC | TAATCCCTCG | ATGAGGTCTA | CTAGAATAGT | 4673 |
| CAGTGCGGCT | CCCATTTTGA | AAATTCACTT | ACTTGATCAG | CTTCAGAAGA | TGGCGGAGGG | 4733 |
| CCTCCAACAC | AGTAATTTTC | CTCCCGACTC | TTAAAATAGA | AAATGTCAAG | TCAGTTAAGC | 4793 |
| AGGAAGTGGA | CTAACTGACG | CAGCTGGCCG | TGCGACATCC | TCTTTTAATT | AGTTGCTAGG | 4853 |
| CAACGCCCTC | CAGAGGGCGT | GTGGTTTTGC | AAGAGGAAGC | AAAAGCCTCT | CCACCCAGGC | 4913 |
| CTAGAATGTT | TCCACCCAAT | CATTACTATG | ACAACAGCTG | TTTTTTTTAG | TATTAAGCAG | 4973 |
| AGGCCGGGGA | CCCCTGGCCC | GCTTACTCTG | GAGAAAAAGA | AGAGAGGCAT | TGTAGAGGCT | 5033 |
| TCCAGAGGCA | ACTTGTCAAA | ACAGGACTGC | TTCTATTTCT | GTCACACTGT | CTGGCCCTGT | 5093 |
| CACAAGGTCC | AGCACCTCCA | TACCCCCTTT | AATAAGCAGT | TTGGGAACGG | GTGCGGGTCT | 5153 |
| TACTCCGCCC | ATCCCGCCCC | TAACTCCGCC | CAGTTCCGCC | CATTCTCCGC | CCCATGGCTG | 5213 |
| ACTAATTTTT | TTTATTTATG | CAGAGGCCGA | GGCCGCCTCG | GCCTCTGAGC | TATTCCAGAA | 5273 |
| GTAGTGAGGA | GGCTTTTTTG | GAGGCCTAGG | CTTTTGCAAA | AAGCTAATTC | | 5323 |

( 2 ) INFORMATION FOR SEQ ID NO:10:

( i ) SEQUENCE CHARACTERISTICS:
        ( A ) LENGTH: 399 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met  Ala  Thr  Gly  Ser  Arg  Thr  Ser  Leu  Leu  Leu  Ala  Phe  Gly  Leu  Leu
  1                    5                   10                  15

Cys  Leu  Pro  Trp  Leu  Gln  Glu  Gly  Ser  Ala  Ala  Ala  Ala  Ala  Asn  Ser
                20                  25                  30

Glu  Thr  His  Val  Thr  Gly  Gly  Ser  Ala  Gly  His  Thr  Thr  Ala  Gly  Leu
            35                  40                  45

Val  Arg  Leu  Leu  Ser  Pro  Gly  Ala  Lys  Gln  Asn  Ile  Gln  Leu  Ile  Asn
        50                  55                  60
```

| | | | | | | | | | | | | | | | |
|---|---|---|---|---|---|---|---|---|---|---|---|---|---|---|---|
|Thr|Asn|Gly|Ser|Trp|His|Ile|Asn|Ser|Thr|Ala|Leu|Asn|Cys|Asn|Glu|
|65| | | |70| | | |75| | | | | | |80|
|Ser|Leu|Asn|Thr|Gly|Trp|Leu|Ala|Gly|Leu|Phe|Tyr|His|His|Lys|Phe|
| | | | |85| | | |90| | | | | |95| |
|Asn|Ser|Ser|Gly|Cys|Pro|Glu|Arg|Leu|Ala|Ser|Cys|Arg|Arg|Leu|Thr|
| | | |100| | | |105| | | | |110| | | |
|Asp|Phe|Ala|Gln|Gly|Gly|Gly|Pro|Ile|Ser|Tyr|Ala|Asn|Gly|Ser|Gly|
| | |115| | | | |120| | | | |125| | | |
|Leu|Asp|Glu|Arg|Pro|Tyr|Cys|Trp|His|Tyr|Pro|Pro|Arg|Pro|Cys|Gly|
| |130| | | | |135| | | | |140| | | | |
|Ile|Val|Pro|Ala|Lys|Ser|Val|Cys|Gly|Pro|Val|Tyr|Cys|Phe|Thr|Pro|
|145| | | | |150| | | | |155| | | | |160|
|Ser|Pro|Val|Val|Val|Gly|Thr|Thr|Asp|Arg|Ser|Gly|Ala|Pro|Thr|Tyr|
| | | | |165| | | | |170| | | | |175| |
|Ser|Trp|Gly|Ala|Asn|Asp|Thr|Asp|Val|Phe|Val|Leu|Asn|Asn|Thr|Arg|
| | | |180| | | | |185| | | | |190| | |
|Pro|Pro|Leu|Gly|Asn|Trp|Phe|Gly|Cys|Thr|Trp|Met|Asn|Ser|Thr|Gly|
| | |195| | | | |200| | | | |205| | | |
|Phe|Thr|Lys|Val|Cys|Gly|Ala|Pro|Pro|Cys|Val|Ile|Gly|Gly|Val|Gly|
| |210| | | | |215| | | | |220| | | | |
|Asn|Asn|Thr|Leu|Leu|Cys|Pro|Thr|Asp|Cys|Phe|Arg|Lys|His|Pro|Glu|
|225| | | | |230| | | | |235| | | | |240|
|Ala|Thr|Tyr|Ser|Arg|Cys|Gly|Ser|Gly|Pro|Trp|Ile|Thr|Pro|Arg|Cys|
| | | | |245| | | | |250| | | | |255| |
|Met|Val|Asp|Tyr|Pro|Tyr|Arg|Leu|Trp|His|Tyr|Pro|Cys|Thr|Ile|Asn|
| | | |260| | | | |265| | | | |270| | |
|Tyr|Thr|Ile|Phe|Lys|Val|Arg|Met|Tyr|Val|Gly|Gly|Val|Glu|His|Arg|
| | |275| | | | |280| | | | |285| | | |
|Leu|Glu|Ala|Ala|Cys|Asn|Trp|Thr|Arg|Gly|Glu|Arg|Cys|Asp|Leu|Glu|
| |290| | | | |295| | | | |300| | | | |
|Asp|Arg|Asp|Arg|Ser|Glu|Leu|Ser|Pro|Leu|Leu|Leu|Ser|Thr|Thr|Gln|
|305| | | | |310| | | | |315| | | | |320|
|Trp|Gln|Val|Leu|Pro|Cys|Ser|Phe|Thr|Thr|Leu|Pro|Ala|Leu|Ser|Thr|
| | | | |325| | | | |330| | | | |335| |
|Gly|Leu|Ile|His|Leu|His|Gln|Asn|Ile|Val|Asp|Val|Gln|Tyr|Leu|Tyr|
| | | |340| | | | |345| | | | |350| | |
|Gly|Val|Gly|Ser|Ser|Ile|Ala|Ser|Trp|Ala|Ile|Lys|Trp|Glu|Tyr|Asp|
| | |355| | | | |360| | | | |365| | | |
|Val|Leu|Leu|Phe|Leu|Leu|Leu|Ala|Asp|Ala|Arg|Val|Cys|Ser|Cys|Leu|
| |370| | | | |375| | | | |380| | | | |
|Trp|Met|Met|Leu|Leu|Ile|Ser|Gln|Ala|Glu|Ala|Leu|Glu|Asn| | |
|385| | | | |390| | | | |395| | | | | |

( 2 ) INFORMATION FOR SEQ ID NO:11:

( i ) SEQUENCE CHARACTERISTICS:
        ( A ) LENGTH: 5125 base pairs
        ( B ) TYPE: nucleic acid
        ( C ) STRANDEDNESS: single
        ( D ) TOPOLOGY: circular ( i i ) MOLECULE TYPE: DNA (genomic)

( i x ) FEATURE:
        ( A ) NAME/KEY: CDS
        ( B ) LOCATION: 2227..3225

( x i ) SEQUENCE DESCRIPTION: SEQ ID NO:11:

-continued

| | | | | | |
|---|---|---|---|---|---|
| GCGTAATCTG | CTGCTTGCAA | ACAAAAAAAC | CACCGCTACC | AGCGGTGGTT | TGTTTGCCGG | 60
| ATCAAGAGCT | ACCAACTCTT | TTTCCGAAGG | TAACTGGCTT | CAGCAGAGCG | CAGATACCAA | 120
| ATACTGTCCT | TCTAGTGTAG | CCGTAGTTAG | GCCACCACTT | CAAGAACTCT | GTAGCACCGC | 180
| CTACATACCT | CGCTCTGCTA | ATCCTGTTAC | CAGTGGCTGC | TGCCAGTGGC | GATAAGTCGT | 240
| GTCTTACCGG | GTTGGACTCA | AGACGATAGT | TACCGGATAA | GGCGCAGCGG | TCGGGCTGAA | 300
| CGGGGGGTTC | GTGCACACAG | CCCAGCTTGG | AGCGAACGAC | CTACACCGAA | CTGAGATACC | 360
| TACAGCGTGA | GCATTGAGAA | AGCGCCACGC | TTCCCGAAGG | GAGAAAGGCG | GACAGGTATC | 420
| CGGTAAGCGG | CAGGGTCGGA | ACAGGAGAGC | GCACGAGGGA | GCTTCCAGGG | GGAAACGCCT | 480
| GGTATCTTTA | TAGTCCTGTC | GGGTTTCGCC | ACCTCTGACT | TGAGCGTCGA | TTTTTGTGAT | 540
| GCTCGTCAGG | GGGGCGGAGC | CTATGGAAAA | ACGCCAGCAA | CGCAAGCTAG | CTTCTAGCTA | 600
| GAAATTGTAA | ACGTTAATAT | TTTGTTAAAA | TTCGCGTTAA | ATTTTTGTTA | AATCAGCTCA | 660
| TTTTTTAACC | AATAGGCCGA | AATCGGCAAA | ATCCCTTATA | AATCAAAAGA | ATAGCCCGAG | 720
| ATAGGGTTGA | GTGTTGTTCC | AGTTTGGAAC | AAGAGTCCAC | TATTAAAGAA | CGTGGACTCC | 780
| AACGTCAAAG | GGCGAAAAAC | CGTCTATCAG | GGCGATGGCC | GCCCACTACG | TGAACCATCA | 840
| CCCAAATCAA | GTTTTTTGGG | GTCGAGGTGC | CGTAAAGCAC | TAAATCGGAA | CCCTAAAGGG | 900
| AGCCCCCGAT | TTAGAGCTTG | ACGGGGAAAG | CCGGCGAACG | TGGCGAGAAA | GGAAGGGAAG | 960
| AAAGCGAAAG | GAGCGGGCGC | TAGGGCGCTG | GCAAGTGTAG | CGGTCACGCT | GCGCGTAACC | 1020
| ACCACACCCG | CCGCGCTTAA | TGCGCCGCTA | CAGGGCGCGT | ACTATGGTTG | CTTTGACGAG | 1080
| ACCGTATAAC | GTGCTTTCCT | CGTTGGAATC | AGAGCGGGAG | CTAAACAGGA | GGCCGATTAA | 1140
| AGGGATTTTA | GACAGGAACG | GTACGCCAGC | TGGATCACCG | CGGTCTTTCT | CAACGTAACA | 1200
| CTTTACAGCG | GCGCGTCATT | TGATATGATG | CGCCCCGCTT | CCCGATAAGG | GAGCAGGCCA | 1260
| GTAAAAGCAT | TACCCGTGGT | GGGGTTCCCG | AGCGGCCAAA | GGGAGCAGAC | TCTAAATCTG | 1320
| CCGTCATCGA | CTTCGAAGGT | TCGAATCCTT | CCCCCACCAC | CATCACTTTC | AAAAGTCCGA | 1380
| AAGAATCTGC | TCCCTGCTTG | TGTGTTGGAG | GTCGCTGAGT | AGTGCGCGAG | TAAAATTTAA | 1440
| GCTACAACAA | GGCAAGGCTT | GACCGACAAT | TGCATGAAGA | ATCTGCTTAG | GGTTAGGCGT | 1500
| TTTGCGCTGC | TTCGCGATGT | ACGGGCCAGA | TATACGCGTT | GACATTGATT | ATTGACTAGT | 1560
| TATTAATAGT | AATCAATTAC | GGGGTCATTA | GTTCATAGCC | CATATATGGA | GTTCCGCGTT | 1620
| ACATAACTTA | CGGTAAATGG | CCCGCCTGGC | TGACCGCCCA | ACGACCCCG | CCCATTGACG | 1680
| TCAATAATGA | CGTATGTTCC | CATAGTAACG | CCAATAGGGA | CTTTCCATTG | ACGTCAATGG | 1740
| GTGGACTATT | TACGGTAAAC | TGCCCACTTG | GCAGTACATC | AAGTGTATCA | TATGCCAAGT | 1800
| ACGCCCCCTA | TTGACGTCAA | TGACGGTAAA | TGGCCCGCCT | GGCATTATGC | CCAGTACATG | 1860
| ACCTTATGGG | ACTTTCCTAC | TTGGCAGTAC | ATCTACGTAT | TAGTCATCGC | TATTACCATG | 1920
| GTGATGCGGT | TTTGGCAGTA | CATCAATGGG | CGTGGATAGC | GGTTTGACTC | ACGGGGATTT | 1980
| CCAAGTCTCC | ACCCCATTGA | CGTCAATGGG | AGTTTGTTTT | GGCACCAAAA | TCAACGGGAC | 2040
| TTTCCAAAAT | GTCGTAACAA | CTCCGCCCCA | TTGACGCAAA | TGGGCGGTAG | GCGTGTACGG | 2100
| TGGGAGGTCT | ATATAAGCAG | AGCTCTCTGG | CTAACTAGAG | AACCCACTGC | TTAACTGGCT | 2160
| TATCGAAATT | AATACGACTC | ACTATAGGGA | GACCGGAAGC | TTGGTACCGA | GCTCGGATCT | 2220
| GCCACC ATG | GCA ACA GGA | TCA AGA ACA | TCA CTG CTG | CTG GCA TTT GGA | | 2268
| | Met Ala Thr Gly | Ser Arg Thr | Ser Leu Leu | Leu Ala Phe Gly | |
| | 1 | 5 | | 10 | |
| CTG CTG TGT CTG | CCA TGG CTG | CAA GAA GGA | TCA GCA GCA | GCA GCG | | 2316
| Leu Leu Cys Leu | Pro Trp Leu | Gln Glu Gly | Ser Ala Ala | Ala Ala Ala | |

-continued

| | | 15 | | | | 20 | | | | 25 | | | | 30 | | |
|---|---|---|---|---|---|---|---|---|---|---|---|---|---|---|---|---|
| AAT | TCA | GAA | ACC | CAC | GTC | ACC | GGG | GGA | AGT | GCC | GGC | CAC | ACC | ACG | GCT | 2364 |
| Asn | Ser | Glu | Thr | His | Val | Thr | Gly | Gly | Ser | Ala | Gly | His | Thr | Thr | Ala | |
| | | 35 | | | | | | 40 | | | | | 45 | | | |
| GGG | CTT | GTT | CGT | CTC | CTT | TCA | CCA | GGC | GCC | AAG | CAG | AAC | ATC | CAA | CTG | 2412 |
| Gly | Leu | Val | Arg | Leu | Leu | Ser | Pro | Gly | Ala | Lys | Gln | Asn | Ile | Gln | Leu | |
| | | | 50 | | | | | 55 | | | | | 60 | | | |
| ATC | AAC | ACC | AAC | GGC | AGT | TGG | CAC | ATC | AAT | AGC | ACG | GCC | TTG | AAC | TGC | 2460 |
| Ile | Asn | Thr | Asn | Gly | Ser | Trp | His | Ile | Asn | Ser | Thr | Ala | Leu | Asn | Cys | |
| | | 65 | | | | | 70 | | | | | 75 | | | | |
| AAT | GAA | AGC | CTT | AAC | ACC | GGC | TGG | TTA | GCA | GGG | CTC | TTC | TAT | CAC | CAC | 2508 |
| Asn | Glu | Ser | Leu | Asn | Thr | Gly | Trp | Leu | Ala | Gly | Leu | Phe | Tyr | His | His | |
| | | 80 | | | | 85 | | | | | 90 | | | | | |
| AAA | TTC | AAC | TCT | TCA | GGT | TGT | CCT | GAG | AGG | TTG | GCC | AGC | TGC | CGA | CGC | 2556 |
| Lys | Phe | Asn | Ser | Ser | Gly | Cys | Pro | Glu | Arg | Leu | Ala | Ser | Cys | Arg | Arg | |
| 95 | | | | | 100 | | | | | 105 | | | | | 110 | |
| CTT | ACC | GAT | TTT | GCC | CAG | GGC | GGG | GGT | CCT | ATC | AGT | TAC | GCC | AAC | GGA | 2604 |
| Leu | Thr | Asp | Phe | Ala | Gln | Gly | Gly | Gly | Pro | Ile | Ser | Tyr | Ala | Asn | Gly | |
| | | | | 115 | | | | | 120 | | | | | 125 | | |
| AGC | GGC | CTC | GAT | GAA | CGC | CCC | TAC | TGC | TGG | CAC | TAC | CCT | CCA | AGA | CCT | 2652 |
| Ser | Gly | Leu | Asp | Glu | Arg | Pro | Tyr | Cys | Trp | His | Tyr | Pro | Pro | Arg | Pro | |
| | | | 130 | | | | | 135 | | | | | 140 | | | |
| TGT | GGC | ATT | GTG | CCC | GCA | AAG | AGC | GTG | TGT | GGC | CCG | GTA | TAT | TGC | TTC | 2700 |
| Cys | Gly | Ile | Val | Pro | Ala | Lys | Ser | Val | Cys | Gly | Pro | Val | Tyr | Cys | Phe | |
| | | 145 | | | | | 150 | | | | | 155 | | | | |
| ACT | CCC | AGC | CCC | GTG | GTG | GTG | GGA | ACG | ACC | GAC | AGG | TCG | GGC | GCG | CCT | 2748 |
| Thr | Pro | Ser | Pro | Val | Val | Val | Gly | Thr | Thr | Asp | Arg | Ser | Gly | Ala | Pro | |
| | 160 | | | | | 165 | | | | | 170 | | | | | |
| ACC | TAC | AGC | TGG | GGT | GCA | AAT | GAT | ACG | GAT | GTC | TTT | GTC | CTT | AAC | AAC | 2796 |
| Thr | Tyr | Ser | Trp | Gly | Ala | Asn | Asp | Thr | Asp | Val | Phe | Val | Leu | Asn | Asn | |
| 175 | | | | | 180 | | | | | 185 | | | | | 190 | |
| ACC | AGG | CCA | CCG | CTG | GGC | AAT | TGG | TTC | GGT | TGC | ACC | TGG | ATG | AAC | TCA | 2844 |
| Thr | Arg | Pro | Pro | Leu | Gly | Asn | Trp | Phe | Gly | Cys | Thr | Trp | Met | Asn | Ser | |
| | | | | 195 | | | | | 200 | | | | | 205 | | |
| ACT | GGA | TTC | ACC | AAA | GTG | TGC | GGA | GCG | CCC | CCT | TGT | GTC | ATC | GGA | GGG | 2892 |
| Thr | Gly | Phe | Thr | Lys | Val | Cys | Gly | Ala | Pro | Pro | Cys | Val | Ile | Gly | Gly | |
| | | | 210 | | | | | 215 | | | | | 220 | | | |
| GTG | GGC | AAC | AAC | ACC | TTG | CTC | TGC | CCC | ACT | GAT | TGC | TTC | CGC | AAG | CAT | 2940 |
| Val | Gly | Asn | Asn | Thr | Leu | Leu | Cys | Pro | Thr | Asp | Cys | Phe | Arg | Lys | His | |
| | | 225 | | | | | 230 | | | | | 235 | | | | |
| CCG | GAA | GCC | ACA | TAC | TCT | CGG | TGC | GGC | TCC | GGT | CCC | TGG | ATT | ACA | CCC | 2988 |
| Pro | Glu | Ala | Thr | Tyr | Ser | Arg | Cys | Gly | Ser | Gly | Pro | Trp | Ile | Thr | Pro | |
| | 240 | | | | | 245 | | | | | 250 | | | | | |
| AGG | TGC | ATG | GTC | GAC | TAC | CCG | TAT | AGG | CTT | TGG | CAC | TAT | CCT | TGT | ACC | 3036 |
| Arg | Cys | Met | Val | Asp | Tyr | Pro | Tyr | Arg | Leu | Trp | His | Tyr | Pro | Cys | Thr | |
| 255 | | | | | 260 | | | | | 265 | | | | | 270 | |
| ATC | AAT | TAC | ACC | ATA | TTC | AAA | GTC | AGG | ATG | TAC | GTG | GGA | GGG | GTC | GAG | 3084 |
| Ile | Asn | Tyr | Thr | Ile | Phe | Lys | Val | Arg | Met | Tyr | Val | Gly | Gly | Val | Glu | |
| | | | | 275 | | | | | 280 | | | | | 285 | | |
| CAC | AGG | CTG | GAA | GCG | GCC | TGC | AAC | TGG | ACG | CGG | GGC | GAA | CGC | TGT | GAT | 3132 |
| His | Arg | Leu | Glu | Ala | Ala | Cys | Asn | Trp | Thr | Arg | Gly | Glu | Arg | Cys | Asp | |
| | | | 290 | | | | | 295 | | | | | 300 | | | |
| CTG | GAA | GAC | AGG | GAC | AGG | TCC | GAG | CTC | AGC | CCG | TTA | CTG | CTG | TCC | ACC | 3180 |
| Leu | Glu | Asp | Arg | Asp | Arg | Ser | Glu | Leu | Ser | Pro | Leu | Leu | Leu | Ser | Thr | |
| | | 305 | | | | | 310 | | | | | 315 | | | | |
| ACG | CAG | TGG | CAG | GTC | CTT | CCG | TGT | TCT | TTC | ACG | ACC | CTG | CCA | GCC | | 3225 |
| Thr | Gln | Trp | Gln | Val | Leu | Pro | Cys | Ser | Phe | Thr | Thr | Leu | Pro | Ala | | |
| | 320 | | | | | 325 | | | | | 330 | | | | | |

TAATCTAGAG GGCCCTATTC TATAGTGTCA CCTAAATGCT AGAGGATCTT TGTGAAGGAA    3285

```
CCTTACTTCT  GTGGTGTGAC  ATAATTGGAC  AAACTACCTA  CAGAGATTTA  AAGCTCTAAG    3345

GTAAATATAA  AATTTTTAAG  TGTATAATGT  GTTAAACTAC  TGATTCTAAT  TGTTTGTGTA    3405

TTTTAGATTC  CAACCTATGG  AACTGATGAA  TGGGAGCAGT  GGTGGAATGC  CTTTAATGAG    3465

GAAAACCTGT  TTTGCTCAGA  AGAAATGCCA  TCTAGTGATG  ATGAGGCTAC  TGCTGACTCT    3525

CAACATTCTA  CTCCTCCAAA  AAAGAAGAGA  AAGGTAGAAG  ACCCCAAGGA  CTTTCCTTCA    3585

GAATTGCTAA  GTTTTTTGAG  TCATGCTGTG  TTTAGTAATA  GAACTCTTGC  TTGCTTTGCT    3645

ATTTACACCA  CAAAGGAAAA  AGCTGCACTG  CTATACAAGA  AAATTATGGA  AAAATATTCT    3705

GTAACCTTTA  TAAGTAGGCA  TAACAGTTAT  AATCATAACA  TACTGTTTTT  TCTTACTCCA    3765

CACAGGCATA  GAGTGTCTGC  TATTAATAAC  TATGCTCAAA  AATTGTGTAC  CTTTAGCTTT    3825

TTAATTTGTA  AAGGGGTTAA  TAAGGAATAT  TTGATGTATA  GTGCCTTGAC  TAGAGATCAT    3885

AATCAGCCAT  ACCACATTTG  TAGAGGTTTT  ACTTGCTTTA  AAAAACCTCC  CACACCTCCC    3945

CCTGAACCTG  AAACATAAAA  TGAATGCAAT  TGTTGTTGTT  AACTTGTTTA  TTGCAGCTTA    4005

TAATGGTTAC  AAATAAAGCA  ATAGCATCAC  AAATTTCACA  AATAAAGCAT  TTTTTCACT    4065

GCATTCTAGT  TGTGGTTTGT  CCAAACTCAT  CAATGTATCT  TATCATGTCT  GGATCGATCC    4125

CGCCATGGTA  TCAACGCCAT  ATTTCTATTT  ACAGTAGGGA  CCTCTTCGTT  GTGTAGGTAC    4185

CGCTGTATTC  CTAGGGAAAT  AGTAGAGGCA  CCTTGAACTG  TCTGCATCAG  CCATATAGCC    4245

CCCGCTGTTC  GACTTACAAA  CACAGGCACA  GTACTGACAA  ACCCATACAC  CTCCTCTGAA    4305

ATACCCATAG  TTGCTAGGGC  TGTCTCCGAA  CTCATTACAC  CCTCCAAAGT  CAGAGCTGTA    4365

ATTTCGCCAT  CAAGGGCAGC  GAGGGCTTCT  CCAGATAAAA  TAGCTTCTGC  CGAGAGTCCC    4425

GTAAGGGTAG  ACACTTCAGC  TAATCCCTCG  ATGAGGTCTA  CTAGAATAGT  CAGTGCGGCT    4485

CCCATTTTGA  AAATTCACTT  ACTTGATCAG  CTTCAGAAGA  TGGCGGAGGG  CCTCCAACAC    4545

AGTAATTTTC  CTCCCGACTC  TTAAAATAGA  AAATGTCAAG  TCAGTTAAGC  AGGAAGTGGA    4605

CTAACTGACG  CAGCTGGCCG  TGCGACATCC  TCTTTTAATT  AGTTGCTAGG  CAACGCCCTC    4665

CAGAGGGCGT  GTGGTTTTGC  AAGAGGAAGC  AAAAGCCTCT  CCACCCAGGC  CTAGAATGTT    4725

TCCACCCAAT  CATTACTATG  ACAACAGCTG  TTTTTTTTAG  TATTAAGCAG  AGGCCGGGGA    4785

CCCCTGGCCC  GCTTACTCTG  GAGAAAAAGA  AGAGAGGCAT  TGTAGAGGCT  TCCAGAGGCA    4845

ACTTGTCAAA  ACAGGACTGC  TTCTATTTCT  GTCACACTGT  CTGGCCCTGT  CACAAGGTCC    4905

AGCACCTCCA  TACCCCCTTT  AATAAGCAGT  TTGGGAACGG  GTGCGGGTCT  TACTCCGCCC    4965

ATCCCGCCCC  TAACTCCGCC  CAGTTCCGCC  CATTCTCCGC  CCCATGGCTG  ACTAATTTTT    5025

TTTATTTATG  CAGAGGCCGA  GGCCGCCTCG  GCCTCTGAGC  TATTCCAGAA  GTAGTGAGGA    5085

GGCTTTTTTG  GAGGCCTAGG  CTTTTGCAAA  AAGCTAATTC                            5125
```

( 2 ) INFORMATION FOR SEQ ID NO:12:

( i ) SEQUENCE CHARACTERISTICS:
        ( A ) LENGTH: 333 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met  Ala  Thr  Gly  Ser  Arg  Thr  Ser  Leu  Leu  Leu  Ala  Phe  Gly  Leu  Leu
 1              5                        10                       15

Cys  Leu  Pro  Trp  Leu  Gln  Glu  Gly  Ser  Ala  Ala  Ala  Ala  Ala  Asn  Ser
            20                       25                       30
```

-continued

| | | | | | | | | | | | | | | |
|---|---|---|---|---|---|---|---|---|---|---|---|---|---|---|
| Glu | Thr | His 35 | Val | Thr | Gly | Gly | Ser 40 | Ala | Gly | His | Thr | Thr 45 | Ala | Gly | Leu |
| Val | Arg 50 | Leu | Leu | Ser | Pro | Gly 55 | Ala | Lys | Gln | Asn | Ile 60 | Gln | Leu | Ile | Asn |
| Thr 65 | Asn | Gly | Ser | Trp | His 70 | Ile | Asn | Ser | Thr | Ala 75 | Leu | Asn | Cys | Asn | Glu 80 |
| Ser | Leu | Asn | Thr | Gly 85 | Trp | Leu | Ala | Gly | Leu 90 | Phe | Tyr | His | His | Lys 95 | Phe |
| Asn | Ser | Ser | Gly 100 | Cys | Pro | Glu | Arg | Leu 105 | Ala | Ser | Cys | Arg | Arg 110 | Leu | Thr |
| Asp | Phe | Ala 115 | Gln | Gly | Gly | Gly | Pro 120 | Ile | Ser | Tyr | Ala | Asn 125 | Gly | Ser | Gly |
| Leu | Asp 130 | Glu | Arg | Pro | Tyr | Cys 135 | Trp | His | Tyr | Pro | Pro 140 | Arg | Pro | Cys | Gly |
| Ile 145 | Val | Pro | Ala | Lys | Ser 150 | Val | Cys | Gly | Pro | Val 155 | Tyr | Cys | Phe | Thr | Pro 160 |
| Ser | Pro | Val | Val | Val 165 | Gly | Thr | Thr | Asp | Arg 170 | Ser | Gly | Ala | Pro | Thr 175 | Tyr |
| Ser | Trp | Gly | Ala 180 | Asn | Asp | Thr | Asp | Val 185 | Phe | Val | Leu | Asn | Asn 190 | Thr | Arg |
| Pro | Pro | Leu 195 | Gly | Asn | Trp | Phe | Gly 200 | Cys | Thr | Trp | Met | Asn 205 | Ser | Thr | Gly |
| Phe | Thr 210 | Lys | Val | Cys | Gly | Ala 215 | Pro | Pro | Cys | Val | Ile 220 | Gly | Gly | Val | Gly |
| Asn 225 | Asn | Thr | Leu | Leu | Cys 230 | Pro | Thr | Asp | Cys | Phe 235 | Arg | Lys | His | Pro | Glu 240 |
| Ala | Thr | Tyr | Ser | Arg 245 | Cys | Gly | Ser | Gly | Pro 250 | Trp | Ile | Thr | Pro | Arg 255 | Cys |
| Met | Val | Asp | Tyr 260 | Pro | Tyr | Arg | Leu | Trp 265 | His | Tyr | Pro | Cys | Thr 270 | Ile | Asn |
| Tyr | Thr | Ile 275 | Phe | Lys | Val | Arg | Met 280 | Tyr | Val | Gly | Gly | Val 285 | Glu | His | Arg |
| Leu | Glu 290 | Ala | Ala | Cys | Asn | Trp 295 | Thr | Arg | Gly | Glu | Arg 300 | Cys | Asp | Leu | Glu |
| Asp 305 | Arg | Asp | Arg | Ser | Glu 310 | Leu | Ser | Pro | Leu | Leu 315 | Leu | Ser | Thr | Thr | Gln 320 |
| Trp | Gln | Val | Leu | Pro 325 | Cys | Ser | Phe | Thr | Thr 330 | Leu | Pro | Ala | | | |

HEPATITIS C VIRUS FUSION PROTEINS

This application is a continuation of application Ser. No. 08/417,478 filed Apr. 5, 1995 now abandoned, which is a continuation of application Ser. No. 08/144,099 filed Oct. 28, 1993 now abandoned, which is a continuation of application Ser. No. 07/830,024 filed Jan. 31, 1992 now abandoned.

BACKGROUND OF THE INVENTION

This invention relates generally to Hepatitis C Virus (HCV), and more particularly, relates to mammalian expression systems capable of generating HCV proteins and uses of these proteins.

Descriptions of Hepatitis diseases causing jaundice and icterus have been known to man since antiquity. Viral hepatitis is now known to include a group of viral agents with distinctive viral organization protein structure and mode of replication, causing hepatitis with different degrees of severity of hepatic damage through different routes of transmission. Acute viral hepatitis is clinically diagnosed by well-defined patient symptoms including jaundice, hepatic tenderness and an elevated level of liver transaminases such as Aspartate Transaminase and Alanine Transaminase.

Serological assays currently are employed to further distinguish between Hepatitis-A and Hepatitis-B. Non-A Non-B Hepatitis (NANBH) is a term first used in 1975 that described cases of post-transfusion hepatitis not caused by either Hepatitis A Virus or Hepatitis B Virus. Feinstone et al., *New Engl. J. Med.* 292:454–457 (1975). The diagnosis of NANBH has been made primarily by means of exclusion on the basis of serological analysis for the presence of Hepatitis A and Hepatitis B. NANBH is responsible for about 90% of the cases of post-transfusion hepatitis. Hollinger et al. in N. R. Rose et al., eds., *Manual of Clinical Immunology*, American Society for Microbiology, Washington, D.C., 558–572 (1986).

Attempts to identify the NANBH virus by virtue of genomic similarity to one of the known hepatitis viruses have failed thus far, suggesting that NANBH has a distinctive genomic organization and structure. Fowler et al., *J. Med. Virol.* 12:205–213 (1983), and Weiner et al., *J. Med. Virol.* 21:239–247 (1987). Progress in developing assays to detect antibodies specific for NANBH has been hampered by difficulties encountered in identifying antigens associated with the virus. Wands et al., U.S. Pat. No. 4,870,076; Wands et al., *Proc. Natl. Acad. Sci.* 83:6608–6612 (1986); Ohori et al., *J. Med. Virol.* 12:161–178 (1983); Bradley et al., *Proc. Natl. Acad. Sci.* 84:6277–6281 (1987); Akatsuka et al., *J. Med. Virol.* 20:43–56 (1986).

In May of 1988, a collaborative effort of Chiron Corporation with the Centers for Disease Control resulted in the identification of a putative NANB agent, Hepatitis C Virus (HCV). M. Houghton et al. cloned and expressed in *E. coli* a NANB agent obtained from the infectious plasma of a chimp. Kuo et al., *Science* 244:359–361 (1989); Choo et al., *Science* 244:362–364 (1989). CDNA sequences from HCV were identified which encode antigens that react immunologically with antibodies present in a majority of the patients clinically diagnosed with NANBH. Based on the information available and on the molecular structure of HCV, the genetic makeup of the virus consists of single stranded linear RNA (positive strand) of molecular weight approximately 9.5 kb, and possessing one continuous translational open reading frame. J. A. Cuthbert, *Amer. J. Med. Sci.* 299:346–355 (1990). It is a small enveloped virus resembling the Flaviviruses. Investigators have made attempts to identify the NANB agent by ultrastructural changes in hepatocytes in infected individuals. H, Gupta, *Liver* 8:111–115 (1988); D. W. Bradley *J. Virol. Methods* 10:307–319 (1985). Similar ultrastructural changes in hepatocytes as well as PCR amplified HCV RNA sequences have been detected in NANBH patients as well as in chimps experimentally infected with infectious HCV plasma. T. Shimizu et al., *Proc. Natl. Acad. Sci.* 87:6441–6444 (1990).

Considerable serological evidence has been found to implicate HCV as the etiological agent for post-transfusion NANBH. H. Alter et al., *N. Eng. J. Med.* 321:1494–1500 (1989); Estaben et al., *The Lancet:* Aug. 5:294–296 (1989); C. Van Der Poel et al., *The Lancet* Aug. 5:297–298 (1989); G. Sbolli, *J. Med. Virol.* 30:230–232 (1990); M. Makris et al., *The Lancet* 335:1117–1119 (1990). Although the detection of HCV antibodies eliminates 70 to 80% of NANBH infected blood from the blood supply system, the antibodies apparently are readily detected during the chronic state of the disease, while only 60% of the samples from the acute NANBH stage are HCV antibody positive. H. Alter et al., *New Eng. J. Med.* 321:1994–1500 (1989). The prolonged interval between exposure to HCV and antibody detection, and the lack of adequate information regarding the profile of immune response to various structural and non-structural proteins raises questions regarding the infectious state of the patient in the latent and antibody negative phase during NANBH infection.

Since discovery of the putative HCV etiological agent as discussed supra, investigators have attempted to express the putative HCV proteins in human expression systems and also to isolate the virus. To date, no report has been published in which HCV has been expressed efficiently in mammalian expression systems, and the virus has not been propagated in tissue culture systems.

Therefore, there is a need for the development of assay reagents and assay systems to identify acute infection and viremia which may be present, and not currently detected by commercially-available assays. These tools are needed to help distinguish between acute and persistent, on-going and/or chronic infection from those likely to be resolved, and to define the prognostic course of NANBH infection, in order to develop preventive and/or therapeutic strategies. Also, the expression systems that allow for secretion of these glycosylated antigens would be helpful to purify and manufacture diagnostic and therapeutic reagents.

SUMMARY OF THE INVENTION

This invention provides novel mammalian expression systems that are capable of generating high levels of expressed proteins of HCV. In particular, full-length structural fragments of HCV are expressed as a fusion with the Amyloid Precursor Protein (APP) or Human Growth Hormone (HGH) secretion signal. These unique expression systems allow for the production of high levels of HCV proteins, contributing to the proper processing, gycolsylation and folding of the viral protein(s) in the system. In particular, the present invention provides the plasmids pHCV-162, pHCV-167, pHCV-168, pHCV-169 and pHCV-170. The APP-HCV-E2 fusion proteins expressed by mammalian expression vectors pHCV-162 and pHCV-167 also are included. Further, HGH-HCV-E2 fusion proteins expressed by a mammalian expression vectors pHCV-168, pHCV-169 and pHCV-170 are provided.

The present invention also provides a method for detecting HCV antigen or antibody in a test sample suspected of containing HCV antigen or antibody, wherein the improvement comprises contacting the test sample with a glycosylated HCV antigen produced in a mammalian expression system. Also provided is a method for detecting HCV antigen or antibody in a test sample suspected of containing HCV antigen or antibody, wherein the improvement comprises contacting the test sample with an antibody produced by using a glycosylated HCV antigen produced in a mammalian expression system. The antibody can be monoclonal or polyclonal.

The present invention further provides a test kit for detecting the presence of HCV antigen or HCV antigen in a test sample suspected of containing said HCV antigen or antibody, comprising a container containing a glycosylated HCV antigen produced in a mammalian expression system. The test kit also can include an antibody produced by using a glycosylated HCV antigen produced in a mammalian expression system. Another test kit provided by the present invention comprises a container containing an antibody produced by using a glycosylated HCV antigen produced in a mammalian expression system. The antibody provided by the test kits can be monoclonal or polyclonal.

DETAILED DESCRIPTION OF THE INVENTION

Figure 1:
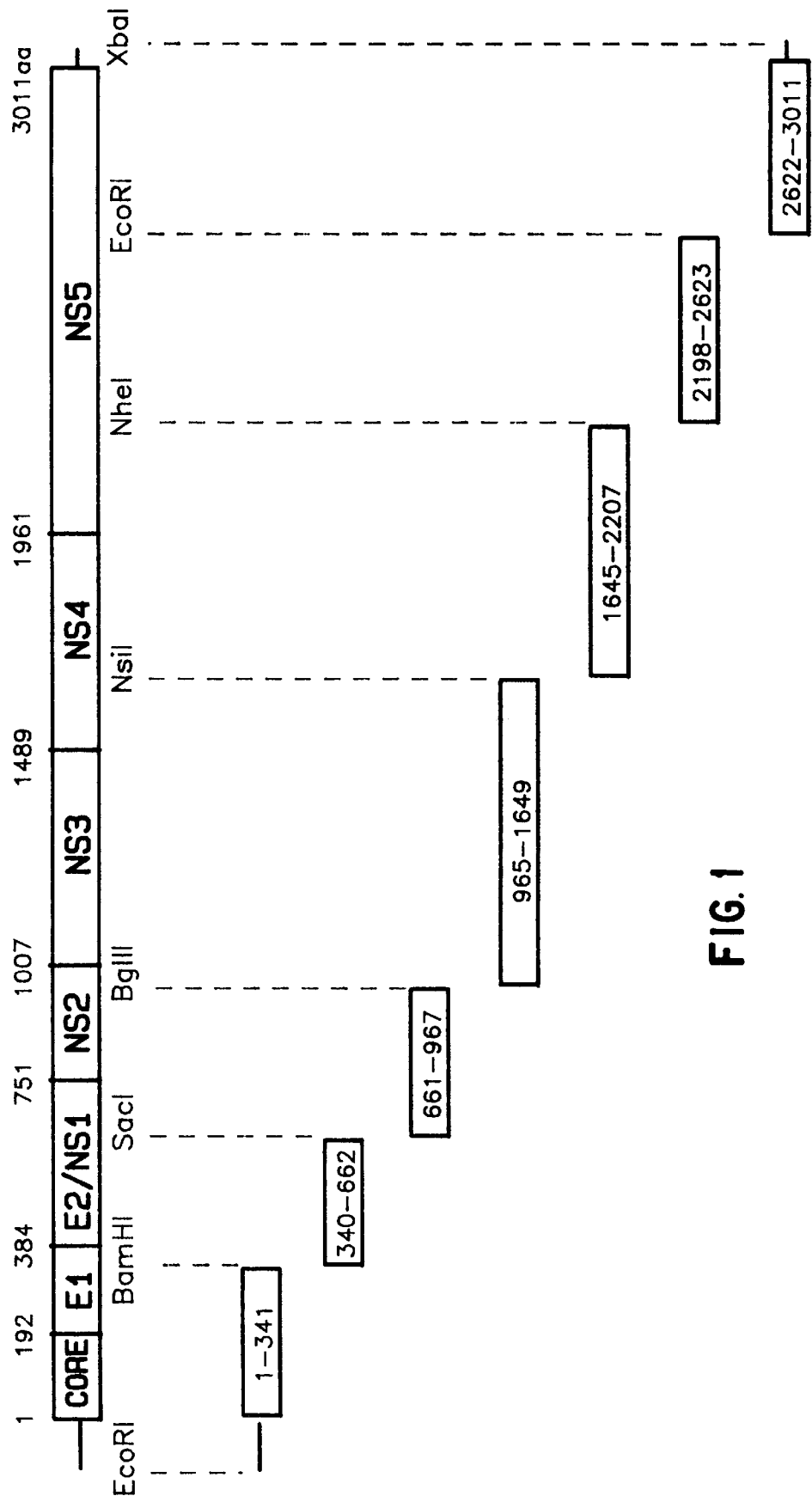
FIG. 1 presents a schematic representation of the strategy employed to generate and assemble HCV genomic clones.

The present invention provides full-length genomic clones useful in a variety of aspects. Such full-length genomic clones can allow culture of the HCV virus which in turn is useful for a variety of purposes. Successful culture of the HCV virus can allow for the development of viral replication inhibitors, viral proteins for diagnostic applications, viral proteins for therapeutics, and specifically structural viral antigens, including, for example, HCV putative envelope, HCV putative E1 and HCV putative E2 fragments.

Cell lines which can be used for viral replication are numerous, and include (but are not limited to), for example, primary hepatocytes, permanent or semi-permanent hepatocytes, cultures transfected with transforming viruses or transforming genes. Especially useful cell lines could include, for example, permanent hepatocyte cultures that continuously express any of several heterologous RNA polymerase genes to amplify HCV RNA sequences under the control of these specific RNA polymerase sequences.

Sources of HCV viral sequences encoding structural antigens include putative core, putative E1 and putative E2 fragments. Expression can be performed in both prokaryotic and eukaryotic systems. The expression of HCV proteins in mammalian expression systems allows for glycosylated proteins such as the E1 and E2 proteins, to be produced. These glycosylated proteins have diagnostic utility in a variety of aspects, including, for example, assay systems for screening and prognostic applications. The mammalian expression of HCV viral proteins allows for inhibitor studies including elucidation of specific viral attachment sites or sequences and/or viral receptors on susceptible cell types, for example, liver cells and the like.

The procurement of specific expression clones developed as described herein in mammalian expression systems provides antigens for diagnostic assays which can determine the stage of HCV infection, such as, for example, acute versus on-going or persistent infections, and/or recent infection versus past exposure. These specific expression clones also provide prognostic markers for resolution of disease such as to distinguish resolution of disease from chronic hepatitis caused by HCV. It is contemplated that earlier seroconversion to glycosylated structural antigens possibly may be detected by using proteins produced in these mammalian expression systems. Antibodies, both monoclonal and polyclonal, also may be produced from the proteins derived from these mammalian expression systems which then in turn may be used for diagnostic; prognostic and therapeutic applications. Also, reagents produced from these novel expression systems described herein may be useful in the characterization and or isolation of other infectious agents.

Proteins produced from these mammalian expression systems, as well as reagents produced from these proteins, can be placed into appropriate container and packaged as test kits for convenience in performing assays. Other aspects of the present invention include a polypeptide comprising an HCV epitope attached to a solid phase and an antibody to an HCV epitope attached to a solid phase. Also included are methods for producing a polypeptide containing an HCV epitope comprising incubating host cells transformed with a mammalian expression vector containing a sequence encoding a polypeptide containing an HCV epitope under conditions which allow expression of the polypeptide, and a polypeptide containing an HCV epitope produced by this method.

The present invention provides assays which utilize the recombinant or synthetic polypeptides provided by the invention, as well as the antibodies described herein in various formats, any of which may employ a signal generating compound in the assay. Assays which do not utilize signal generating compounds to provide a means of detection also are provided. All of the assays described generally detect either antigen or antibody, or both, and include contacting a test sample with at least one reagent provided herein to form at least one antigen/antibody complex and detecting the presence of the complex. These assays are described in detail herein.

Vaccines for treatment of HCV infection comprising an immunogenic peptide obtained from a mammalian expression system containing an HCV epitope, or an inactivated preparation of HCV, or an attenuated preparation of HCV also are included in the present invention. Also included in the present invention is a method for producing antibodies to HCV comprising administering to an individual an isolated immunogenic polypeptide containing an HCV epitope in an amount sufficient to produce an immune response in the inoculated individual.

Also provided by the present invention is a tissue culture grown cell infected with HCV.

The term "antibody containing body component"(or test sample) refers to a component of an individual's body which is the source of the antibodies of interest. These components are well known in the art. These samples include biological samples which can be tested by the methods of the present invention described herein and include human and animal body fluids such as whole blood, serum, plasma, cerebrospinal fluid, urine, lymph fluids, and various external sections of the respiratory, intestinal and genitourinary tracts, tears, saliva, milk, white blood cells, myelomas and the like, biological fluids such as cell culture supernatants, fixed tissue specimens and fixed cell specimens.

After preparing recombinant proteins, as described by the present invention, the recombinant proteins can be used to develop unique assays as described herein to detect either the presence of antigen or antibody to HCV. These compositions also can be used to develop monoclonal and/or polyclonal antibodies with a specific recombinant protein which specifically binds to the immunological epitope of HCV which is desired by the routineer. Also, it is contemplated that at least one recombinant protein of the invention can be used to develop vaccines by following methods known in the art.

It is contemplated that the reagent employed for the assay can be provided in the form of a kit with one or more containers such as vials or bottles, with each container containing a separate reagent such as a monoclonal antibody, or a cocktail of monoclonal antibodies, or a polypeptide (either recombinant or synthetic) employed in the assay.

"Solid phases" ("solid supports") are known to those in the art and include the walls of wells of a reaction tray, test tubes, polystyrene beads, magnetic beads, nitrocellulose strips, membranes, microparticles such as latex particles, and others. The "solid phase" is not critical and can be selected by one skilled in the art. Thus, latex particles, microparticles, magnetic or non-magnetic beads, membranes, plastic tubes, walls of microtiter wells, glass or silicon chips and sheep red blood cells are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include:

natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxies; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable. It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. patent application Ser. No. 07/227,272, now U.S. Pat. No. 5,075,077.

The "indicator reagent" comprises a "signal generating compound" (label) which is capable of generating a measurable signal detectable by external means conjugated (attached) to a specific binding member for HCV. "Specific binding member" as used herein means a member of a specific binding pair. That is, two different molecules where one of the molecules through chemical or physical means specifically binds to the second molecule. In addition to being an antibody member of a specific binding pair for HCV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to HCV as in a sandwich assay, to the capture reagent as in a competitive assay, or to the ancillary specific binding member as in an indirect assay.

The various "signal generating compounds" (labels) contemplated include chromogens, catalysts such as enzymes, luminescent compounds such as fluorescein and rhodamine, chemiluminescent compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

The various "signal generating compounds" (labels) contemplated include chromogens, catalysts such as enzymes, luminescent compounds such as fluorescein and rhodamine, chemiluminescent compounds such as acridinium, phenanthridinium and dioxetane compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

Other embodiments which utilize various other solid phases also are contemplated and are within the scope of this invention. For example, ion capture procedures for immobilizing an immobilizable reaction complex with a negatively charged polymer, described in co-pending U.S. patent application Ser. No. 07/150,278 now abandoned corresponding to EP publication 0326100, and U.S. patent application Ser. No. 07/375,029 now abandoned (EP publication no. 0406473) both of which enjoy common ownership and are incorporated herein by reference, can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in co-pending U.S. patent application Ser. No.06/921,979 now abandoned corresponding to EPO Publication No. 0 273,115, which enjoys common ownership and which is incorporated herein by reference.

Also, the methods of the present invention can be adapted for use in systems which utilize microparticle technology including in automated and semi-automated systems wherein the solid phase comprises a microparticle. Such systems include those described in pending U.S. patent applications Ser. No. 08/425,651 now U.S. Pat. No. 5,244,630 and U.S. Ser. No. 08/425,643 now U.S. Pat. No. 5,089,424, which correspond to published EPO applications Nos. EP 0 425 633 and EP 0 424 634, respectively, which are incorporated herein by reference.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunnelling microscopy eliminates the need for labels which normally must be utilized in many immunoassay systems to detect antigen/antibody complexes. Such a system is described in pending U.S. patent application Ser. No. 07/662,147 now abandoned, which enjoys common ownership and is incorporated herein by reference.

The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis (succinimidyl) suberate, SPPD 9 succinimidyl 3-[2-pyridyldithio] propionate), SMCC (succinimidyl-4-[N-maleimidomethyl] cyclohexane-1-carboxylate), SIAB (succinimidyl [4-iodoacetyl]

aminobenzoate), and SMPB (succinimidyl 4-[1-maleimidophenyl] butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, LOCATION), or Ficoll (molecular weight 70,000 daltons (available from Sigma Chemical Co., St. Louis, Mo.). Also, polyelectrolyte interactions may be used to immobilize a specific binding partner on a surface of a test piece by using techniques and chemistries described by pending U.S. patent applications Ser. No. 07/150,278 now abandoned, filed Jan. 29, 1988, and Ser. No. 07/375,029 now abandoned, filed Jul. 7, 1989, each of which enjoys common ownership and each of which is incorporated herein by reference. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

Various other assay formats may be used, including "sandwich" immunoassays and competitive probe assays. For example, the monoclonal antibodies produced from the proteins of the present invention can be employed in various assay systems to determine the presence, if any, of HCV proteins in a test sample. Fragments of these monoclonal antibodies provided also may be used. For example, in a first assay format, a polyclonal or monoclonal anti-HCV antibody or fragment thereof, or a combination of these antibodies, which has been coated on a solid phase, is contacted with a test sample which may contain HCV proteins, to form a mixture. This mixture is incubated for a time and under conditions sufficient to form antigen/antibody complexes. Then, an indicator reagent comprising a monoclonal or a polyclonal antibody or a fragment thereof, which specifically binds to the HCV fragment, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of HCV antigen present in the test sample and captured on the solid phase, if any, is determined by detecting the measurable signal generated by the signal generating compound. The amount of HCV antigen present in the test sample is proportional to the signal generated.

Alternatively, a polyclonal or monoclonal anti-HCV antibody or fragment thereof, or a combination of these antibodies which is bound to a solid support, the test sample and an indicator reagent comprising a monoclonal or polyclonal antibody or fragments thereof, which specifically binds to HCV antigen, or a combination of these antibodies to which a signal generating compound is attached, are contacted to form a mixture. This mixture is incubated for a time and under conditions sufficient to form antibody/antigen/antibody complexes. The presence, if any, of HCV proteins present in the test sample and captured on the solid phase is determined by detecting the measurable signal generated by the signal generating compound. The amount of HCV proteins present in the test sample is proportional to the signal generated.

In another alternate assay format, one or a combination of one or more monoclonal antibodies of the invention can be employed as a competitive probe for the detection of antibodies to HCV protein. For example, HCV proteins, either alone or in combination, can be coated on a solid phase. A test sample suspected of containing antibody to HCV antigen then is incubated with an indicator reagent comprising a signal generating compound and at least one monoclonal antibody of the invention for a time and under conditions sufficient to form antigen/antibody complexes of either the test sample and indicator reagent to the solid phase or the indicator reagent to the solid phase. The reduction in binding of the monoclonal antibody to the solid phase can be quantitatively measured. A measurable reduction in the signal compared to the signal generated from a confirmed negative NANB hepatitis test sample indicates the presence of anti-HCV antibody in the test sample.

In yet another detection method, each of the monoclonal antibodies of the present invention can be employed in the detection of HCV antigens in fixed tissue sections, as well as fixed cells by immunohistochemical analysis.

In addition, these monoclonal antibodies can be bound to matrices similar to CNBr-activated Sepharose and used for the affinity purification of specific HCV proteins from cell cultures, or biological tissues such as blood and liver.

The monoclonal antibodies of the invention can also be used for the generation of chimeric antibodies for therapeutic use, or other similar applications.

The monoclonal antibodies or fragments thereof can be provided individually to detect HCV antigens. Combinations of the monoclonal antibodies (and fragments thereof) provided herein also may be used together as components in a mixture or "cocktail" of at least one anti-HCV antibody of the invention with antibodies to other HCV regions, each having different binding specificities. Thus, this cocktail can include the monoclonal antibodies of the invention which are directed to HCV proteins and other monoclonal antibodies to other antigenic determinants of the HCV genome.

The polyclonal antibody or fragment thereof which can be used in the assay formats should specifically bind to a specific HCV region or other HCV proteins used in the assay. The polyclonal antibody used preferably is of mammalian origin; human, goat, rabbit or sheep anti-HCV polyclonal antibody can be used. Most preferably, the polyclonal antibody is rabbit polyclonal anti-HCV antibody. The polyclonal antibodies used in the assays can be used either alone or as a cocktail of polyclonal antibodies. Since the cocktails used in the assay formats are comprised of either monoclonal antibodies or polyclonal antibodies having different HCV specificity, they would be useful for diagnosis, evaluation and prognosis of HCV infection, as well as for studying HCV protein differentiation and specificity.

In another assay format, the presence of antibody and/or antigen to HCV can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labelled with a signal generating compound and an indicator reagent comprising a member of a binding pair specific for the second analyte labelled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, proteins derived from human expression systems may be utilized as well as monoclonal antibodies produced from the proteins derived from the mammalian expression systems as disclosed herein. Such assay systems are described in greater detail in pending U.S. patent application Ser. No. 07/574,821 now abandoned entitled Simultaneous Assay for Detecting One Or More Analytes, filed Aug. 29, 1990, which enjoys common ownership and is incorporated herein by reference.

In yet other assay formats, recombinant proteins may be utilized to detect the presence of anti-HCV in test samples. For example, a test sample is incubated with a solid phase to which at least one recombinant protein has been attached. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached and also is contacted with a monoclonal or polyclonal antibody specific for the protein, which preferably has been labelled with an indicator reagent. After incubation for a time and under conditions sufficient for antibody/antigen complexes to form, the solid phase is separated from the free phase, and the label is detected in either the solid or free phase as an indication of the presence of HCV antibody. Other assay formats utilizing the proteins of the present invention are contemplated. These include contacting a test sample with a solid phase to which at least one recombinant protein produced in the mammalian expression system has been attached, incubating the solid phase and test sample for a time and under conditions sufficient to form antigen/antibody complexes, and then contacting the solid phase with a labelled recombinant antigen. Assays such as this and others are described in pending U.S. patent application Ser. No. 07/787,710, now abandoned which enjoys common ownership and is incorporated herein by reference.

While the present invention discloses the preference for the use of solid phases, it is contemplated that the proteins of the present invention can be utilized in non-solid phase assay systems. These assay systems are known to those skilled in the art, and are considered to be within the scope of the present invention.

The present invention will now be described by way of examples, which are meant to illustrate, but not to limit, the spirit and scope of the invention.

EXAMPLES

Example 1

Generation of HCV Genomic Clones

RNA isolated from the serum or plasma of a chimpanzee (designated as "CO") experimentally infected with HCV, or an HCV seropositive human patient (designated as "LG") was transcribed to cDNA using reverse transcriptase employing either random hexamer primers or specific antisense primers derived from the prototype HCV-1 sequence. The sequence has been reported by Choo et al. (Choo et al., Proc. Natl. Acad. Sci. USA 88:2451–2455 [1991], and is available through GenBank data base, Accession No. M62321). This cDNA then was amplified using PCR and AmpliTaq® DNA polymerase (available in the Gene Amp Kit® from Perkin Elmer Cetus, Norwalk, Conn. 06859) employing either a second sense primer located approximately 1000–2000 nucleotides upstream of the specific antisense primer or a pair of sense and antisense primers flanking a 1000–2000 nucleotide fragment of HCV. After 25 to 35 cycles of amplification following standard procedures known in the art, an aliquot of this reaction mixture was subjected to nested PCR (or "PCR-2"), wherein a pair of sense and antisense primers located internal to the original pair of PCR primers was employed to further amplify HCV gene segments in quantities sufficient for analysis and subcloning, utilizing endonuclease recognition sequences present in the second set of PCR primers. In this manner, seven adjacent HCV DNA fragments were generated which then could be assembled using the generic cloning strategy presented and described in FIG. 1. The location of the specific primers used in this manner are presented in Table 1 and are numbered according to the HCV-1 sequence reported by Choo et al (GenBank data base, Accession No. M62321). Prior to assembly, the DNA sequence of each of the individual fragments was determined and translated into the genomic amino acid sequences presented in SEQUENCE ID. NO.1 and 2, respectively, for CO and LG, respectively. Comparison of the genomic polypeptide of CO with that of HCV-1 demonstrated 98 amino acid differences. Comparison of the genomic polypeptide of CO with that of LG. demonstrated 150 amino acid differences. Comparison of the genomic polypeptide of LG with that of HCV-1 demonstrated 134 amino acid differences.

Example 2

Expression of the HCV E2 Protein As A Fusion With The Amyloid Precursor Protein (APP)

Figure 2:
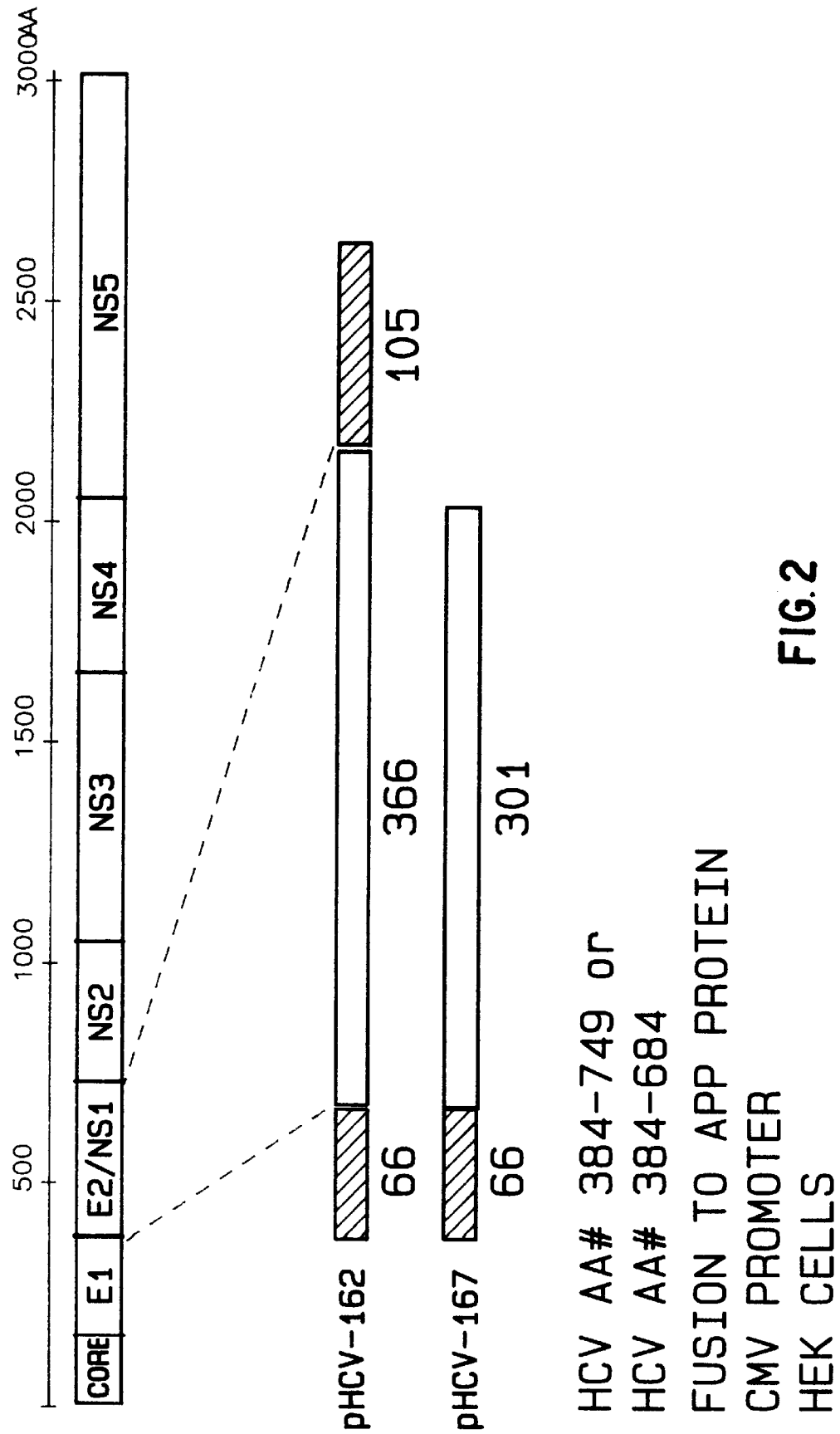
FIG. 2 presents a schematic representation of the location and amino acid composition of the APP-HCV-E2 fusion proteins expressed by the mammalian expression vectors pHCV-162 and pHCV-167.
Figure 3:
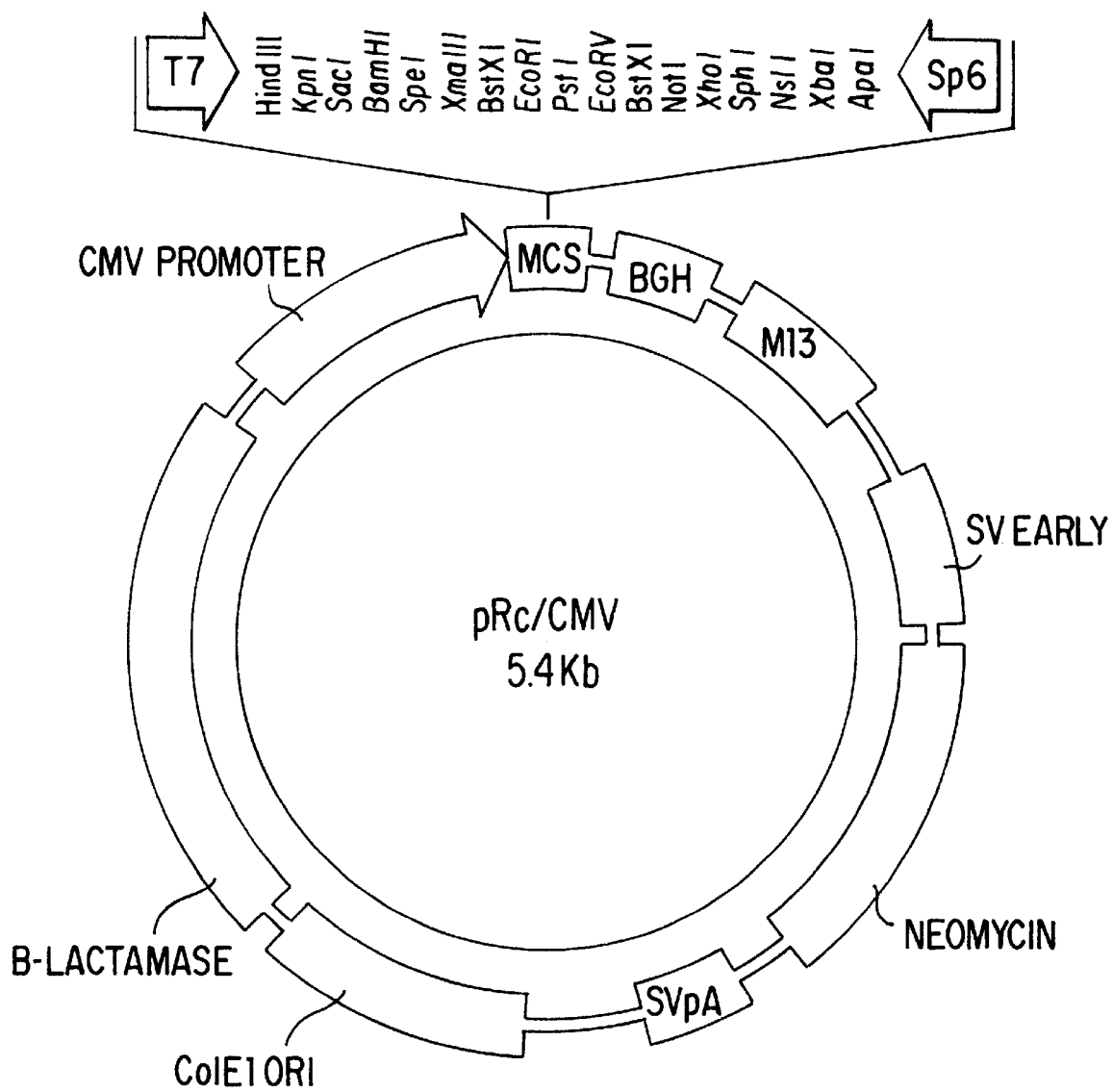
FIG. 3 presents a schematic representation of the mammalian expression vector pRC/CMV.
Figure 4:
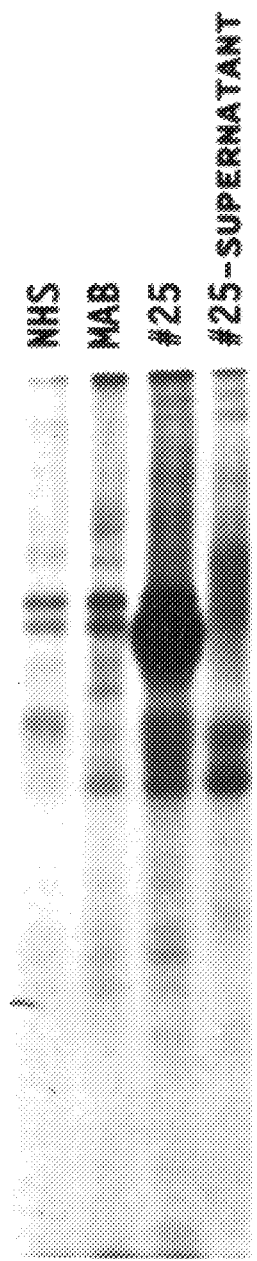
FIG. 4 presents the RIPA results obtained for the APP-HCV-E2 fusion protein expressed by pHCV-162 in HEK-293 cells using HCV antibody positive human sera.
Figure 5:
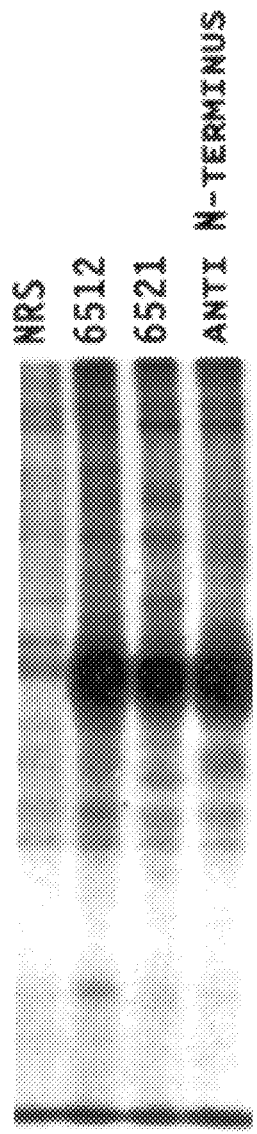
FIG. 5 presents the RIPA results obtained for the APP-HCV-E2 fusion protein expressed by pHCV-162 in HEK-293 cells using rabbit polyclonal sera directed against synthetic peptides.
Figure 6:
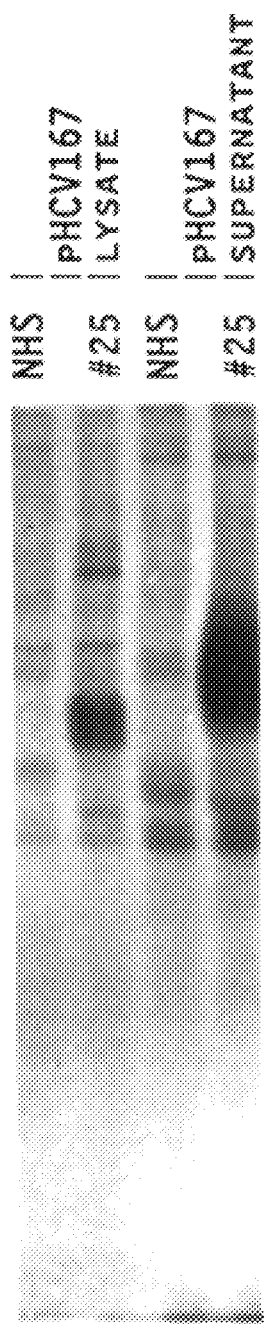
FIG. 6 presents the RIPA results obtained for the APP-HCV-E2 fusion protein expressed by pHCV-167 in HEK-293 cells using HCV antibody positive human sera.
Figure 7:
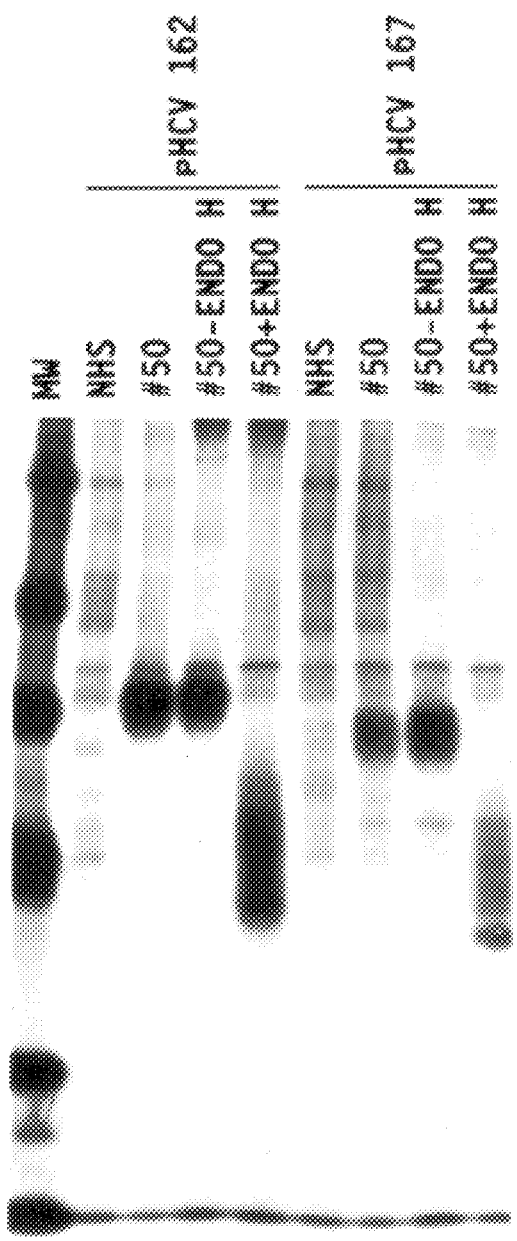
FIG. 7 presents the Endoglycosidase-H digestion of the immunoprecipitated APP-HCV-E2 fusion proteins expressed by pHCV-162 and pHCV-167 in HEK-293 cells.
Figure 8:
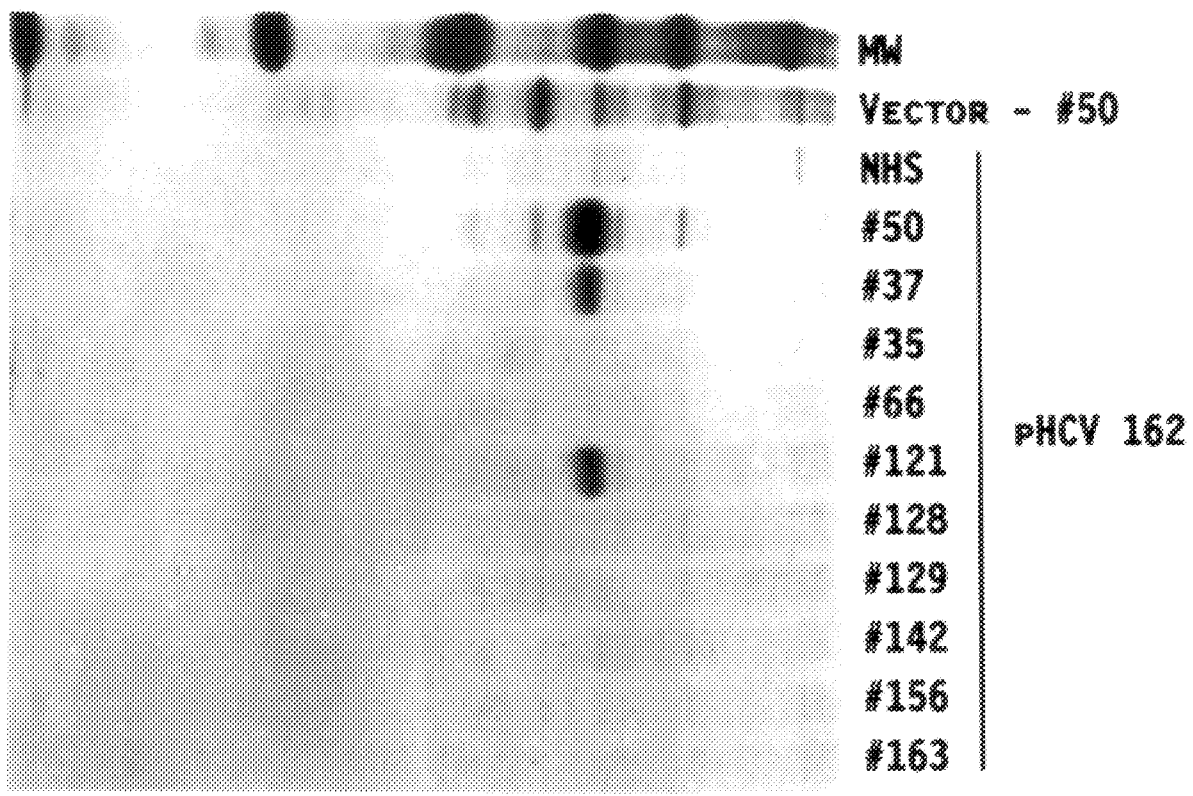
FIG. 8 presents the RIPA results obtained when American HCV antibody positive sera were screened against the APP-HCV-E2 fusion protein expressed by pHCV-162 in HEK-293 cells.
Figure 9:
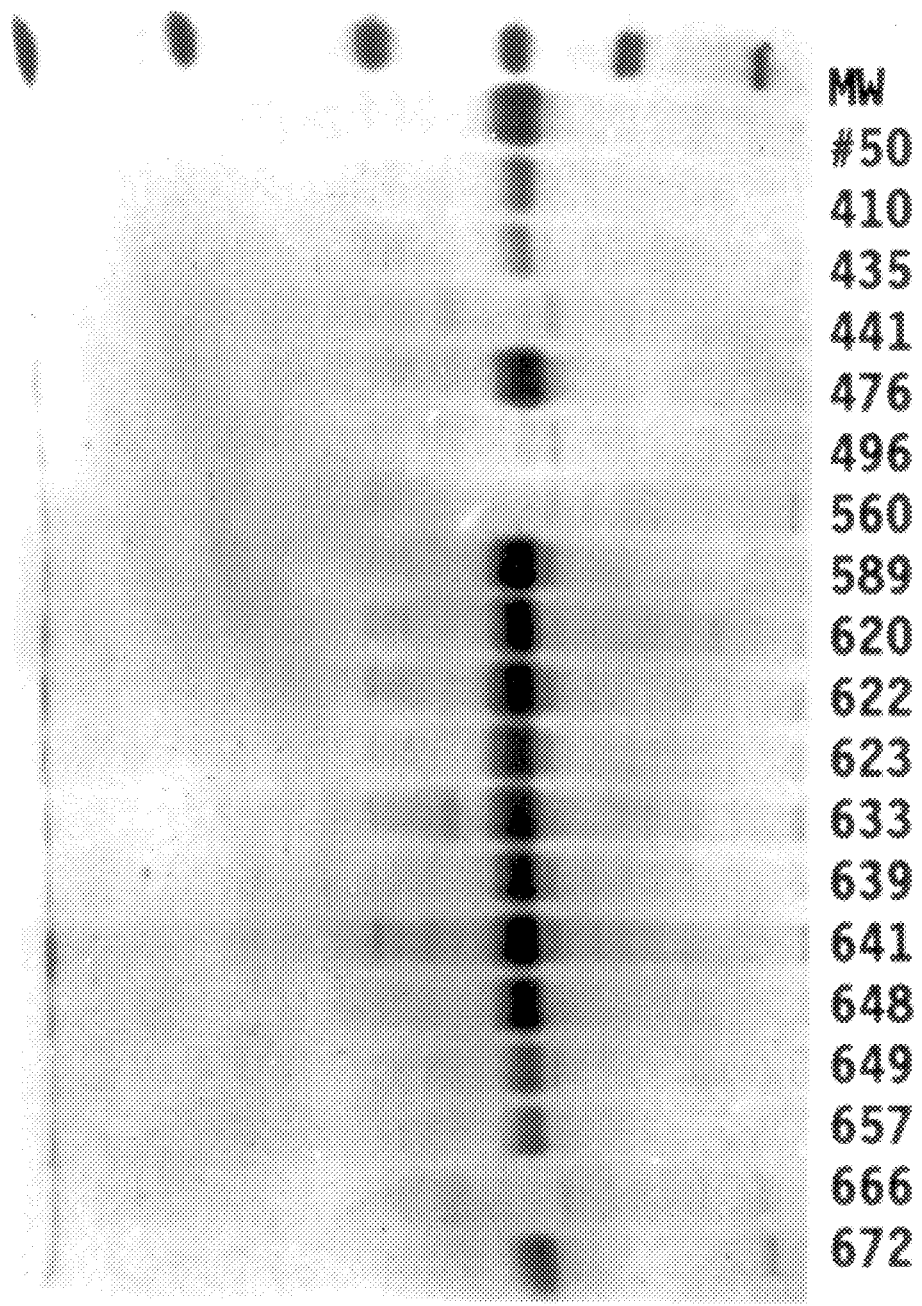
FIG. 9 presents the RIPA results obtained when the sera from Japanese volunteer blood donors were screened against the APP-HCV-E2 fusion protein expressed by pHCV-162 in HEK-293 cells.
Figure 10:
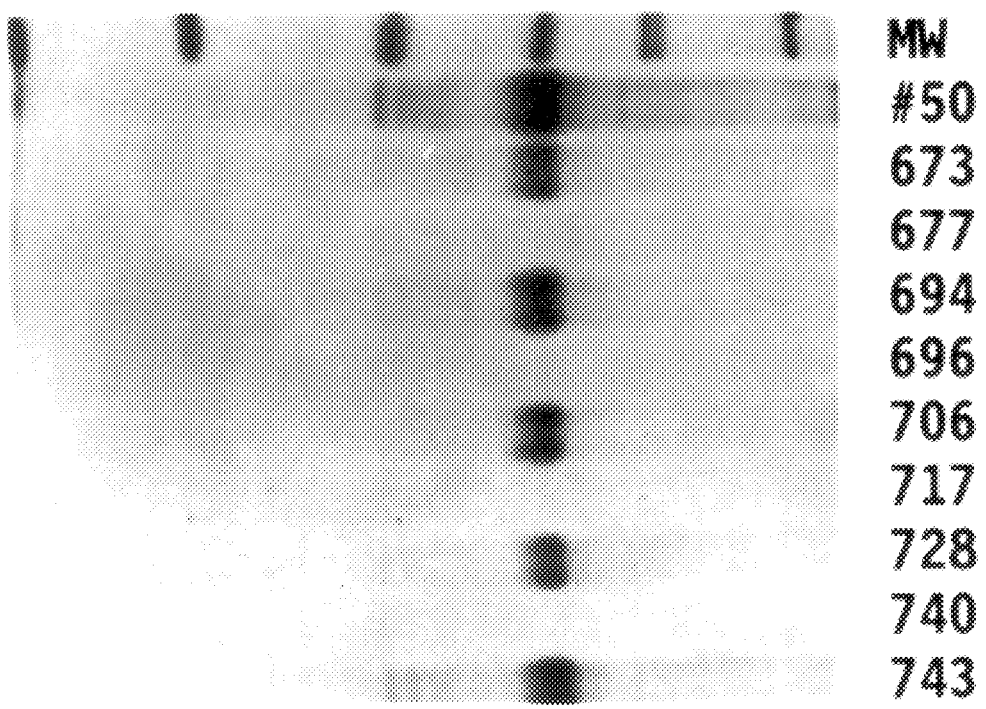
FIG. 10 presents the RIPA results obtained when the sera from Japanese volunteer blood donors were screened against the APP-HCV-E2 fusion protein expressed by pHCV-162 in HEK-293 cells.
Figure 11:
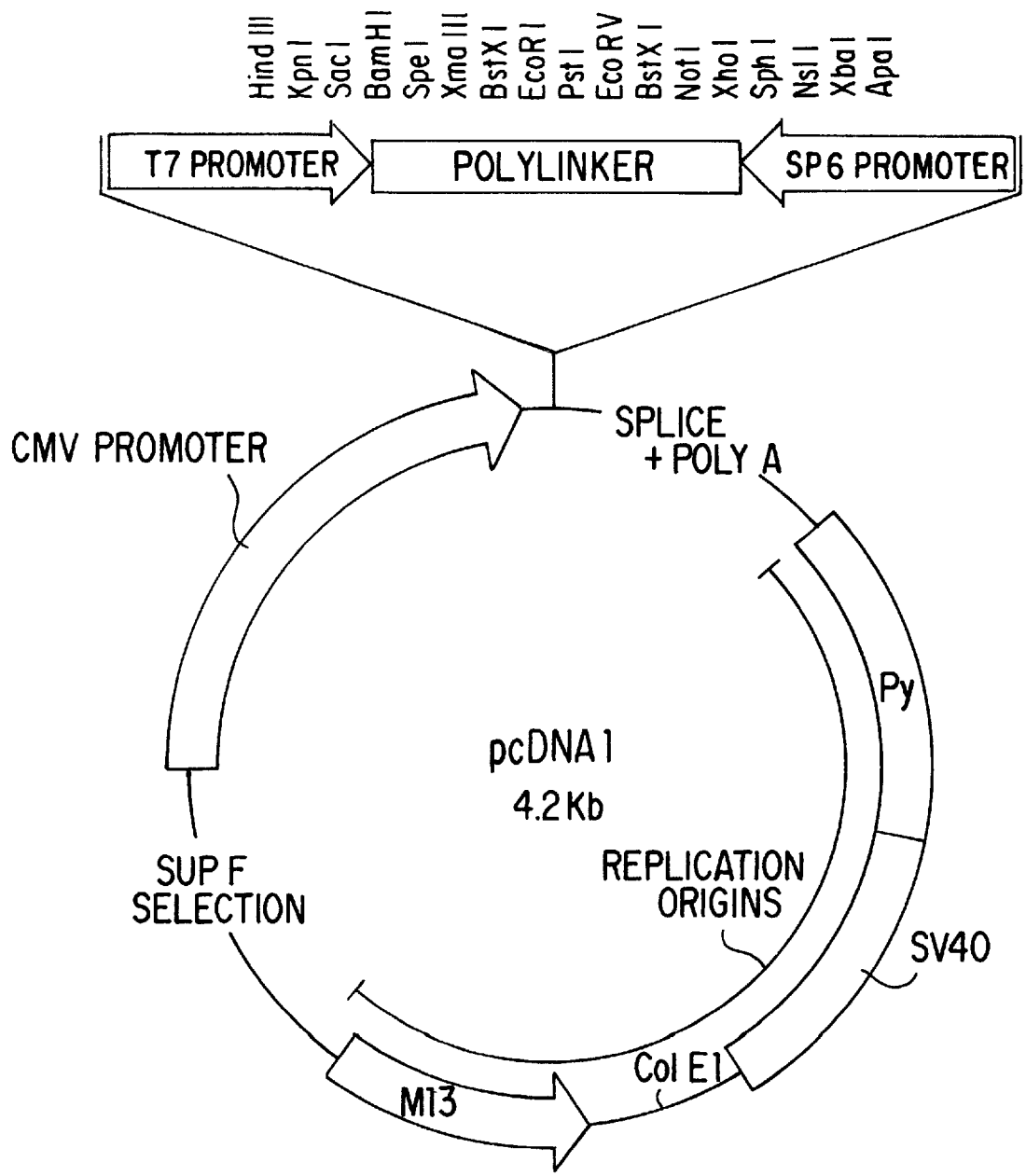
FIG. 11 presents a schematic representation of the mammalian expression vector pCDNA-I.
Figure 12:
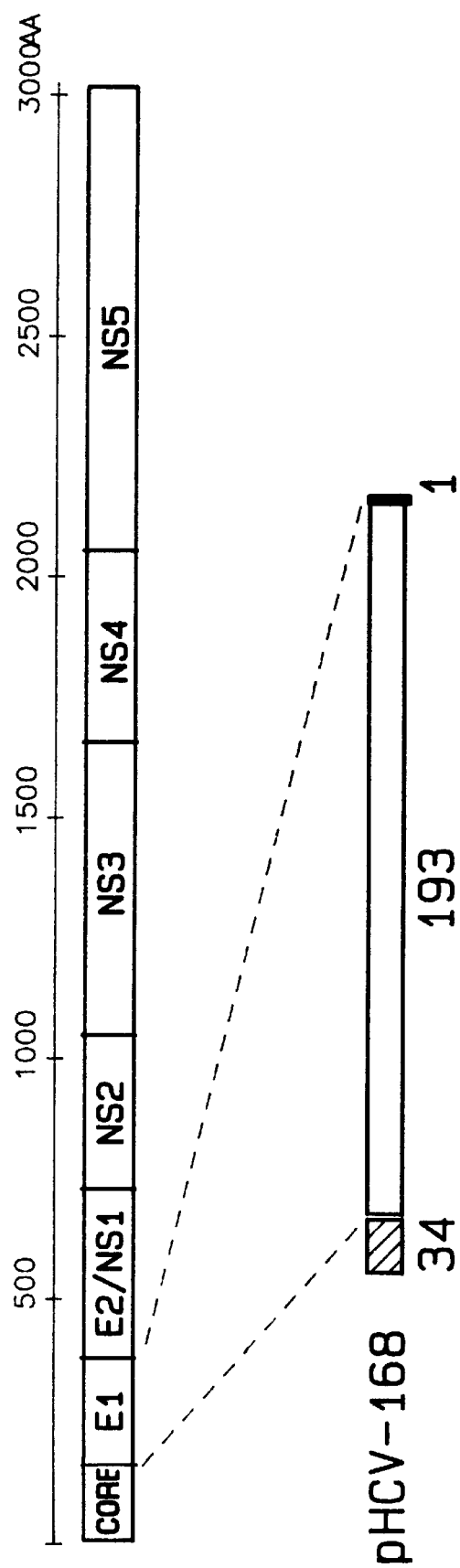
FIG. 12 presents a schematic representation of the location and amino acid composition of the HGH-HCV-E1 fusion protein expressed by the mammalian expression vector pHCV-168.
Figure 13:
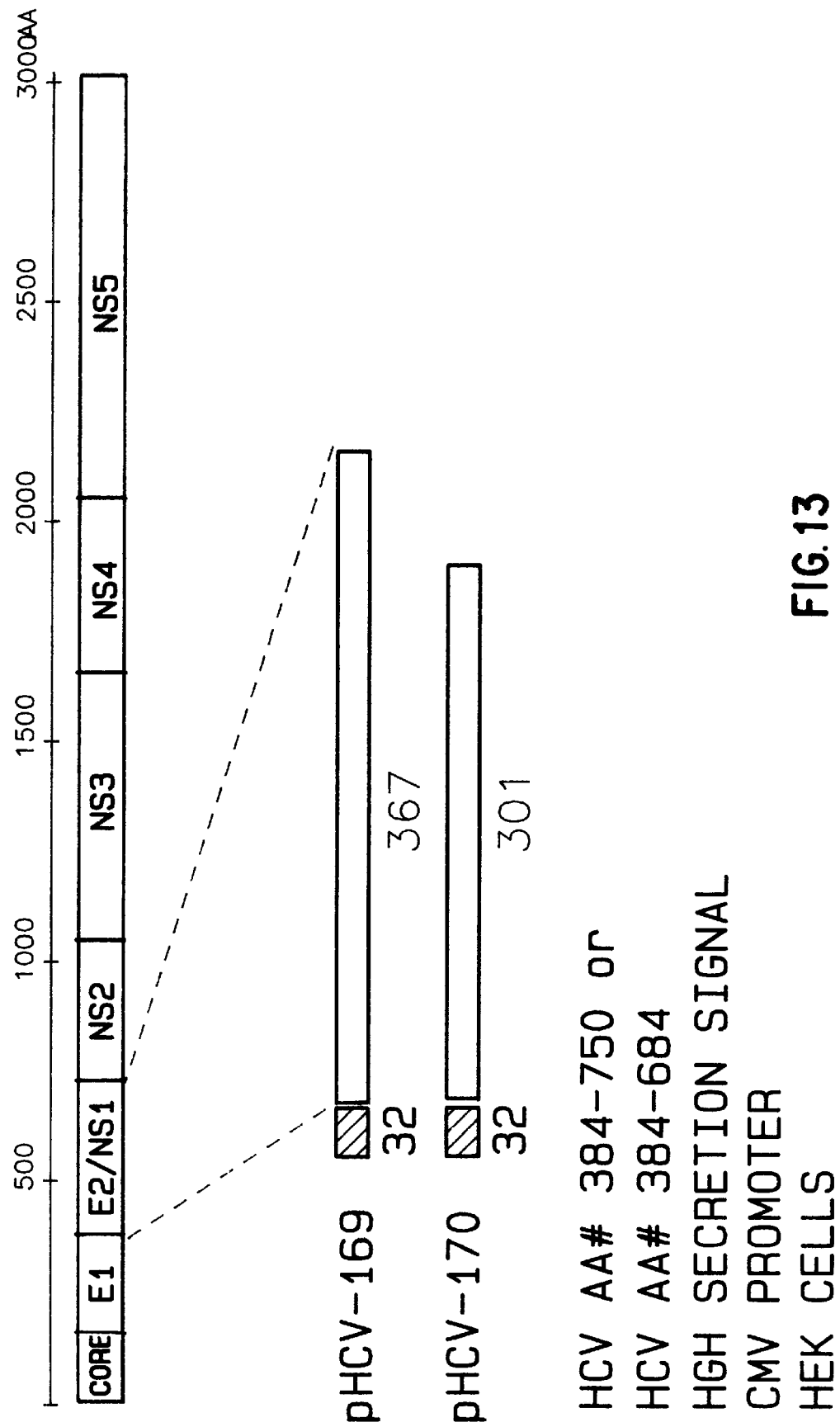
FIG. 13 presents a schematic representation of the location and amino acid composition of the HGH-HCV-E2 fusion proteins expressed by the mammalian expression vectors pHCV-169 and pHCV-170.
Figure 14:
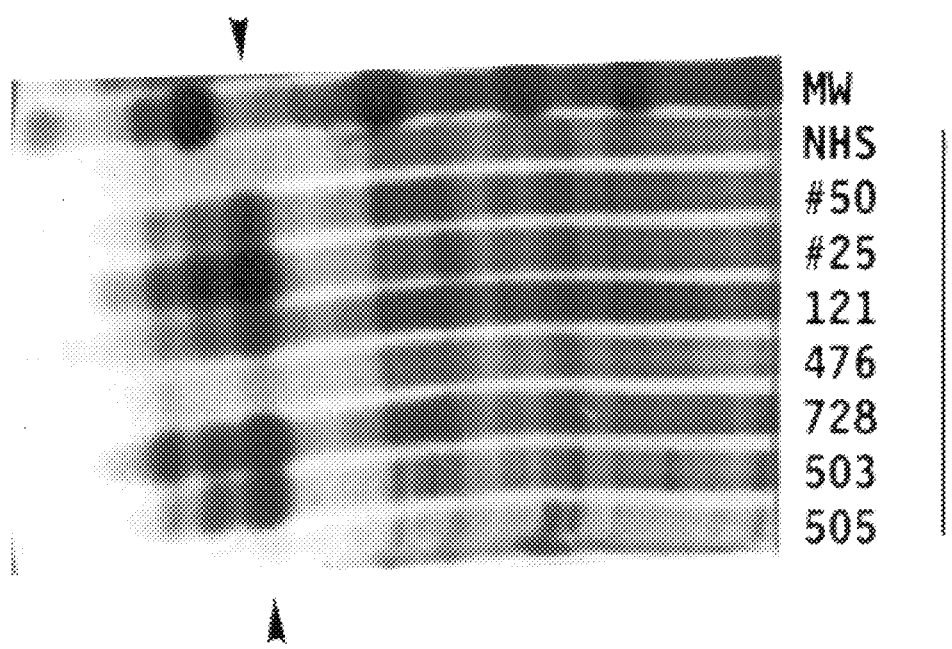
FIG. 14 presents the RIPA results obtained when HCV E2 antibody positive sera were screened against the HGH-HCV-E1 fusion protein expressed by pHCV-168 in HEK-293 cells.

The HCV E2 protein from CO developed as described in Example 1 was expressed as a fusion with the Amyloid Precursor Protein (APP). APP has been described by Kang et al., Nature 325:733–736 (1987). Briefly, HCV amino acids 384–749 of the CO isolate were used to replace the majority of the APP coding sequence as demonstrated in FIG. 2. A HindIII-StyI DNA fragment representing the amino-terminal 66 amino acids and a BglII-XbaI fragment representing the carboxyl-terminal 105 amino acids of APP were ligated to a PCR derived HCV fragment from CO representing HCV amino acids 384–749 containing StyI and BglII restriction sites on its 5' and 3' ends, respectively. This APP-HCV-E2 fusion gene cassette then was cloned into the commercially available mammalian expression vector pRC/CMV shown in FIG. 3, (available from Invitrogen, San Diego, Calif.) at the unique HindIII and XbaI sites. After transformation into E. coli DH5α, a clone designated pHCV-162 was isolated, which placed the expression of the APP-HCV-E2 fusion gene cassette under control of the strong CMV promotor. The complete nucleotide sequence of the mammalian expression vector pHCV-162 is presented in SEQUENCE ID. NO. 3. Translation of nucleotides 922 through 2535 results in the complete amino acid sequence of the APP-HCV-E2 fusion protein expressed by pHCV-162 as presented in SEQUENCE ID. NO. 4.

A primary Human Embryonic Kidney (HEK) cell line transformed with human adenovirus type 5, designated as HEK-293, was used for all transfections and expression analyses. HEK-293 cells were maintained in Minimum Essential Medium (MEM) which was supplemented with 10% fetal calf serum (FCS), penicillin and streptomycin.

Approximately 20 $\mu$g of purified DNA from pHCV-162 was transfected into HEK-293 cells using the modified calcium phosphate protocol as reported by Chen et al., *Molecular and Cellular Biology* 7(8):2745–2752 (1987). The calcium-phosphate-DNA solution was incubated on the HEK-293 cells for about 15 to 24 hours. The solution was removed, the cells were washed twice with MEM media, and then the cells were incubated in MEM media for an additional 24 to 48 hours. In order to analyze protein expression, the transfected cells were metabolically labelled with 100 $\mu$Ci/ml S-35 methionine and cysteine for 12 to 18 hours. The culture media was removed and stored, and the cells were washed in MEM media and then lysed in phosphate buffered saline (PBS) containing 1% Triton X-100® (available from Sigma Chemical Co., St. Louis, Mo.), 0.1% sodium dodecyl sulfate (SDS), and 0.5% deoxychloate, designated as PBS-TDS. This cell lysate then was frozen at −70° C. for 2 to 24 hours, thawed on ice and then clarified by centrifugation at 50,000 ×g force for one hour at 4° C. Standard radio-immunoprecipitation assays (RIPAs) then were conducted on those labelled cell lysates and/or culture medias. Briefly, labelled cell lysates and/or culture medias were incubated with 2 to 5 $\mu$l of specific sera at 4° C. for one hour. Protein-A sepharose then was added and the samples were further incubated for one hour at 4° C. with agitation. The samples were then centrifuged and the pellets washed several times with PBS-TDS buffer. Proteins recovered by immunoprecipitation were eluted by heating in an electrophoresis sample buffer (50 mM Tris-HCl, pH 6.8, 100 mM dithiothreitol [DTT], 2% SDS, 0.1% bromophenol blue, and 10% glycerol) for five minutes at 95° C. The eluted proteins then were separated by SDS polyacrylamide gels which were subsequently treated with a fluorographic reagent such as Enlightening® (available from NEN [DuPont], Boston, Mass.), dried under vacuum and exposed to x-ray film at −70° C. with intensifying screens. FIG. 4 presents a RIPA analysis of pHCV-162 transfected HEK cell lysate precipitated with normal human sera (NHS), a monoclonal antibody directed against APP sequences which were replaced in this construct (MAB), and an HCV antibody positive human sera (#25). Also presented in FIG. 4 is the culture media (supernatant) precipitated with the same HCV antibody positive human sera (#25). From FIG. 4, it can be discerned that while only low levels of an HCV specific protein of approximately 75K daltons is detected in the culture media of HEK-293 cells transfected with pHCV-162, high levels of intracellular protein expression of the APP-HCV-E2 fusion protein of approximately 70K daltons is evident.

In order to further characterize this APP-HCV-E2 fusion protein, rabbit polyclonal antibody raised against synthetic peptides were used in a similar RIPA, the results of which are illustrated in FIG. 5. As can be discerned from this Figure, normal rabbit serum (NRS) does not precipitate the 70K dalton protein while rabbit sera raised against HCV amino acids 509–551 (6512), HCV amino acids 380–436 (6521), and APP amino acids 45–62 (anti- N-terminus) are highly specific for the 70K dalton APP-HCV-E2 fusion protein.

In order to enhance secretion of this APP-HCV-E2 fusion protein, another clone was generated which fused only the amino-terminal 66 amino acids of APP, which contain the putative secretion signal sequences to the HCV-E2 sequences. In addition, a strongly hydrophobic sequence at the carboxyl-terminal end of the HCV-E2 sequence which was identified as a potential transmembrane spanning region was deleted. The resulting clone was designated as pHCV-167 and is schematically illustrated in FIG. 2. The complete nucleotide sequence of the mammalian expression vector pHCV-167 is presented in SEQUENCE ID. NO. 5 Translation of nucleotides 922 through 2025 results in the complete amino acid sequence of the APP-HCV-E2 fusion protein expressed by pHCV-167 as presented in SEQUENCE ID. NO. 6. Purified DNA of pHCV-167 was transfected into HEK-293 cells and analyzed by RIPA and polyacrylamide SDS gels as described previously herein. FIG. 6 presents the results in which a normal human serum sample (NHS) failed to recognize the APP-HCV-E2 fusion protein present in either the cell lysate or the cell supernatant of HEK-293 cells transfected with pHCV-167. The positive control HCV serum sample (#25), however, precipitated an approximately 65K dalton APP-HCV-E2 fusion protein present in the cell lysate of HEK-293 cells transfected with pHCV-167. In addition, substantial quantities of secreted APP-HCV-E2 protein of approximately 70K daltons was precipitated from the culture media by serum #25.

Digestion with Endoglycosidase-H (Endo-H) was conducted to ascertain the extent and composition of N-linked glycosylation in the APP-HCV E2 fusion proteins expressed by pHCV-167and pHCV-162 in HEK-293 cells. Briefly, multiple aliquots of labelled cell lysates from pHCV-162 and pHCV-167 transfected HEK-293 cells were precipitated with human serum #50 which contained antibody to HCV E2 as previously described. The Protein-A sepharose pellet containing the immunoprecipitated protein-antibody complex was then resuspended in buffer (75 mM sodium acetate, 0.05% SDS) containing or not containing 0.05 units per ml of Endo-H (Sigma). Digestions were performed at 37° C. for 12 to 18 hours and all samples were analyzed by polyacrylamide SDS gels as previously described. FIG. 7 presents the results of Endo-H digestion. Carbon-14 labelled molecular weight standards (MW) (obtained from Amersham, Arlington Heights, Ill.) are common on all gels and represent 200K, 92.5K, 69K, 46K, 30K and 14.3K daltons, respectively. Normal human serum (NHS) does not immunoprecipitate the APP-HCV-E2 fusion protein expressed by either pHCV-162 or pHCV-167, while human serum positive for HCV E2 antibody (#50) readily detects the 72K dalton APP-HCV-E2 fusion protein in pHCV-162 and the 65K dalton APP-HCV E2 fusion protein in pHCV-167. Incubation of these immunoprecipitated proteins in the absence of Endo-H (#50 −Endo-H) does not significantly affect the quantity or mobility of either pHCV-162 or pHCV-167 expressed proteins. Incubation in the presence of Endo-H (#50 +Endo-H), however, drastically reduces the mobility of the proteins expressed by pHCV-162 and pHCV-167, producing a heterogenous size distribution. The predicted molecular weight of the non-glycosylated polypeptide backbone of pHCV-162 is approximately 59K daltons. Endo-H treatment of pHCV-162 lowers the mobility to a minimum of approximately 44K daltons, indicating that the APP-HCV-E2 fusion protein produced by pHCV-162 is proteolytically cleaved at the carboxyl-terminal end. A size of approximately 44K daltons is consistent with cleavage at or near HCV amino acid 720. Similarly, Endo-H treatment of pHCV-167 lowers the mobility to a minimum of approximately 41K daltons, which compares favorably with the predicted molecular weight of approximately 40K daltons for the intact APP-HCV-E2 fusion protein expressed by pHCV-167.

Example 3
Detection of HCV E2 Antibodies

Figure 15:
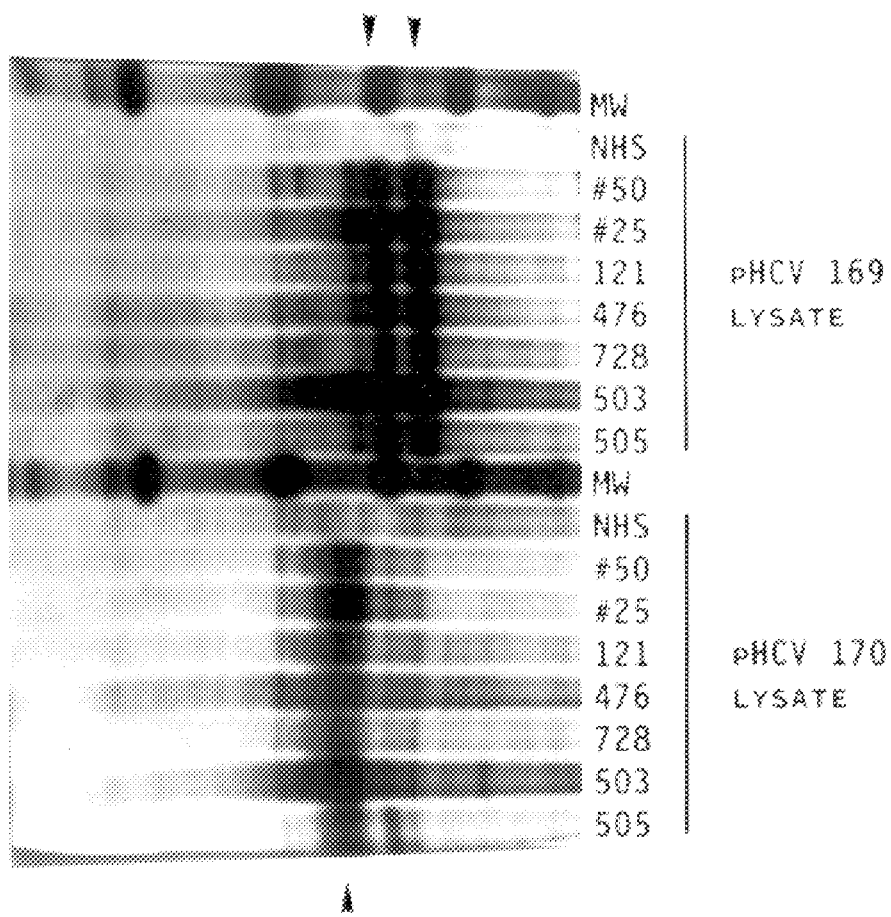
FIG. 15 presents the RIPA results obtained when HCV E2 antibody positive sera were screened against the HGH-HCV-E2 fusion proteins expressed by pHCV-169 and pHCV-170 in HEK-293 cells.

Radio-immunoprecipitation assay (RIPA) and polyacrylamide SDS gel analysis previously described was used to screen numerous serum samples for the presence of antibody directed against HCV E2 epitopes. HEK-293 cells transfected with pHCV-162 were metabolically labelled and cell lysates prepared as previously described. In addition to RIPA analysis, all serum samples were screened for the presence of antibodies directed against specific HCV recombinant antigens representing distinct areas of the HCV genome using the Abbott Matrix® System. (available from Abbott Laboratories, Abbott Park, Ill. 60064, U.S. Pat. No. 5,075, 077). In the Matrix data presented in Tables 2 through 7, C100 yeast represents the NS4 region containing HCV amino acids 1569–1930, C100 *E. coli* represents HCV amino acids 1676–1930, NS3 represents HCV amino acids 1192–1457, and CORE represents HCV amino acids 1–150.

FIG. 8 presents a representative RIPA result obtained using pHCV-162 cell lysate to screen HCV antibody positive American blood donors and transfusion recipients. Table 2 summarizes the antibody profile of these various American blood samples, with seven of seventeen (41%) samples demonstrating HCV E2 antibody. Genomic variability in the E2 region has been demonstrated between different HCV isolates, particularly in geographically distinct isolates which may lead to differences in antibody responses. We therefore screened twenty-six Japanese volunteer blood donors and twenty Spanish hemodialysis patients previously shown to contain HCV antibody for the presence of specific antibody to the APP-HCV E2 fusion protein expressed by pHCV-162. FIGS. 9 and 10 present the RIPA analysis on twenty-six Japanese volunteer blood donors. Positive control human sera (#50) and molecular weight standards (MW) appear in both figures in which the specific immunoprecipitation of the approximately 72K dalton APP-HCV-E2 fusion protein is demonstrated for several of the serum samples tested. Table 3 presents both the APP-HCV-E2 RIPA and Abbott Matrix® results summarizing the antibody profiles of each of the twenty-six Japanese samples tested. Table 4 presents similar data for the twenty Spanish hemodialysis patients tested. Table 5 summarizes the RIPA results obtained using pHCV-162 to detect HCV E2 specific antibody in these various samples. Eighteen of twenty-six (69%) Japanese volunteers blood donors, fourteen of twenty (70%) Spanish hemodialysis patients, and seven of seventeen (41%) American blood donors or transfusion recipients demonstrated a specific antibody response against the HCV E2 fusion protein. The broad immunoreactivity demonstrated by the APP-HCV-E2 fusion protein expressed by pHCV-162 suggests the recognition of conserved epitopes within HCV E2.

Serial bleeds from five transfusion recipients which seroconverted to HCV antibody were also screened using the APP-HCV-E2 fusion protein expressed by pHCV-162. This analysis was conducted to ascertain the time interval after exposure to HCV at which E2 specific antibodies can be detected. Table 6 presents one such patient (AN) who seroconverted to NS3 at 154 days post transfusion (DPT). Antibodies to HCV E2 were not detected by RIPA until 271 DPT. Table 7 presents another such patient (WA), who seroconverted to CORE somewhere before 76 DPT and was positive for HCV E2 antibodies on the next available bleed date (103 DPT). Table 8 summarizes the serological results obtained from these five transfusion recipients indicating (a) some general antibody profile at seroconversion (AB Status); (b) the days post transfusion at which an ELISA test would most likely detect HCV antibody (2.0 GEN); (c) the samples in which HCV E2 antibody was detected by RIPA (E2 AB Status); and (d) the time interval covered by the bleed dates tested (Samples Tested). The results indicate that antibody to HCV E2, as detected in the RIPA procedure described here, appears after seroconversion to at least one other HCV marker (CORE, NS3, C100, etc.) and is persistent in nature once it appears. In addition, the absence of antibody to the structural gene CORE appears highly correlated with the absence of detectable antibody to E2, another putative structural antigen. Further work is ongoing to correlate the presence or absence of HCV gene specific antibodies with progression of disease and/or time interval since exposure to HCV viral antigens.

Example 4

Expression of HCV E1and E2 Using Human Growth Hormone Secretion Signal

HCV DNA fragments representing HCV E1 (HCV amino acids 192 to 384) and HCV E2 (HCV amino acids 384–750 and 384–684) were generated from the CO isolate using PCR as described in Example 2. An Eco RI restriction site was used to attach a synthetic oligonucleotide encoding the Human Growth Hormone (HGH) secretion signal (Blak et al, *Oncogene*, 3 129–136, 1988) at the 5' end of these HCV sequence. The resulting fragment was then cloned into the commercially available mammalian expression vector pCDNA-I, (available from Invitrogen, San Diego, Calif.) illustrated in FIG. 11. Upon transformation into *E. coli* MC1061/P3, the resulting clones place the expression of the cloned sequence under control of the strong CMV promoter. Following the above outlined methods, a clone capable of expressing HCV-E1 (HCV amino acids 192–384) employing the HGH secretion signal at the extreme amino-terminal end was isolated. The clone was designated pHCV-168 and is schematically illustrated in FIG. 12. Similarly, clones capable of expressing HCV E2 (HCV amino acids 384–750 or 384–684) employing the HGH secretion signal were isolated, designated pHCV-169 and pHVC-170 respectively and illustrated in FIG. 13. The complete nucleotide sequence of the mammalian expression. vectors pHCV-168, pHCV-169, and pHCV-170 are presented in Sequence ID. NO. 7, 9, and 11 respectively. Translation of nucleotides 2227 through 2913 results in the complete amino acid sequence of the HGH-HCV-E1 fusion protein expressed by pHCV-168 as presented in Sequence ID. NO. 8. Translation of nucleotides 2227 through 3426 results in the complete amino acid sequence of the HGH-HCV-E2 fusion protein expressed by pHCV-169 as presented in Sequence ID. NO. 10. Translation of nucleotides 2227 through 3228 results in the complete amino acid sequence of the HGH-HCV-E2 fusion protein expressed by pHCV-170 as presented in Sequence ID. NO. 12. Purified DNA from pHCV-168, pHCV-169, and pHCV-170 was transfected into HEK-293 cells which were then metabolically labelled, cell lysates prepared, and RIPA analysis performed as described previously herein. Seven sera samples previously shown to contain antibodies to the APP-HCV-E2 fusion protein expressed by pHCV-162 were screened against the labelled cell lysates of pHCV-168, pHCV-169, and pHCV-170. FIG. 14 presents the RIPA analysis for pHCV-168 and demonstrated that five sera containing HCV E2 antibodies also contain HCV E1 antibodies directed against as approximately 33K dalton HGH-HCV-E1 fusion protein (#25, #50, 121, 503, and 728), while two other sera do not contain those antibodies (476 and 505). FIG. 15 presents the RIPA results obtained when the same sera indicated above were screened against the labelled cell lysates of either pHCV-169 or pHCV-170. All seven HCV E1 antibody positive sera detected two protein species of approximately 70K and 75K daltons in cells transfected with pHCV-168. These two different HGH-HCV-E2 protein species could result from incomplete proteolytic cleavage of the HCV E2 sequence at the carboxyl-terminal end (at or near HCV amino acid 720) or from differences in carbohydrate processing between the two species. All seven HCV E2 antibody positive sera detected a single protein species of approximately 62K daltons for the HGH-HCV-E2 fusion protein expressed by pHCV-170. Table 9 summarizes the serological profile of six of the seven HCV E2 antibody positive sera screened against the HGH-HCV-E1 fusion protein expressed by pHCV-170. Further work is ongoing to correlate the presence or absence of HCV gene specific antibodies with progression of disease and/or time interval since exposure to HCV viral antigens.

Clones pHCV-167 and pHCV-162 have been deposited at the American Type Culture Collection, 10801 University Boulevard, Manassas, Va. 20110, as of Jan. 17, 1992 under the terms of the Budapest Treaty, and accorded the following ATCC Designation Numbers: Clone pHCV-167 was accorded ATCC deposit number 68893 and clone pHCV-162 was accorded ATCC deposit number 68894. Clones PHCV-168, pHCV-169 and pHCV-170 have been deposited at the American Type Culture Collection, 10801 University Boulevard Manassas, Va. 20110, as of Jan. 26, 1993 under the terms of the Budapest Treaty, and accorded the following ATCC Designation Numbers: Clone pHCV-168 was accorded ATCC deposit number 69228, clone pHCV-169 was accorded ATCC deposit number 69229 and clone pHCV-170 was accorded ATCC deposit number 69230. The designated deposits will be maintained for a period of thirty (30) years from the date of deposit, or for five (5) years after the last request for the deposit; or for the enforceable life of the U.S. patent, whichever is longer. These deposits and other deposited materials mentioned herein are intended for convenience only, and are not required to practice the invention in view of the descriptions herein. The HCV cDNA sequences in all of the deposited materials are incorporated herein by reference.

Other variations of applications of the use of the proteins and mammalian expression systems provided herein will be apparent to those skilled in the art. Accordingly, the invention is intended to be limited only in accordance with the appended claims.

TABLE 1

| FRAG- | PCR-1 PRIMERS | | PCR-2 PRIMERS | |
|---|---|---|---|---|
| MENT | SENSE | ANTISENSE | SENSE | ANTISENSE |
| 1 | 1–17 | 1376–1400 | 14–31 | 1344–1364 |
| 2 | 1320–1344 | 2332–2357 | 1357–1377 | 2309–2327 |
| 3 | 2288–2312 | 3245–3269 | 2322–2337 | 3224–3242 |
| 4 | 3178–3195 | 5303–5321 | 3232–3252 | 5266–5289 |
| 5 | 5229–5249 | 6977–6996 | 5273–5292 | 6940–6962 |
| 6 | 6907–6925 | 8221–8240 | 6934–6954 | 8193–8216 |
| 7 | 8175–8194 | 9385–9401 | 8199–8225 | 9363–9387 |

TABLE 2

AMERICAN HCV POSITIVE SERA

| SAMPLE | C100 YEAST S/CO | C100 E. COLI S/CO | NS3 S/CO | CORE S/CO | E2 RIPA |
|---|---|---|---|---|---|
| 22 | 0.31 | 1.09 | 1.72 | 284.36 | + |
| 32 | 0.02 | 0.10 | 7.95 | 331.67 | − |
| 35 | 0.43 | 0.68 | 54.61 | 2.81 | − |
| 37 | 136.24 | 144.29 | 104.13 | 245.38 | + |
| 50 | 101.04 | 133.69 | 163.65 | 263.72 | + |
| 108 | 39.07 | 34.55 | 108.79 | 260.47 | − |
| 121 | 1.28 | 4.77 | 172.65 | 291.82 | + |
| 128 | 0.06 | 0.06 | 0.87 | 298.49 | − |
| 129 | 0.00 | 0.02 | 107.11 | 0.00 | − |
| 142 | 8.45 | 8.88 | 73.93 | 2.32 | − |
| 156 | 0.45 | 0.14 | 0.67 | 161.84 | − |
| 163 | 1.99 | 3.26 | 11.32 | 24.36 | − |
| MI | 89.9 | 118.1 | 242.6 | 120.4 | − |
| KE | 167.2 | 250.9 | 0.8 | 0.3 | − |
| WA | 164.4 | 203.3 | 223.9 | 160.9 | + |
| PA | 50.6 | 78.8 | 103.8 | 78.0 | + |
| AN | 224.8 | 287.8 | 509.9 | 198.8 | + |

TABLE 3

JAPANESE HCV POSITIVE POSITIVE BLOOD DONORS

| SAMPLE | C100 YEAST S/CO | C100 E. COLI S/CO | NS3 S/CO | CORE S/CO | E2 RIPA |
|---|---|---|---|---|---|
| 410 | 86.33 | 93.59 | 9.68 | 257.82 | + |
| 435 | 0.18 | 0.18 | 0.69 | 39.25 | + |
| 441 | 0.20 | 0.09 | 0.17 | 6.51 | − |
| 476 | 0.37 | 1.29 | 144.66 | 302.35 | + |
| 496 | 39.06 | 37.95 | 2.78 | 319.99 | − |
| 560 | 1.08 | 0.68 | 3.28 | 26.59 | − |
| 589 | 0.06 | 1.28 | 117.82 | 224.23 | + |
| 620 | 0.17 | 1.37 | 163.41 | 256.64 | + |
| 622 | 123.46 | 162.54 | 154.67 | 243.44 | + |
| 623 | 23.46 | 26.55 | 143.72 | 277.24 | + |
| 633 | 0.01 | 0.43 | 161.84 | 264.02 | + |
| 639 | 1.40 | 2.23 | 12.15 | 289.80 | + |
| 641 | 0.01 | 0.08 | 8.65 | 275.00 | + |
| 648 | −0.00 | 0.03 | 0.79 | 282.64 | + |
| 649 | 97.00 | 127.36 | 147.46 | 194.73 | + |
| 657 | 4.12 | 6.33 | 141.04 | 256.57 | + |
| 666 | 0.14 | 0.24 | 5.90 | 60.82 | − |
| 673 | 72.64 | 90.11 | 45.31 | 317.66 | + |
| 677 | 0.05 | 0.23 | 2.55 | 99.67 | − |
| 694 | 86.72 | 87.18 | 45.43 | 248.80 | + |
| 696 | 0.02 | −0.02 | 0.26 | 12.55 | − |
| 706 | 17.02 | 12.96 | 153.77 | 266.87 | + |
| 717 | 0.04 | 0.02 | 0.15 | 10.46 | − |
| 728 | −0.01 | 0.26 | 90.37 | 246.30 | + |
| 740 | 0.02 | 0.10 | 0.25 | 46.27 | − |
| 743 | 1.95 | 1.56 | 133.23 | 254.25 | + |

TABLE 4

SPANISH HEMODIALYSIS PATIENTS

| SAMPLE | C100 YEAST S/CO | C100 E. COLI S/CO | NS3 S/CO | CORE S/CO | E2 RIPA |
|---|---|---|---|---|---|
| 1 | 0.0 | 0.3 | 188.6 | −0.0 | − |
| 2 | 129.3 | 142.8 | 165.4 | 201.0 | + |
| 3 | 113.7 | 128.5 | 154.5 | 283.3 | + |
| 5 | 130.6 | 143.8 | 133.4 | 186.1 | + |
| 6 | 56.2 | 63.4 | 93.6 | 32.0 | + |
| 7 | 0.0 | 0.2 | 72.1 | 211.5 | + |
| 8 | 156.7 | 171.9 | 155.1 | 227.0 | + |

TABLE 4-continued

SPANISH HEMODIALYSIS PATIENTS

| SAMPLE | C100 YEAST S/CO | C100 E. COLI S/CO | NS3 S/CO | CORE S/CO | E2 RIPA |
|---|---|---|---|---|---|
| 9 | 65.3 | 78.9 | 76.1 | 102.6 | + |
| 10 | 136.7 | 149.3 | 129.4 | 190.2 | + |
| 11 | 0.0 | 0.7 | 155.7 | 272.4 | + |
| 12 | 1.0 | 1.9 | 143.6 | 210.6 | + |
| 13 | 0.0 | 0.3 | 111.2 | 91.1 | − |
| 14 | 1.1 | 3.1 | 94.7 | 214.8 | − |
| 15 | 45.9 | 66.1 | 106.3 | 168.2 | + |
| 16 | 36.3 | 68.8 | 149.3 | 0.1 | − |
| 17 | 121.0 | 129.9 | 113.4 | 227.8 | + |
| 18 | 64.8 | 99.7 | 138.9 | 0.2 | − |
| 19 | 25.6 | 34.1 | 157.4 | 254.9 | + |
| 20 | 104.9 | 125.1 | 126.8 | 218.3 | + |
| 21 | 48.1 | 68.5 | 0.8 | 49.4 | − |

TABLE 5

ANTIBODY RESPONSE TO HCV PROTEINS

| | C100 YEAST S/CO | C100 E. COLI S/CO | NS3 S/CO | CORE S/CO | E2 RIPA |
|---|---|---|---|---|---|
| AMERICAN BLOOD DONORS | 11/17 | 12/17 | 14/17 | 15/17 | 7/17 |
| SPANISH HEMODIALYSIS PATIENTS | 16/20 | 16/20 | 19/20 | 17/20 | 14/20 |
| JAPANESE BLOOD DONORS | 12/26 | 14/26 | 20/26 | 26/26 | 18/26 |

TABLE 6

HUMAN TRANSFUSION RECIPIENT (AN)

| DAYS POST TRANS. | C100 YEAST S/CO | C100 E. COLI S/CO | NS3 S/CO | CORE S/CO | E2 RIPA |
|---|---|---|---|---|---|
| 29 | 1.8 | 1.9 | 8.9 | 1.1 | − |
| 57 | 0.4 | .0.3 | 1.2 | 0.4 | − |
| 88 | 0.3 | 0.3 | 0.4 | 0.7 | − |
| 116 | 0.1 | 0.2 | 0.5 | 0.2 | − |
| 154 | 0.3 | 0.7 | 65.3 | 0.8 | − |
| 179 | 18.0 | 21.5 | 445.6 | 1.5 | − |
| 271 | 257.4 | 347.2 | 538.0 | 3.1 | + |
| 376 | 240.0 | 382.5 | 513.5 | 139.2 | + |
| 742 | 292.9 | 283.7 | 505.3 | 198.1 | + |
| 1105 | 282.1 | 353.9 | 456.1 | 202.2 | + |
| 1489 | 224.8 | 287.8 | 509.9 | 198.8 | + |

TABLE 7

HUMAN TRANSFUSION RECIPIENT (WA)

| POST TRANS. | C100 YEAST S/CO | C100 E. COLI S/CO | NS3 S/CO | CORE S/CO | E2 RIPA |
|---|---|---|---|---|---|
| 43 | 0.1 | 0.6 | 0.4 | 1.2 | − |
| 76 | 0.1 | 0.1 | 0.9 | 72.7 | − |
| 103 | 0.0 | 0.6 | 1.4 | 184.4 | + |
| 118 | 3.7 | 3.7 | 1.9 | 208.7 | + |
| 145 | 83.8 | 98.9 | 12.3 | 178.0 | + |
| 158 | 142.1 | 173.8 | 134.3 | 185.2 | + |
| 174 | 164.4 | 203.3 | 223.9 | 160.9 | + |

TABLE 8

HUMAN TRANSFUSION RECIPIENTS

| | AB STATUS | 2.0 GEN | E2 AB STATUS | SAMPLES TESTED |
|---|---|---|---|---|
| MI | STRONG RESPONSE | 78 DPT | NEG. | 1–178 DPT |
| KE | EARLY C100 | 103 DPT | NEG. | 1–166 DPT |
| WA | EARLY CORE | 76 DPT | POS. 103–173 DPT | 1–173 DPT |
| PA | EARLY C100 | 127 DPT | POS. 1491–3644 DPT | 1–3644 DPT |
| AN | EARLY 33C | 179 DPT | POS. 271–1489 DPT | 1–1489 DPT |

TABLE 9

SELECTED HCV E2 ANTIBODY POSITIVE SAMPLES

| SAMPLE | C100 YEAST S/CO | C100 E. COLI S/CO | NS3 S/CO | CORE S/CO | E1 RIPA |
|---|---|---|---|---|---|
| 50 | 101.04 | 133.69 | 163.65 | 263.72 | + |
| 121 | 1.28 | 4.77 | 172.65 | 291.82 | + |
| 503 | 113.7 | 128.5 | 154.5 | 283.3 | + |
| 505 | 130.6 | 143.8 | 133.4 | 186.1 | − |
| 476 | 0.37 | 1.29 | 144.66 | 302.35 | − |
| 728 | −0.01 | 0.26 | 90.37 | 246.30 | + |

What is claimed is:

1. An isolated APP-HCV-E2 fusion protein expressed by a mammalian expression vector pHCV-162.

2. An isolated APP-HCV-E2 fusion protein expressed by a mammalian expression vector pHCV-167.

3. A method for detecting hepatitis C virus (HCV) antigen or antibody in a test sample suspected of containing HCV antigen or antibody, wherein the improvement comprises contacting the test sample with the fusion protein of claim 1 or 2.

* * * * *